(12) United States Patent
Nock et al.

(10) Patent No.: US 11,147,541 B2
(45) Date of Patent: Oct. 19, 2021

(54) MRI BIOPSY SAMPLE

(71) Applicant: Devicor Medical Products, Inc., Cincinnati, OH (US)

(72) Inventors: Andrew P. Nock, Dayton, OH (US); Edward A. Rhad, Fairfield, OH (US); Robert M. Householder, Loveland, OH (US); Melody L. Stamper, Batavia, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 476 days.

(21) Appl. No.: 15/580,862

(22) PCT Filed: Jun. 9, 2016

(86) PCT No.: PCT/US2016/036659
§ 371 (c)(1),
(2) Date: Dec. 8, 2017

(87) PCT Pub. No.: WO2016/201083
PCT Pub. Date: Dec. 15, 2016

(65) Prior Publication Data
US 2018/0214140 A1 Aug. 2, 2018

Related U.S. Application Data

(60) Provisional application No. 62/174,012, filed on Jun. 11, 2015.

(51) Int. Cl.
*A61B 10/02* (2006.01)
*A61B 10/00* (2006.01)
(Continued)

(52) U.S. Cl.
CPC ...... *A61B 10/0283* (2013.01); *A61B 10/0041* (2013.01); *A61B 10/0275* (2013.01);
(Continued)

(58) Field of Classification Search
CPC ............ A61B 10/0283; A61B 10/0275; A61B 10/0041; A61B 2010/045; A61B 90/03;
(Continued)

(56) References Cited

U.S. PATENT DOCUMENTS 5,368,046 A * 11/1994 Scarfone .............. A61B 10/025
600/567
5,526,822 A 6/1996 Burbank et al.
(Continued)

OTHER PUBLICATIONS

Hahn, Markus et al., "Vacuum Assisted Breast Biopsy with Mammotome®," Nov. 11, 2012, copyright 2013 by Devicor Medical Germany GmbH, published in Germany by Springer Medizin Verlag. 128 pages.
(Continued)

*Primary Examiner* — Matthew Kremer
*Assistant Examiner* — Avery M Foley
(74) *Attorney, Agent, or Firm* — Frost Brown Todd LLC

(57) ABSTRACT

A depth stop assembly for use with a biopsy device targeting cannula includes a depth stop and a thumbwheel. The depth stop is configured to receive the targeting cannula. The depth stop has a lock to selectively restrict axial movement of the targeting cannula relative to the depth stop. The thumbwheel is motion-coupled to the depth stop. The thumbwheel has a circumferential finger gripping area.

20 Claims, 45 Drawing Sheets

(51) Int. Cl.
*A61B 17/34* (2006.01)
*A61B 90/11* (2016.01)
*A61B 90/00* (2016.01)

(52) U.S. Cl.
CPC .......... *A61B 17/3403* (2013.01); *A61B 90/03* (2016.02); *A61B 90/11* (2016.02); *A61B 10/0096* (2013.01); *A61B 2017/3411* (2013.01)

(58) Field of Classification Search
CPC ... A61B 90/02; A61B 90/11; A61B 2090/031; A61B 2090/032; A61B 2090/033; A61B 2090/034; A61B 2090/035; A61B 2090/036; A61B 2090/037; A61B 17/3403; A61B 2017/3411
See application file for complete search history.

(56) References Cited

U.S. PATENT DOCUMENTS

| | | | |
|---|---|---|---|
| 5,928,164 | A | 7/1999 | Burbank et al. |
| 6,017,316 | A | 1/2000 | Ritchart et al. |
| 6,086,544 | A | 7/2000 | Hibner et al. |
| 6,162,187 | A | 12/2000 | Buzzard et al. |
| 6,432,065 | B1 | 8/2002 | Burdorff et al. |
| 6,626,849 | B2 | 9/2003 | Huitema et al. |
| 6,752,768 | B2 | 6/2004 | Burdorff et al. |
| 7,442,171 | B2 | 10/2008 | Stephens et al. |
| 7,507,210 | B2 | 3/2009 | Hibner et al. |
| 7,648,466 | B2 | 1/2010 | Stephens et al. |
| 7,831,290 | B2 | 11/2010 | Hughes et al. |
| 7,837,632 | B2 | 11/2010 | Stephens et al. |
| 7,854,706 | B2 | 12/2010 | Hibner |
| 7,914,464 | B2 | 3/2011 | Burdorff et al. |
| 7,938,786 | B2 | 5/2011 | Ritchie et al. |
| 8,083,687 | B2 | 12/2011 | Parihar |
| 8,118,755 | B2 | 2/2012 | Hibner et al. |
| 8,162,849 | B2 | 4/2012 | Deshmukh et al. |
| 8,206,316 | B2 | 6/2012 | Hibner et al. |
| 8,241,226 | B2 | 8/2012 | Hibner et al. |
| 8,251,916 | B2 | 8/2012 | Speeg et al. |
| 8,277,394 | B2 | 10/2012 | Hibner |
| 8,366,635 | B2 | 2/2013 | Parihar et al. |
| 8,454,531 | B2 | 6/2013 | Speeg et al. |
| 8,532,747 | B2 | 9/2013 | Nock et al. |
| 8,622,924 | B2 | 1/2014 | Speeg et al. |
| 8,702,623 | B2 | 4/2014 | Parihar et al. |
| 8,764,680 | B2 | 6/2014 | Rhad et al. |
| 8,801,742 | B2 | 8/2014 | Rhad et al. |
| 8,858,465 | B2 | 10/2014 | Fiebig |
| 8,938,285 | B2 | 1/2015 | Fiebig et al. |
| 9,095,326 | B2 | 8/2015 | Ritchie et al. |
| 9,226,732 | B2 | 1/2016 | Azimpoor et al. |
| 9,326,755 | B2 | 5/2016 | Fiebig et al. |
| 9,345,457 | B2 | 5/2016 | Speeg et al. |
| 10,064,607 | B2 | 9/2018 | Keller et al. |
| 2006/0074345 | A1 | 4/2006 | Hibner |
| 2007/0167736 | A1 | 7/2007 | Dietz et al. |
| 2007/0255168 | A1 | 11/2007 | Hibner et al. |
| 2007/0255170 | A1* | 11/2007 | Hibner ............... A61B 10/0266 600/564 |
| 2008/0214955 | A1 | 9/2008 | Speeg et al. |
| 2009/0131821 | A1 | 5/2009 | Speeg et al. |
| 2009/0312763 | A1* | 12/2009 | McCormack ...... A61B 17/8822 606/83 |
| 2010/0023006 | A1* | 1/2010 | Ellman ............... A61B 18/1482 606/45 |
| 2010/0152610 | A1 | 6/2010 | Parihar et al. |
| 2010/0160815 | A1* | 6/2010 | Parihar ............. A61B 10/0275 600/564 |
| 2010/0160819 | A1 | 6/2010 | Parihar et al. |
| 2010/0160823 | A1* | 6/2010 | Parihar ............. A61B 10/0275 600/567 |
| 2010/0160824 | A1 | 6/2010 | Parihar et al. |
| 2012/0065542 | A1 | 3/2012 | Hibner et al. |
| 2013/0131545 | A1* | 5/2013 | Azimpoor ........... A61B 10/025 600/566 |
| 2013/0144188 | A1 | 6/2013 | Fiebig et al. |
| 2013/0289399 | A1* | 10/2013 | Choi .................. A61B 17/1671 600/431 |
| 2013/0324882 | A1 | 12/2013 | Mescher |
| 2014/0039343 | A1 | 2/2014 | Mescher et al. |
| 2014/0371711 | A1* | 12/2014 | Singh .................... A61B 90/11 604/506 |
| 2015/0025414 | A1 | 1/2015 | Rhad et al. |

OTHER PUBLICATIONS

International Search Report and Written Opinion dated Aug. 5, 2016 for International Application No. PCT/US2016/036659, 8 pages.
U.S. Appl. No. 62/429,471, entitled "Multi-Chamber Tissue Sample Cup for Biopsy Device," filed Dec. 2, 2016.
U.S. Appl. No. 62/429,379, entitled "Apparatus to Allow Biopsy Sample Visualization During Tissue Removal," filed Dec. 2, 2016.
Chinese Office Action dated Mar. 17, 2020 for Application No. 201680045557.4, 6 pages.
European Communication dated Aug. 28, 2019 for Application No. 16734498.5, 4 pages.

* cited by examiner

MRI BIOPSY SAMPLE

FIELD OF THE INVENTION

The present invention relates generally to vacuum-assisted breast biopsy devices for use in breast biopsy procedures using MRI.

BACKGROUND

Biopsy samples have been obtained in a variety of ways in various medical procedures including open and percutaneous methods using a variety of devices. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device. Biopsy devices may be used under stereotactic guidance, ultrasound guidance, MRI guidance, Positron Emission Mammography ("PEM" guidance), Breast-Specific Gamma Imaging ("BSGI") guidance or otherwise.

The state of the art for breast biopsy is vacuum-assisted breast biopsy. A current textbook in this area is "Vacuum-Assisted Breast Biopsy with Mammotome®", available Nov. 11, 2012, copyright 2013 by Devicor Medical Germany GmBh, published in Germany by Springer Medizin Verlag, Authors: Markus Hahn, Anne Tardivon and Jan Casselman, ISBN 978-3-642-34270-7.

Merely exemplary biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 5,928,164, entitled "Apparatus for Automated Biopsy and Collection of Soft Tissue," issued Jul. 27, 1999; U.S. Pat. No. 6,017,316, entitled "Vacuum Control System and Method for Automated Biopsy Device," issued Jan. 25, 2000; U.S. Pat. No. 6,086,544, entitled "Control Apparatus for an Automated Surgical Biopsy Device," issued Jul. 11, 2000; U.S. Pat. No. 6,162,187, entitled "Fluid Collection Apparatus for a Surgical Device," issued Dec. 19, 2000; U.S. Pat. No. 6,432,065, entitled "Method for Using a Surgical Biopsy System with Remote Control for Selecting an Operational Mode," issued Aug. 13, 2002; U.S. Pat. No. 6,626,849, entitled "MRI Compatible Surgical Biopsy Device," issued Sep. 11, 2003; U.S. Pat. No. 6,752,768, entitled "Surgical Biopsy System with Remote Control for Selecting an Operational Mode," issued Jun. 22, 2004; U.S. Pat. No. 7,442,171, entitled "Remote Thumbwheel for a Surgical Biopsy Device," issued Oct. 8, 2008; U.S. Pat. No. 7,648,466, entitled "Manually Rotatable Piercer," issued Jan. 19, 2010; U.S. Pat. No. 7,837,632, entitled "Biopsy Device Tissue Port Adjustment," issued Nov. 23, 2010; U.S. Pat. No. 7,854,706, entitled "Clutch and Valving System for Tetherless Biopsy Device," issued Dec. 1, 2010; U.S. Pat. No. 7,914,464, entitled "Surgical Biopsy System with Remote Control for Selecting an Operational Mode," issued Mar. 29, 2011; U.S. Pat. No. 7,938,786, entitled "Vacuum Timing Algorithm for Biopsy Device," issued May 10, 2011; U.S. Pat. No. 8,083,687, entitled "Tissue Biopsy Device with Rotatably Linked Thumbwheel and Tissue Sample Holder," issued Dec. 21, 2011; U.S. Pat. No. 8,118,755, entitled "Biopsy Sample Storage," issued Feb. 1, 2012; U.S. Pat. No. 8,206,316, entitled "Tetherless Biopsy Device with Reusable Portion," issued on Jun. 26, 2012; U.S. Pat. No. 8,241,226, entitled "Biopsy Device with Rotatable Tissue Sample Holder," issued on Aug. 14, 2012; U.S. Pat. No. 8,251,916, entitled "Revolving Tissue Sample Holder for Biopsy Device," issued Aug. 28, 2012; U.S. Pat. No. 8,454,531, entitled "Icon-Based User Interface on Biopsy System Control Module," published May 21, 2009, issued on Jun. 4, 2013; U.S. Pat. No. 8,532,747, entitled "Biopsy Marker Delivery Device," issued Sep. 10, 2013; U.S. Pat. No. 8,702,623, entitled "Biopsy Device with Discrete Tissue Chambers," issued on Apr. 22, 2014; U.S. Pat. No. 8,764,680, entitled "Handheld Biopsy Device with Needle Firing," issued on Jun. 11, 2014; U.S. Pat. No. 8,801,742, entitled "Needle Assembly and Blade Assembly for Biopsy Device," issued Aug. 12, 2014; U.S. Pat. No. 8,858,465, entitled "Biopsy Device with Motorized Needle Firing," issued Oct. 14, 2014; U.S. Pat. No. 8,938,285, entitled "Access Chamber and Markers for Biopsy Device," issued Jan. 20, 2015; U.S. Pat. No. 9,095,326, entitled "Biopsy System with Vacuum Control Module," issued Aug. 4, 2015 and U.S. Pat. No. 9,095,326, entitled "Biopsy System with Vacuum Control Module," issued Aug. 4, 2015. The disclosure of each of the above-cited U.S. Patents is incorporated by reference herein.

Additional exemplary biopsy devices and biopsy system components are disclosed in U.S. Pat. Pub. No. 2006/0074345, entitled "Biopsy Apparatus and Method," published Apr. 6, 2006 and now abandoned; U.S. Pat. Pub. No. 2008/0214955, entitled "Presentation of Biopsy Sample by Biopsy Device," published Sep. 4, 2008; U.S. Pat. Pub. No. 2009/0131821, entitled "Graphical User Interface For Biopsy System Control Module," published May 21, 2009, now abandoned; U.S. Pat. Pub. No. 2010/0152610, entitled "Hand Actuated Tetherless Biopsy Device with Pistol Grip," published Jun. 17, 2010, now abandoned; U.S. Pat. Pub. No. 2010/0160819, entitled "Biopsy Device with Central Thumbwheel," published Jun. 24, 2010, now abandoned; U.S. Pat. Pub. No. 2013/0053724, entitled "Biopsy Device Tissue Sample Holder with Bulk Chamber and Pathology Chamber," published Feb. 28, 2013, will issue on May 3, 2016 as U.S. Pat. No. 9,326,755; U.S. Pat. Pub. No. 2013/0144188, entitled "Biopsy Device With Slide-In Probe," published Jun. 6, 2013; and U.S. Pat. Pub. No. 2013/0324882, entitled "Control for Biopsy Device," published Dec. 5, 2013. The disclosure of each of the above-cited U.S. Patent Application Publications, U.S. Non-Provisional Patent Applications, and U.S. Provisional Patent Applications is incorporated by reference herein.

In U.S. Pat. No. 7,831,290, issued Oct. 20, 2010, the disclosure of which is incorporated by reference herein, a localization mechanism, or fixture, is described that is used in conjunction with a breast coil for breast compression and for guiding a core biopsy instrument during prone biopsy procedures in both open and closed Magnetic Resonance Imaging (MRI) machines. The localization fixture includes a three-dimensional Cartesian positionable guide for supporting and orienting an MRI-compatible biopsy instrument, and, in particular, a cannula/sleeve to a biopsy site of suspicious tissues or lesions. Another merely illustrative localization mechanism used for guiding a core biopsy instrument is disclosed in U.S. Pat. No. 7,507,210, entitled "Biopsy Cannula Adjustable Depth Stop," issued Mar. 24, 2009, the disclosure of which is incorporated by reference herein. The localization mechanism includes a grid plate configured to removably receive a guide cube capable of supporting and orienting an MRI-compatible biopsy instrument. For instance, a combination of an obturator and targeting cannula/sleeve may be introduced through a breast to a biopsy site via the guide cube, with proper positioning confirmed using MRI imaging. The obturator may then be removed and the needle of a biopsy device may then be inserted through the targeting cannula/sleeve to reach the targeted lesion.

A Z-stop may enhance accurate insertion, and prevent over-insertion or inadvertent retraction of a biopsy device targeting cannula/sleeve and obturator. In particular, a Z-stop may engage the localization fixture or cube at a distance from the patient set to restrict the depth of insertion of a biopsy device needle into a patient. Merely illustrative z-stop examples are disclosed in U.S. Pat. No. 7,507,210, entitled "Biopsy Cannula Adjustable Depth Stop," issued Mar. 24, 2009, the disclosure of which is incorporated by reference herein.

Some currently available MRI targeting sets include a targeting cube with two (2) access holes. This cube design does not lock into the Z-stop or targeting grid, meaning it can fit into the targeting grid in multiple orientations, thus allowing the two holes to align with multiple positions within the grid square space.

Some currently available MRI targeting cubes limit the positions within the targeting grid where the biopsy needle can be secured. This presents the risk that the needle may not be in optimal position to biopsy the desired tissue. In addition, some currently available targeting cubes do not have the ability to lock into either the targeting grid or the Z-stop. This can present alignment and usability issues if the cube falls out of position during the procedure.

While several systems and methods have been made and used for obtaining a biopsy sample, it is believed that no one prior to the inventor has made or used the invention described in the appended claims.

SUMMARY OF THE INVENTION

An aspect of the instant claimed invention is a guide system usable with a biopsy device targeting cannula, the guide system comprising: a depth stop assembly, wherein the depth stop assembly comprises:
- a depth stop device, wherein the depth stop device is configured to receive the targeting cannula, wherein the depth stop device is further configured to selectively restrict axial movement of the targeting cannula relative to the depth stop device, and
- a depth stop holder, wherein the depth stop holder comprises a body, wherein the body includes a pair of coupling members configured to couple the depth stop device to the depth stop holder, wherein the depth stop device is movable relative to the depth stop holder along at least on axis when the depth stop device is coupled to the depth stop holder; and
- a guide assembly, wherein the guide assembly comprises:
- a body, wherein the body defines a plurality of holes extending from a distal end to a proximal end of the body, wherein each hole of the plurality of holes is configured to receive the targeting cannula therein, and
- a lock feature, wherein the lock feature is selectively movable relative to the body of the guide assembly to selective couple the depth stop holder to the body of the guide assembly.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

Figure 1:
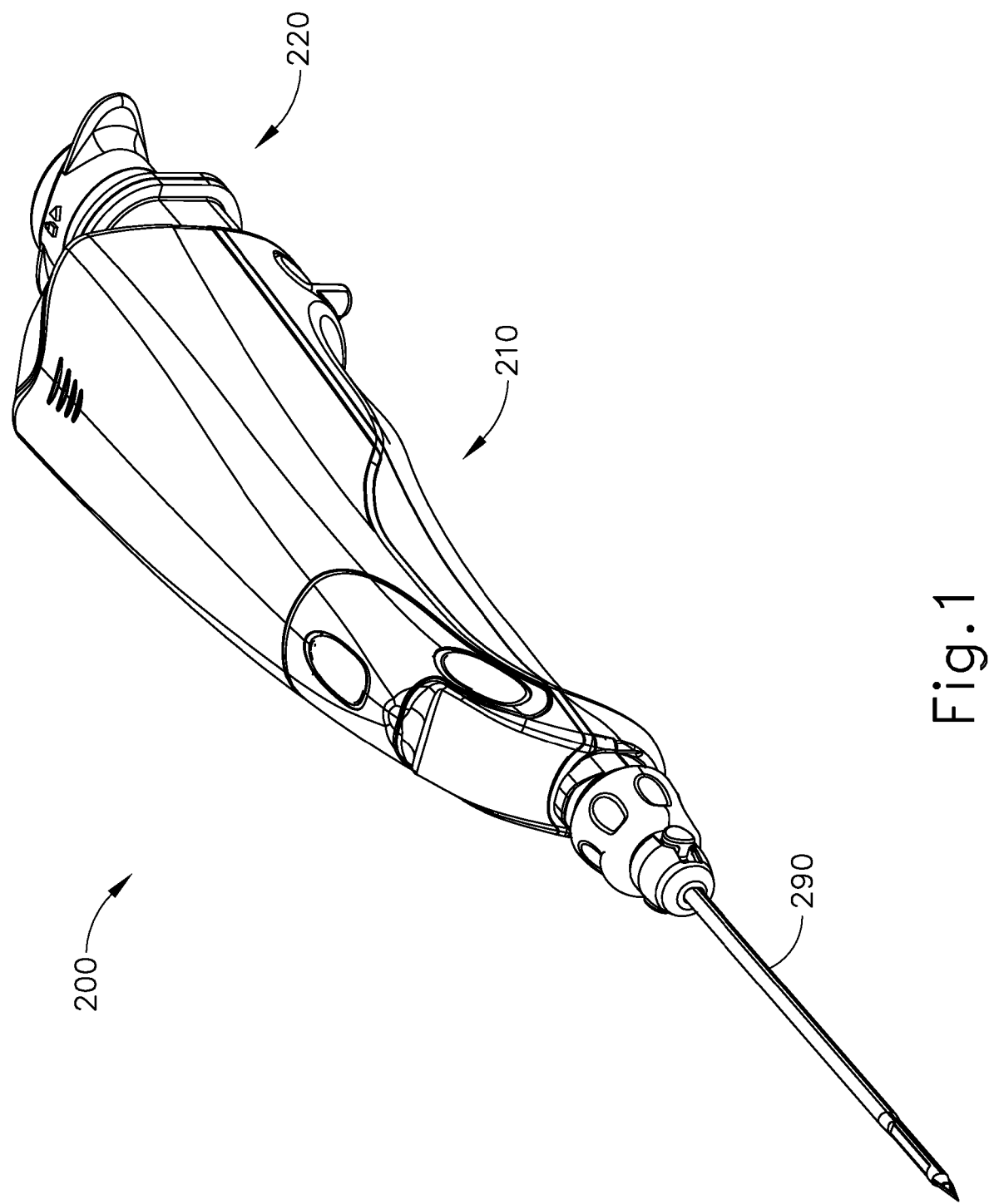
FIG. 1 depicts a perspective view of an exemplary alternative biopsy device that may be used with the biopsy system of FIG. 1.

The drawings are not intended to be limiting in any way, and it is contemplated that various embodiments of the invention may be carried out in a variety of other ways, including those not necessarily depicted in the drawings.

The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

The MRI targeting cube acts as a needle guide for the targeting set and the biopsy device. This provides stability and positioning support for the biopsy needle, allowing the physician to reach the desired area of the breast with confidence that the device will not move out of alignment during sampling. The cubes described in the instant patent application also feature direct connection and locking to the Z-stop, additional device stabilization, an increase in skin-nick visibility and an increase in stability and accuracy. Each of the cube designs offer four (4) targeting holes, which allow for fine-tuning of biopsy needle position.

There are six embodiments of the instant claimed invention.

The first embodiment is a targeting cube with four (4) access holes, including a friction lock to grid and a lock to Z-stop. The second embodiment is a targeting cube with four (4) access holes, including a rotating bezel to lock to grid and Z-stop. The third embodiment is a targeting cube with four (4) access holes, including lock to grid through a telescoping-latching mechanism and a lock to Z-stop. The fourth embodiment is a targeting cube with four (4) access holes, including a built-in Z-stop carriage assembly and a rotating lock to grid. The fifth embodiment is a foldable cube with four (4) access holes, including a built-in Z-stop that locks in place via hinge. The sixth embodiment is a proximal telescopic needle rotation device.

FIGS. 1, 2, 3, 4, 5, 6, 7, 8 and 9 of U.S. Pat. No. 7,507,210, incorporated by reference in its entirety, depict a perspective view of a MM biopsy system including a control module remotely coupled to a biopsy device, and including a localization fixture with a lateral grid plate used in conjunction with a rotatable cube to position an obturator or a probe of the biopsy device to a desired insertion depth as set by a ring stop.

During the breast biopsy procedure, typically the patient's breasts hang pendulously respectively into breast apertures on the examination table. For convenience, herein a convention is used for locating a suspicious lesion by Cartesian coordinates within breast tissue referenced to localization fixture and to thereafter selectively position an instrument, such as the needle of a probe that is engaged to a holster portion to form biopsy device.

To enhance hands-off use of biopsy system, especially for repeated re-imaging within the narrow confines of a closed bore MRI machine, biopsy system may also guide obturator encompassed by cannula. Depth of insertion is controlled by a depth stop device longitudinally positioned on either needle or cannula. Alternatively, depth of insertion may be controlled in any other suitable fashion.

In typical MRI breast biopsy procedures, a targeting set comprising cannula and obturator is associated with probe. In particular the obturator is slid into cannula and the combination is guided through guide cube to the biopsy site within the breast tissue. The obturator is then withdrawn from cannula, then the needle of the probe is inserted in cannula, and then biopsy device is operated to acquire one or more tissue samples from the breast via needle. One known challenge when conducting a MRI imaged breast biopsy is poor visibility during MRI imaging.

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 2:
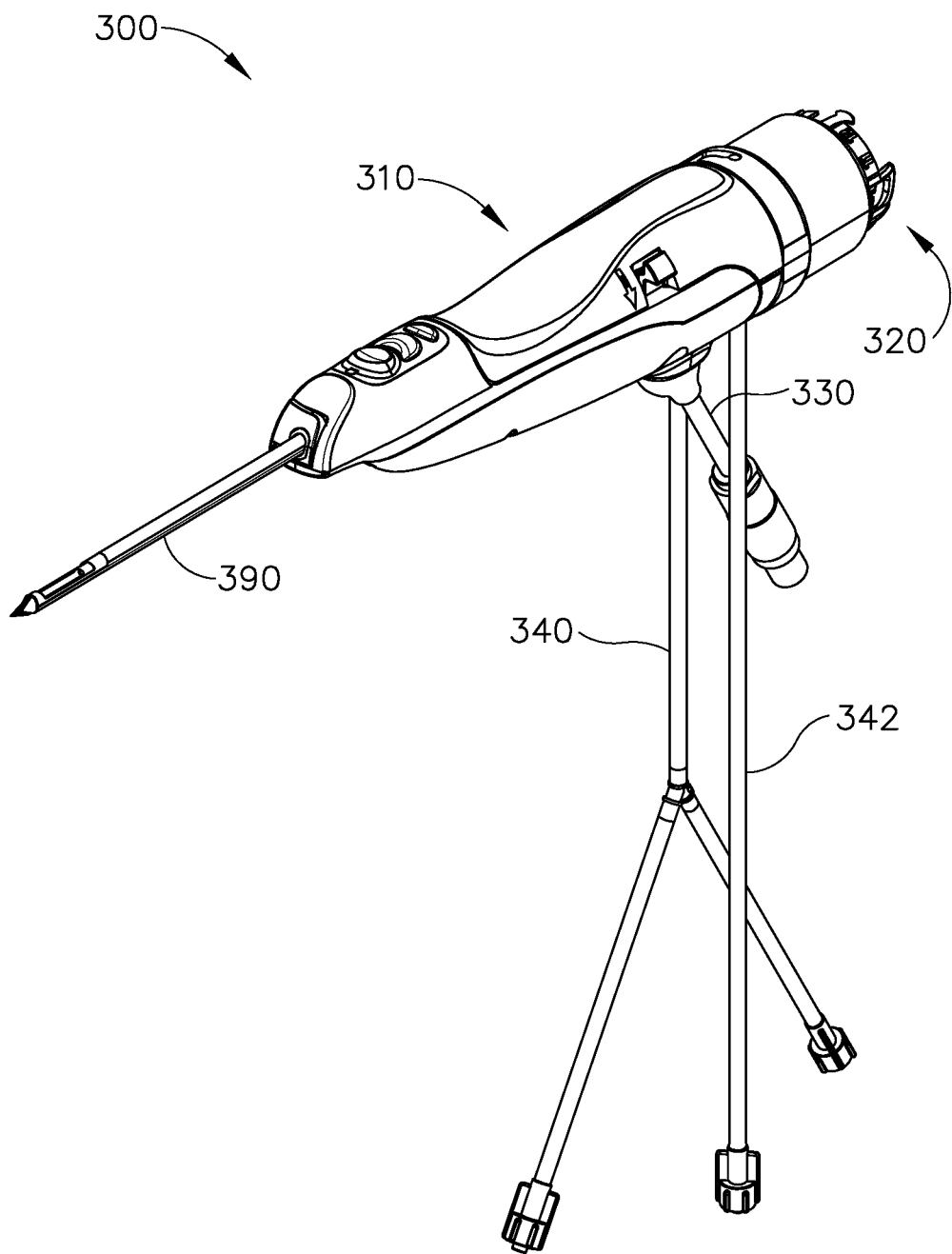
FIG. 2 depicts a perspective view of another exemplary alternative biopsy device that may be used with the biopsy system of FIG. 1.
Figure 3:
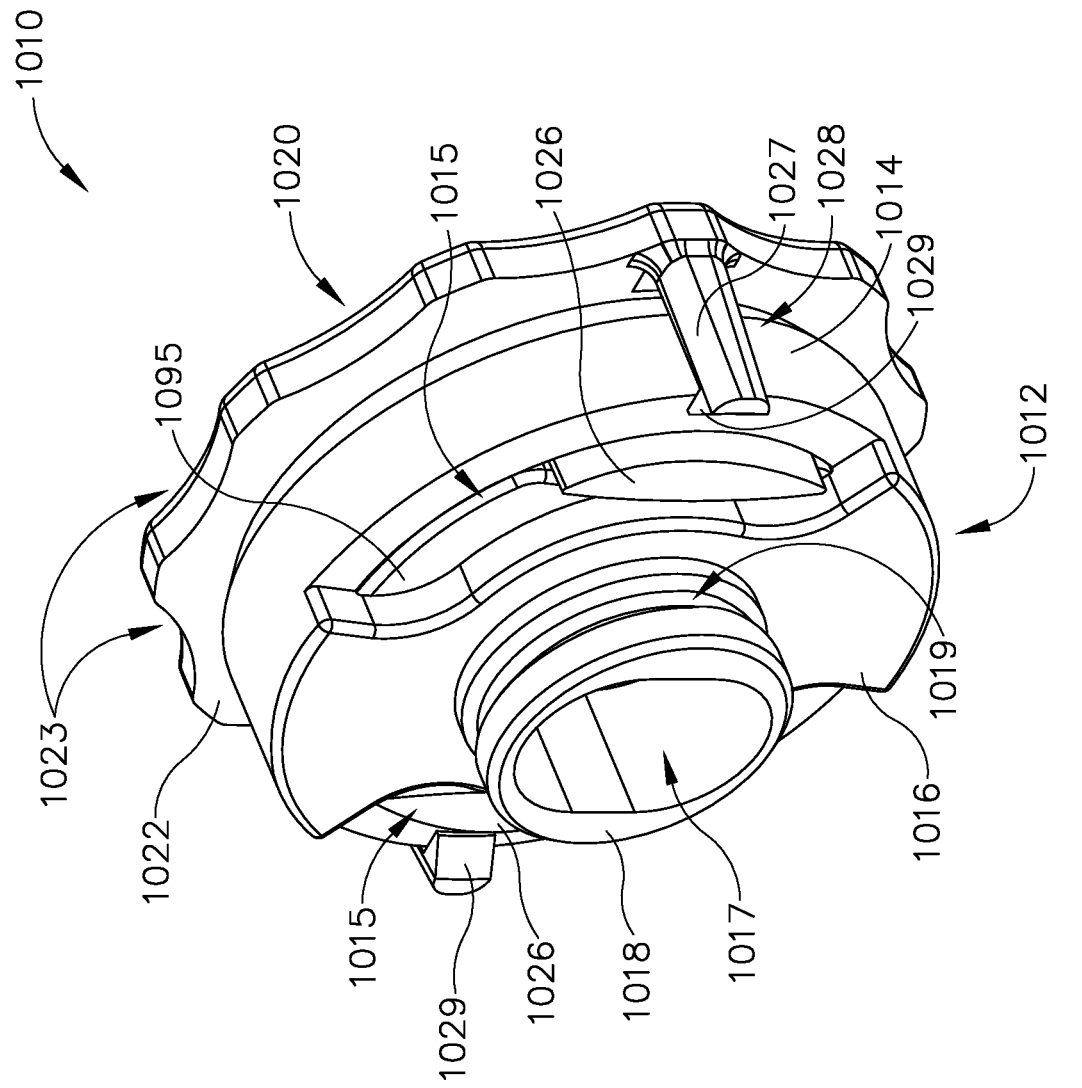
FIG. 3 depicts a perspective view of a depth stop assembly for use with the biopsy system of FIG. 1.

A MRI compatible biopsy system is described in U.S. Pat. No. 8,162,849 B2, (hereinafter US '849) which is incorporated by reference in its entirety. In FIGS. 1-3 of US '849 a MRI compatible biopsy system is shown. In US '849, from col 3, ln 60-67 to col 5, ln 22, the setup and operation of the MRI compatible biopsy system is described.

An example of a localization assembly is described starting in Column 5, line 23-and ending in column 6, ln 26 of US '849.

An exemplary biopsy device is shown in FIG. 1 of US '849. An exemplary biopsy device is described starting in col 6, ln 27 and ending in col. 7, ln 67.

It should be understood that although the biopsy system as described in US '849 uses a disposable probe assembly, other suitable probe assemblies and biopsy device assemblies may be utilized.

By way of example only, a biopsy device such as the biopsy device (200) shown in FIG. 1 may be used in the biopsy system. Biopsy device (200) of this example comprises a needle (290) extending distally from a handpiece (210); and a tissue sample holder (220) disposed at a proximal end of handpiece (210). Needle (290) is configured to operate substantially similar to needle (90) discussed above. For instance, needle (290) is configured to cooperate with a cutter to obtain tissue samples from a biopsy site. Tissue sample holder (220) is configured to store tissue samples received through needle (290). By way of example only, biopsy device (200) may be configured in accordance with at least some of the teachings of U.S. Pat. No. 8,206,316, entitled "Tetherless Biopsy Device with Reusable Portion," issued Jun. 26, 2012, the disclosure of which is incorporated by reference herein; U.S. Pat. No. 8,277,394, entitled "Multi-Button Biopsy Device," issued Oct. 2, 2012, the disclosure of which is incorporated by reference herein; and/or U.S. Pub. No. 2012/0065542, entitled "Biopsy Device Tissue Sample Holder with Removable Tray," published Mar. 15, 2012, the disclosure of which is incorporated by reference herein.

As yet another merely illustrative example, a biopsy device such as the biopsy device (300) shown in FIG. 2 may be used in the biopsy system. Biopsy device (300) of this example comprises a needle (390) extending distally from a handpiece (310) and a tissue sample holder (320) disposed at a proximal end of handpiece (310). Needle (290) is configured to operate substantially similar to needle (90) discussed above. For instance, needle (390) is configured to cooperate with a cutter to obtain tissue samples from a biopsy site. Tissue sample holder (320) is configured to store tissue samples received through needle (390). A cable (330) provides communication of electrical power, commands, etc. while conduits (340, 342) provide fluid communication. By way of example only, biopsy device (300) may be configured in accordance with at least some of the teachings of U.S. Pub. No. 2010/0160824, the disclosure of which is incorporated by reference herein; U.S. Patent Pub. No. 2013/0144188, entitled "Biopsy Device with Slide-In Probe," published Jun. 6, 2013, the disclosure of which is incorporated by reference herein; U.S. Patent Pub. No. 2013/0324882, entitled "Control for Biopsy Device," published Dec. 5, 2013, the disclosure of which is incorporated by reference herein; U.S. Patent Pub. No. 2014/0039343, entitled "Biopsy System," published Feb. 6, 2014, the disclosure of which is incorporated by reference herein; and/or U.S. patent application Ser. No. 14/469,761, entitled "Tissue Collection Assembly for Biopsy Device," filed Aug. 27, 2014, the disclosure of which is incorporated by reference herein.

Still other suitable forms of biopsy devices that may be used in conjunction with the various alternative components of system as described herein will be apparent to those of ordinary skill in the art.

In some versions, a guide cube may comprise a body defined by one or more edges and faces. The body may include one or more guide holes or other types of passages that extend between faces of the guide cube and that may be used to guide an instrument such as a biopsy device or a portion of a biopsy device (e.g., needle of biopsy device, a combination of cannula and obturator; etc.). Guide cubes may be rotatable about one, two, or three axes to position the one or more guide holes or passages of the guide cube into a desired position.

US '849, col. 8, ln 41-67 to col. 15, ln 14 describes guide cubes in more detail.

In some other versions, known guide cubes are replaced with an alternative guide cube or other guide structure that are configured and operable in accordance with at least some of the teachings of U.S. Pat. App. Publication No. US 2015/0025414 A1, entitled "Biopsy Device Targeting Features," filed Jul. 18, 2014, and published Jan. 22, 2015, the disclosure of which is incorporated by reference herein.

Exemplary depth stop devices are described in U.S. Pat. No. 7,507,210B2, "Biopsy Cannula Adjustable Depth Stop", issued 24 Mar. 2009.

In some examples obturator and cannula discussed above and in the cited publications may be usable with alternative depth stop devices as compared with the depth stop devices cited in the references. In addition or in the alternative, depth stop device may be usable in conjunction with certain adaptor features. Such alternative depth stop devices may be desirable to generally improve the usability and or functionality of obturator and/or cannula. In other examples, some depth stop devices may include features to permit depth stop device to connect to other components of a biopsy system similar to the biopsy system described above.

For instance, in some examples it may be desirable to selectively attach the depth stop device to a guide cube similar to the guide cube(s) described in the cited references. Such features may be desirable because of improved usability of the biopsy system achieved through enhanced stability and/or control of obturator and/or cannula. Various examples of how a depth stop device may be reconfigured to be attachable to various components of the biopsy system will be described in greater detail below; while other examples will be apparent to those of ordinary skill in the art according to the teachings herein. It should be understood that the depth stop device examples described in the following text may function substantially similar to depth stop device and may be readily usable with obturator and cannula described above. It should also be understood that the depth stop device examples described in the following text may be readily usable with guide cube described above. In particular, the depth stop device examples described below may be used to assist in biopsy device needle targeting within a patient's breast using MRI guidance. It should also be understood that the depth stop device examples discussed below may be used with any of the biopsy devices discussed above or otherwise disclosed herein.

Figure 4:
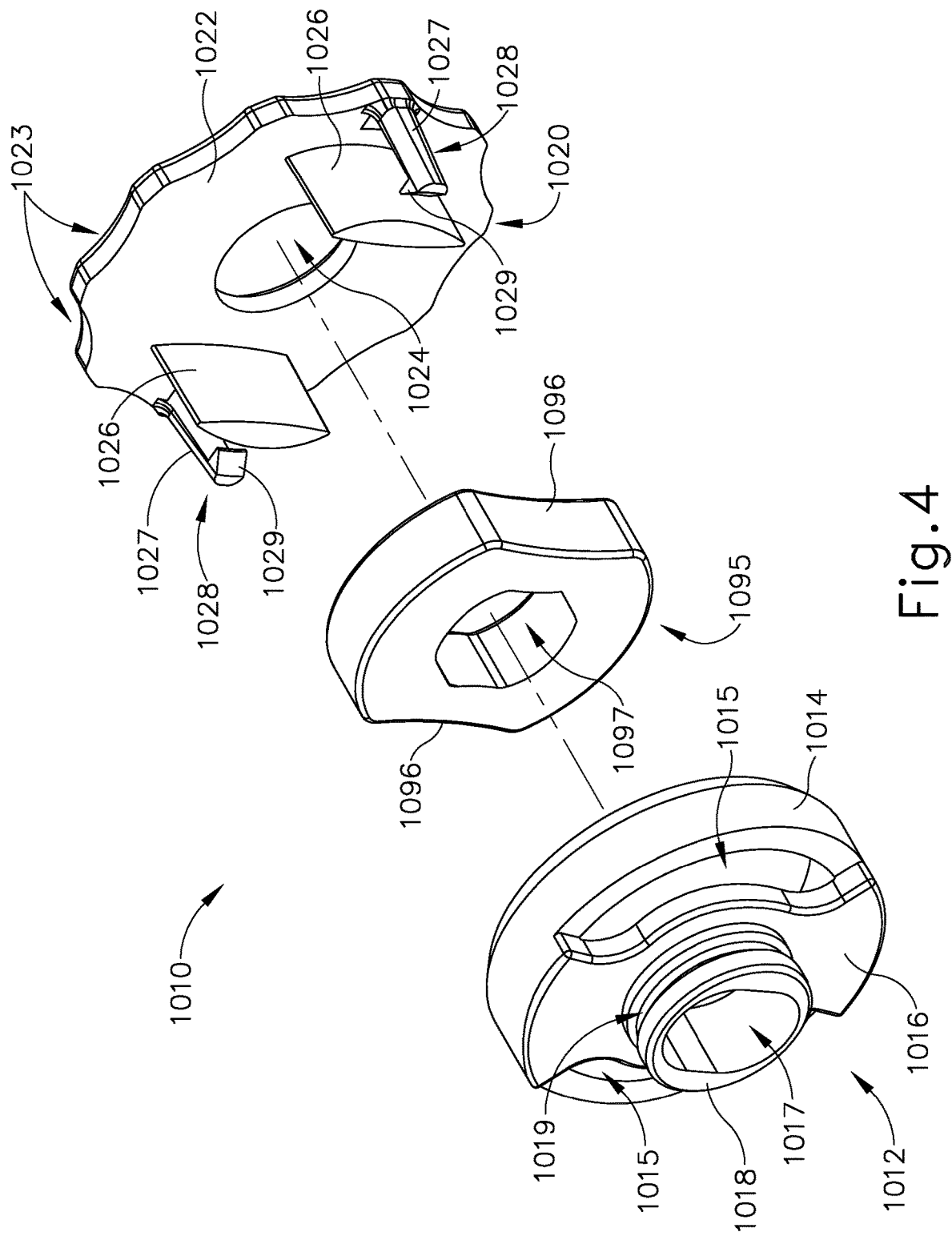
FIG. 4 depicts a perspective exploded view of the depth stop assembly of FIG. 3.
Figure 5:
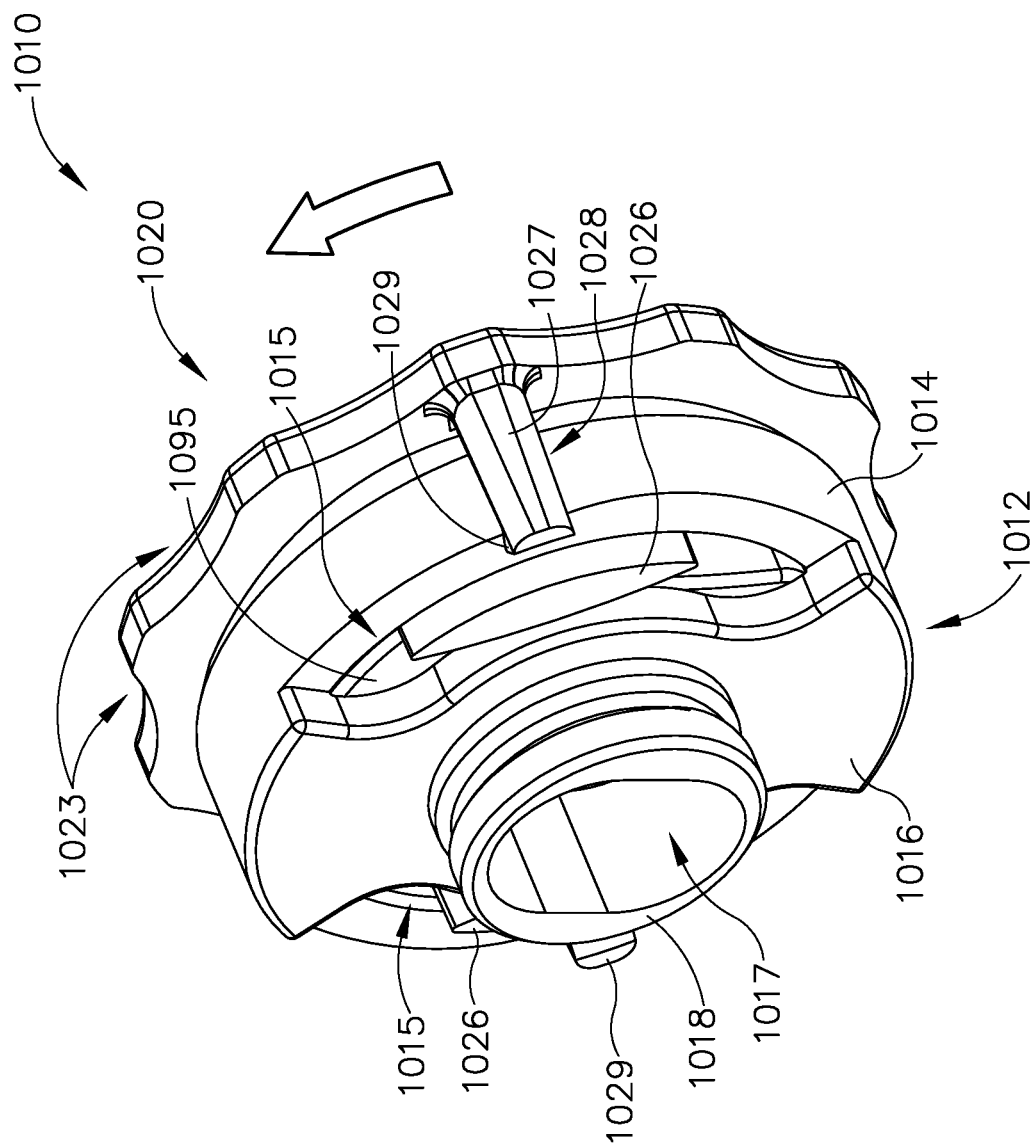
FIG. 5 depicts a perspective view of the depth stop assembly of FIG. 3, with the depth stop assembly in a locked position.

FIGS. 3-5 show an exemplary depth stop assembly (1010) that may be used in conjunction with, or in lieu of, depth stop device of the biopsy system described above and in the cited references. Depth stop assembly (1010) comprises a depth stop holder (1012), a depth stop device (1095) and a rotation member (1020). Depth stop holder (1012) is generally configured to receive depth stop device (1095). As will be described in greater detail below, when depth stop holder (1012) is coupled to rotation member (1020), depth stop device (1095) is laterally and longitudinally secured between depth stop holder (1012) and rotation member (1020). Depth stop holder (1012) comprises a generally cylindrical body (1014), a cross member (1016), and a cube coupling member (1018).

Body (1014) is generally hollow and is configured to receive depth stop device (1095) and at least a portion of rotation member (1020) therein. The inner diameter of body (1014) corresponds to the diameter of depth stop device (1095). As will be described in greater detail below, rotation member (1020) generally restricts rotation of depth stop device (1095) to a certain predetermined range of motion relative to depth stop holder (1012). However, in the absence of rotation member (1020), it should be understood that the shape of body (1014) permits rotation of depth stop device (1095) 360 degrees relative to depth stop holder (1012).

Cross member (1016) is of integral construction with body (1014) extending across the hollow inner diameter of body (1014) on the distal end of body (1014). As will be understood, cross member (1016) is generally configured to confine depth stop device (1095) within body (1014). As will also be understood, the shape of cross member (1016) is generally configured to define the predetermined range of motion through which rotation member (1020) restricts rotation of depth stop device (1095). The shape of cross member (1016) defines a pair of gaps (1015). As will be described in greater detail below, gaps (1015) are generally configured to permit at least a portion of rotation member (1020) to pass through body (1014) to a position adjacent to cross member (1016).

Cross member (1016) further defines a bore (1017), which extends through cross member (1016) being further defined by cube coupling member (1018). Bore (1017) is generally configured to receive an obturator and cannula similar to obturator and cannula described above. Accordingly, it should be understood that a suitable obturator and cannula may pass through depth stop holder (1012) and into a guide cube similar to guide cube described above.

Cube coupling member (1018) protrudes distally from cross member (1016). As described above, cube coupling member (1018) also at least partially defines bore (1017) such that obturator and cannula may extend through cube coupling member (1018) as well as cross member (1016). Bore (1017) of the present example is defined by a generally ovular cross-sectional shape. It should be understood that this shape corresponds to the shape of the cannula and obturator. Because of the ovular shape, it should be understood that the rotational position of depth stop holder (1012) is fixed relative to the cannula and obturator when depth stop holder (1012) is disposed thereon. Although bore (1017) is configured to prevent relative rotation between depth stop holder (1012) and the cannula and the obturator, it should be understood that such a feature is merely optional and may be omitted in some examples. Accordingly, in such examples depth stop holder (1012) may be configured to be fully rotatable about the cannula and the obturator. Although merely optional, it should be understood that rotational fixation of depth stop holder (1012) may be desirable to limit the rotation of depth stop device (1095) through the predetermined range of motion as will be described in greater detail below.

Cube coupling member (1018) includes an annular connector channel (1019). It should be understood that in some examples a guide cube similar to guide cube described above may include certain coupling features. Such coupling features may include protrusions and/or detent features that may permit selective coupling with connector channel (1019). Of course, numerous other suitable coupling features may be incorporated into the guide cube. Accordingly, it should be understood that where such features are varied in the guide cube, connector channel (1019) may also be correspondingly varied to accommodate.

Depth stop device (1095) is best seen in FIG. 4. It should be understood that depth stop device (1095) is substantially the same as depth stop device described above, except as otherwise noted herein. Additionally, it should be understood that in some examples depth stop device(s) described in the cited references may be used with depth stop assembly (1010) in lieu of depth stop device (1095) described herein. As can be seen, depth stop device (1095) is generally cylindrical in construction with two indentations (1096) on opposing sides. Depth stop device (1095) includes an opening (1097) approximately though the center of depth stop device (1095). Although not shown, it should be understood that in some examples depth stop device (1095) includes blades or other protrusions that extend into opening (1097). Such blades or protrusions are configured to dig into but not cut the cannula as depth stop device (1095) is rotated about the cannula, thereby locking the longitudinal position of depth stop device (1095) relative to the cannula. (92)

Rotation member (1020) is also best seen in FIG. 4. Rotation member (1020) is configured to be rotated by an operator to actuate depth stop device (1095) relative to the cannula between an unlocked and locked position. As can be seen, rotation member (1020) comprises a thumbwheel portion (1022), a pair of actuation members (1026), and a pair of lock arms (1028). Thumbwheel portion (1022) is generally circular in shape with a plurality of grips (1023) disposed around the perimeter of thumbwheel portion (1022). Grips (1023) are configured to enhance the gripability of thumbwheel portion (1022) such that an operator may manually rotate rotation member (1020).

Thumbwheel portion (1022) further defines an opening (1024), which is configured to receive the cannula and obturator. Unlike bore (1017) described above, opening (1024) of the present example is circular in cross-sectional shape. As will be understood, such a cross-sectional shape permits thumbwheel portion (1022) to rotate relative to the cannula and the obturator to thereby permit rotation member (1020) to rotate depth stop device (1095) between the unlocked and locked positions.

Each actuation member (1026) extends distally from thumbwheel portion (1022). The internal face of each actuation member (1026) is shaped to correspond or be complementary to indentations (1096) of depth stop device (1095). Thus, when depth stop assembly (1010) is assembled, the internal face of each actuation member (1026) is positioned adjacent to a respective surface of each indentation (1096). Similarly, each external face of each actuation member (1026) is shaped to correspond to the inner diameter of body (1014) of depth stop holder (1012). Thus, each actuation member (1026) is configured to be disposed between each indentation (1096) of depth stop device (1095) and through gaps (1015) in body (1014) of depth stop holder (1012). As will be described in greater detail below, this relationship permits rotation member (1020) to rotate depth stop device (1095) through the predetermined range of motion from an unlocked position to a locked position.

Each lock arm (1028) also extends distally from thumbwheel portion (1022). The distal end of each lock arm (1028) includes a resilient member (1027), with a lock tooth (1029) extending inwardly from resilient member (1027). It should be understood that lock arms (1028) are configured to operate together to act as a snap fit feature, selectively securing rotation member (1020) to depth stop holder (1012). In particular, as rotation member (1020) is inserted onto depth stop holder (1012), body (1014) of depth stop holder (1012) engages with lock teeth (1029) of each lock arm (1028), displacing each lock arm (1028) outwardly against the resilient bias of resilient members (1027). Once body (1014) clears teeth (1029), resilient members (1027) urge teeth (1029) back into position such that each tooth (1029) engages with the distal face of body (1014), thereby securing rotation member (1020) to depth stop holder (1012).

An exemplary use of depth stop assembly (1010) can be seen by comparing FIGS. 3 and 5. As can be seen, depth stop assembly (1010) initially begins in the unlocked position as shown in FIG. 3. In the unlocked position, rotation member (1020) is positioned such that each actuation member (1026) acts on indentations (1096) of depth stop device (1095) to position opening (1097) of depth stop device (1095) into angular alignment with bore (1017) of depth stop holder (1012). It should be understood that when depth stop device (1095) is in this position, the cannula and obturator may be freely inserted through depth stop assembly (1010) with limited interference of any longitudinal translation of the cannula and obturator. In other words, longitudinal translation of the cannula and obturator is unlocked relative to depth stop assembly (1010).

To lock translation of the cannula and obturator relative to depth stop assembly (1010), an operator may transition depth stop device (1095) from the unlocked position shown in FIG. 3 to the locked position shown in FIG. 5. To transition depth stop device (1095) to the locked position shown in FIG. 5, an operator may grasp thumbwheel portion (1022) and rotate rotation member (1020) in the counter clockwise direction relative to depth stop holder (1012) and relative to cannula. As rotation member (1020) is rotated, each actuation member (1026) acts on each indentation (1096) of depth stop device (1095) to rotate depth stop device (1095) in a counter clockwise direction relative to depth stop holder (1012) and relative to cannula. As depth stop device (1095) rotates, blades or other protrusions within opening (1097) of depth stop device (1095) will dig into the cannula without cutting the cannula, thereby locking relative movement between depth stop device (1095) and the cannula. Although rotation member (1020) is described and shown herein as being rotatable in a counter clockwise direction to transition depth stop device (1095) to the locked position, no such limitation is intended. For instance, it should be understood that in the present example depth stop device (1095) may also be transitioned to the locked position by clockwise rotation of rotation member (1020).

It should be understood that in some examples, it may be desirable to prevent rotation of depth stop device (1095) past a certain predetermined point, thereby limiting rotation of depth stop device (1095) to the predetermined range of motion described above. For instance, in some examples if depth stop device (1095) is rotated beyond the locked position shown in FIG. 5, additional rotation may result in damage to the cannula and/or slippage between depth stop device (1095) and the cannula. Thus, it may be desirable to include features in depth stop assembly (1010) to limit rotation of depth stop device (1095) relative to cannula to the predestined range of motion described above.

In the present example, further rotation of depth stop device (1095) relative to cannula is generally limited by depth stop holder (1012). In particular, as can be seen in FIG. 5, additional counter clockwise rotation of rotation member (2020) will result in actuation members (1026) being positioned adjacent to cross member (1016) of depth stop holder (1012). Once adjacent to depth stop holder (1012), further rotation will be prevented by engagement between cross member (1016) and actuation members (1026). As described above, bore (1017) of depth stop holder (1012) is complementary to the shape of the cannula and the obturator to prevent relative rotation between depth stop holder (1012) and cannula and the obturator. Accordingly, cross member (1016) is relatively fixed to thereby prevent further rotation of rotation member (1020). Of course, this feature is merely optional and in some examples depth stop holder (1012) may be freely rotatable relative to the cannula and obturator, thereby permitting further rotation of depth stop device (1095).

It should be understood from the foregoing that when depth stop assembly (1010) is secured to cannula in the locked configuration such that the longitudinal position of depth stop assembly (1010) is locked in place along the length of cannula, depth stop assembly (1010) will restrict the depth to which cannula and obturator may be inserted into guide cube. In particular, depth stop assembly (1010) will engage the proximal face of guide cube and thereby arrest further insertion of cannula and obturator into guide cube.

FIGS. 6-9 show an another exemplary depth stop assembly (1110) that may be used in conjunction with, or in lieu of, depth stop device of the biopsy system described above. Depth stop assembly (1110) is generally similar to depth stop assembly (1010) described above, except as otherwise noted herein. Depth stop assembly (1110) comprises a depth stop holder (1112), and a depth stop device (1195). Depth stop holder (1112) is generally configured to receive depth stop device (1195). As will be described in greater detail below, when depth stop holder (1112) is coupled to depth stop device (1195), depth stop device is longitudinally and rotationally secured to depth stop holder (1112).

Depth stop holder (1112) comprises a generally rectangular body (1114). Body (1114) includes a detent feature (1115) and an opening (1116) disposed at approximately the center of body (1114). Detent feature (1115) is configured to engage with depth stop device (1195) to selectively secure the lateral position of depth stop device (1195) as will be described in greater detail below. Opening (1116) has a generally ovular cross-section. In the present example, the shape of opening (1116) generally corresponds to the cross-sectional shape of a cannula and obturator similar to cannula and obturator described above. Because of the corresponding shape between opening (1116) and the cannula and the obturator, it should be understood that the rotational position of depth stop holder (1112) is generally fixed relative to the cannula and the obturator.

Depth stop holder (1112) further includes a plurality of guide features (1120) extending proximally from opposing sides of body (1114). In particular, each set of guide features (1120) comprises an upper stop member (1122), a lower stop member (1124), and a lock arm (1126). Upper and lower stop members (1122, 1124) are generally configured to define a predetermined lateral range of motion for depth stop member (1195). Each stop member (1122, 1124) has a generally curved cross-sectional shape. For instance, upper stop member (1122) curves inwardly near the upper portion of body (1114). Similarly, lower stop member (1124) curves inwardly near the lower portion of body (1114). As will be understood, the inward curve of each stop member (1122, 1124) generally corresponds to the shape of depth stop device (1195). Accordingly, as will be described in greater detail below, each stop member (1122, 1124) is configured to arrest movement of depth stop device (1195) when depth stop device (1195) engages with a given stop member (1122, 1124).

Each lock arm (1126) is disposed at approximately the longitudinal center of body (1114). As will be described in greater detail below, lock arms (1126) are generally configured to operate cooperatively to selectively secure depth stop device (1195) to depth stop holder (1112). In the present example, each lock arm (1126) comprises a resilient member (1128) and a lock tooth (1129). Resilient member (1128) is generally relatively flexible to permit deflection of lock tooth (1129). Although flexible, resilient member (1128) is also relatively stiff to resiliently bias lock tooth (1129) to the position shown in FIGS. 6 and 7. Each lock tooth (1129) comprises a generally triangular shape. As will be described in greater detail below, the triangular shape of each lock tooth (1129) is generally configured to engage with at least a portion of depth stop device (1195) to selectively secure depth stop device (1195) to depth stop holder (1112).

Figure 8:
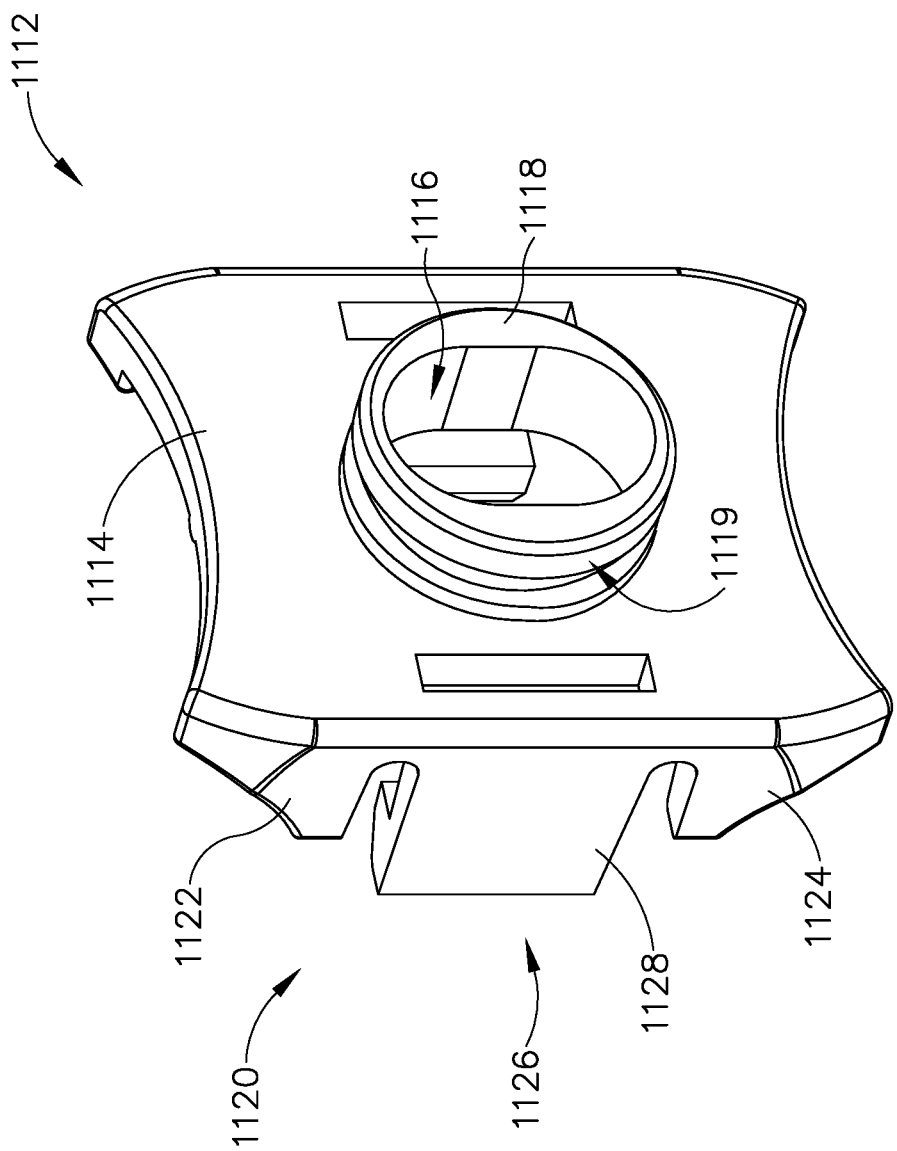
FIG. 8 depicts a perspective view of a depth stop holder of the depth stop assembly of FIG. 6.

FIG. 8 shows the distal face of depth stop holder (1112). As can be seen, depth stop holder (1112) further comprises a cube coupling member (1118). Cube coupling member (1118) protrudes distally from the distal face of depth stop holder (1112). Cube coupling member (1118) also at least partially defines opening (1116) such that the cannula and the obturator may extend through cube coupling member (1118). Cube coupling member (1118) includes an annular connector channel (1119). It should be understood that in some examples a guide cube similar to guide cube described above may include certain coupling features. Such coupling features may include protrusions and/or detent features that may permit selective coupling with connector channel (1119). Of course, numerous other suitable coupling features may be incorporated into the guide cube. Accordingly, it should be understood that where such features are varied in the guide cube, connector channel (1119) may also be correspondingly varied to accommodate.

Figure 7:
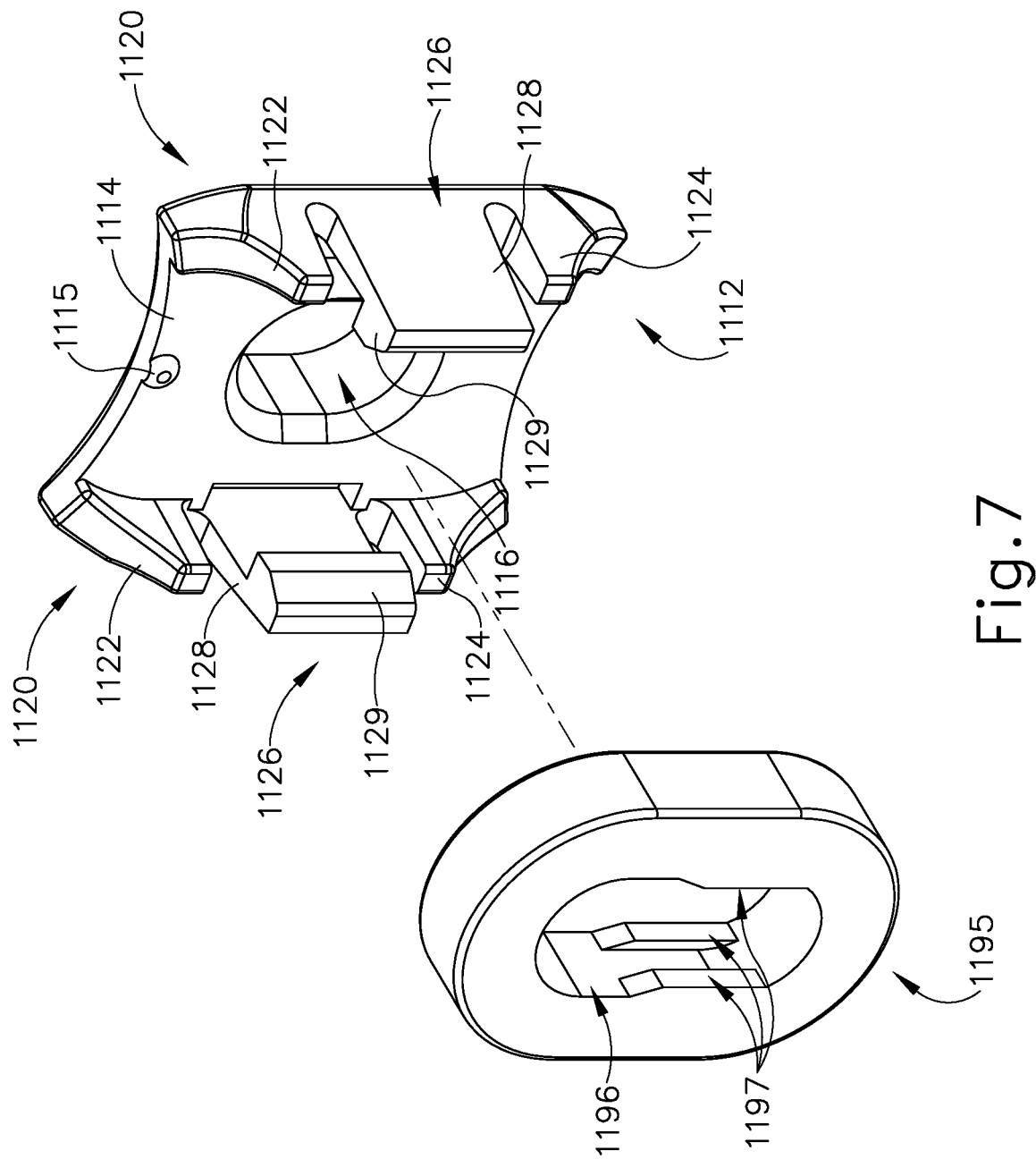
FIG. 7 depicts an exploded perspective view of the depth stop assembly of FIG. 6.

Depth stop device (1195) is best seen in FIG. 7. Depth stop device (1195) of the present example is similar to depth stop device (1095) described above. However, unlike depth stop device (1095), depth stop device (1195) of the present example is configured to move laterally to transition between an unlocked and locked position instead of rotationally. In particular, depth stop device (1195) comprises an opening (1196) similar to opening (1097) described above. However, unlike opening (1097), opening (1196) of the present example comprises a generally elongate ovular shape to permit lateral translation of depth stop device (1195).

Depth stop device (1195) further includes a plurality of cannula engagement members (1197) extending into at least a portion of opening (1196). Cannula engagement members (1197) are generally configured to engage with the cannula to selectively lock the longitudinal position of depth stop device (1195) relative to the cannula. For instance, in some versions cannula engagement members (1197) are elastomeric and deform against cannula to provide an increased frictional fit between depth stop device (1195) and cannula. In some other versions, cannula engagement members (1197) are rigid and provide an interference fit with cannula. In some other versions, cannula engagement members (1197) are sharp and dig into cannula.

Cannula engagement members (1197) of the present example are disposed adjacent to the bottom of opening (1196). With this positioning, depth stop device (1195) is configured to translate upwardly to lock relative to the cannula. In other examples, cannula engagement members (1197) may alternatively be disposed adjacent to the top of opening (1196) to permit locking when depth stop device (1195) is translated downwardly. Although cannula engagement members (1197) of the present example are shown as having a generally rectangular shape, no such limitation is intended. For instance, in some examples cannula engagement members (1197) include a sharpened or pointed surface that is configured to dig into the cannula to grip the cannula but not damage cannula. Of course, cannula engagement members (1197) may include any other suitable geometry as will be apparent to those of ordinary skill in the art in view of the teachings herein.

Figure 6:
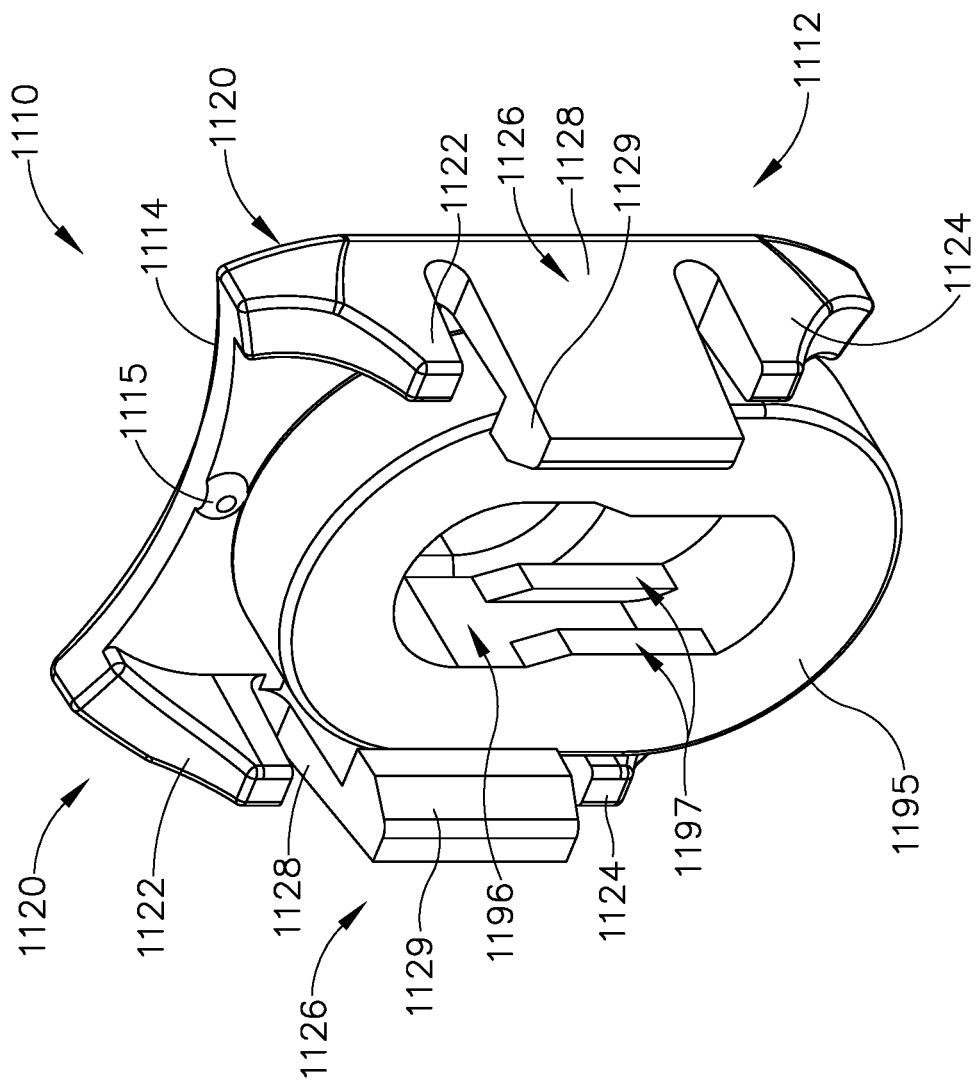
FIG. 6 depicts a perspective view of an exemplary alternative depth stop assembly for use with the biopsy system of FIG. 1.
Figure 9:
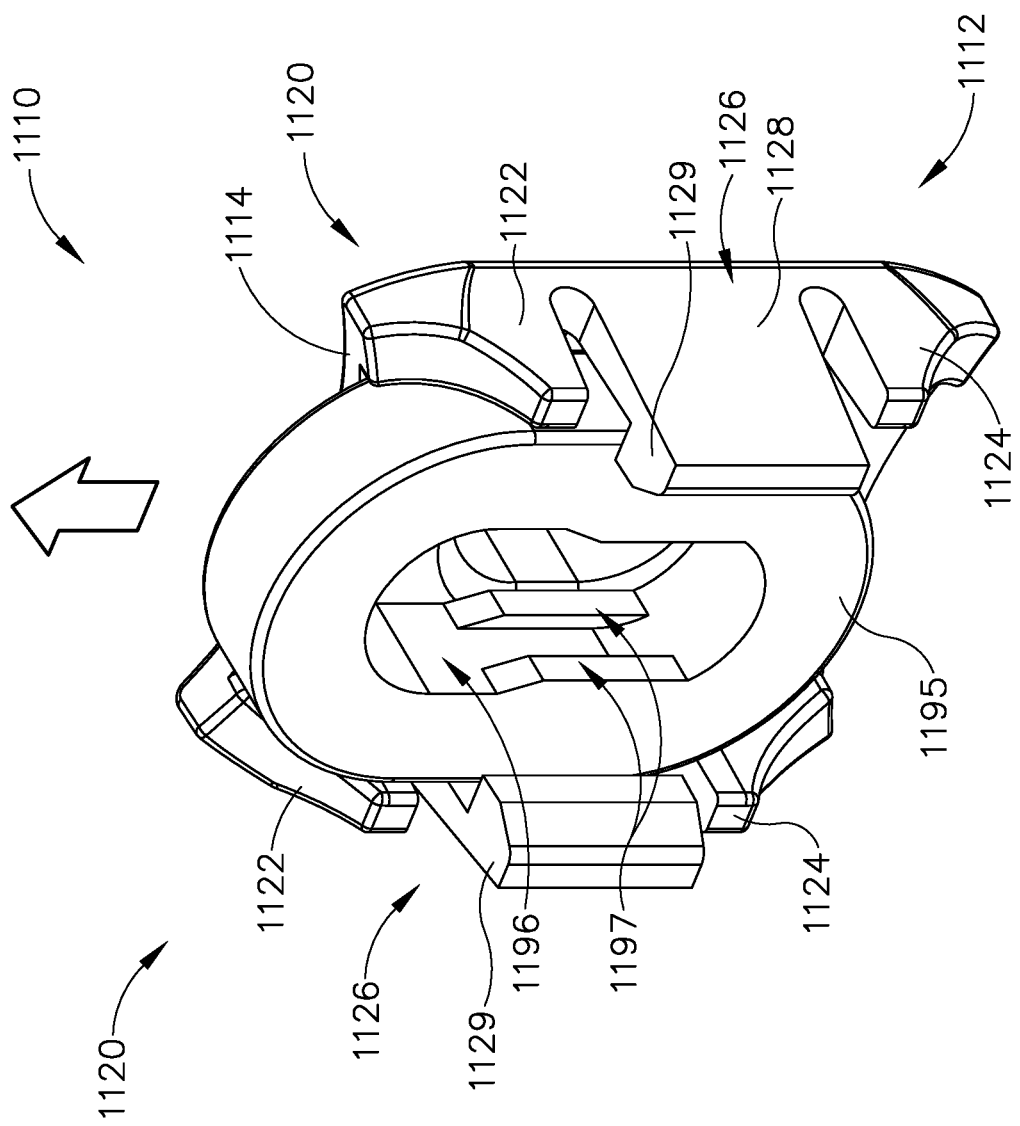
FIG. 9 depicts another perspective view of the depth stop assembly of FIG. 6, with the depth stop assembly in a locked position.
Figure 10:
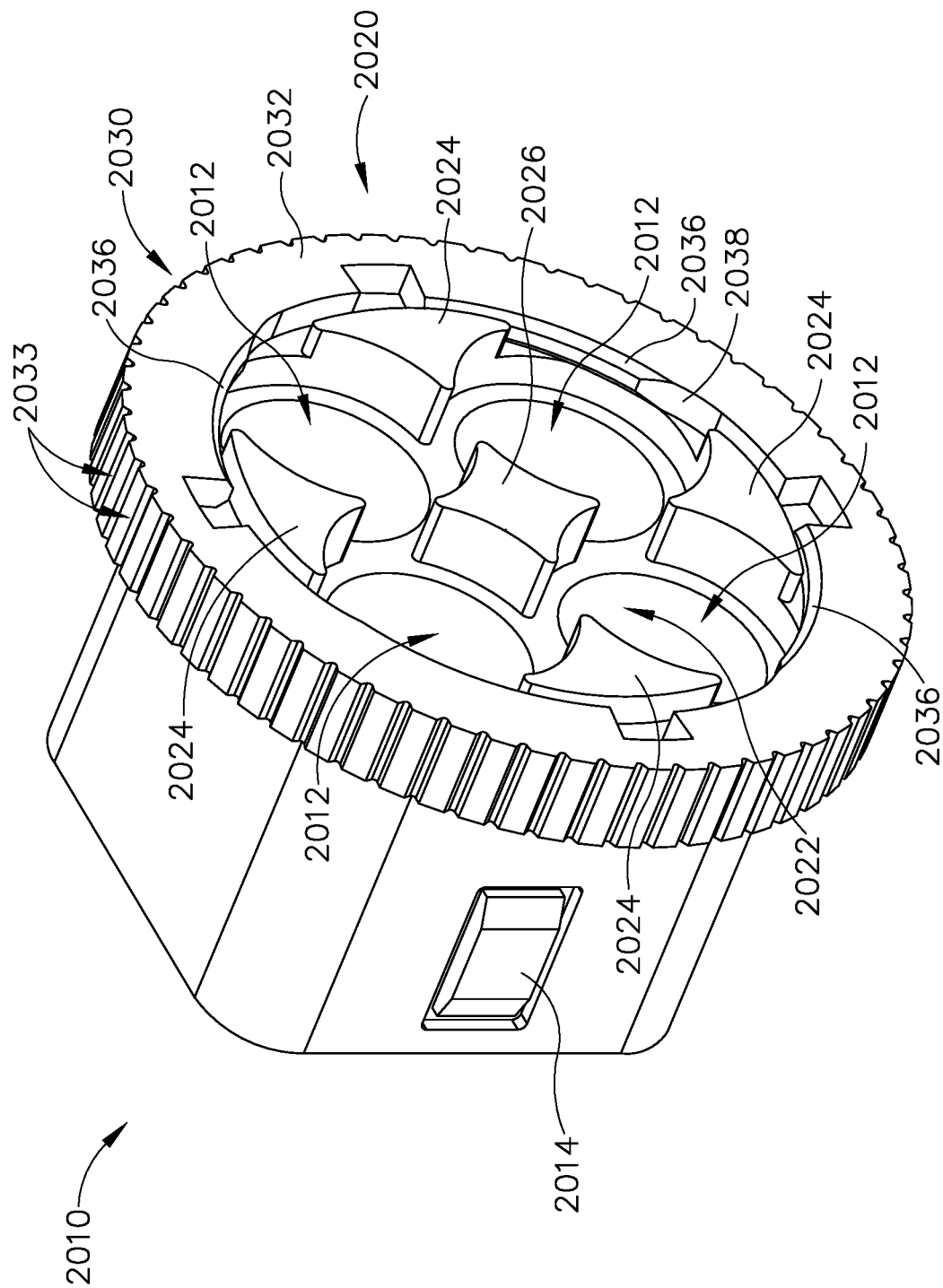
FIG. 10 depicts a perspective view of an exemplary alternative guide cube for use with the biopsy system of FIG. 1.
Figure 11:
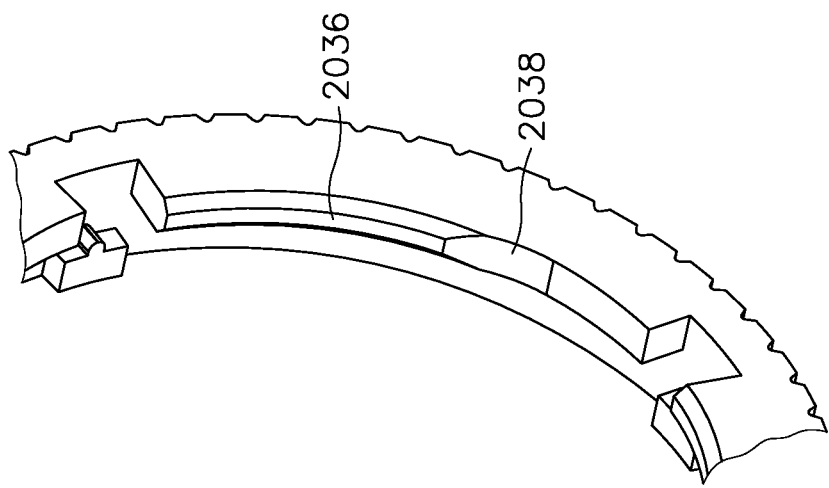
FIG. 11 depicts a detailed perspective view of a rotatable hub of the guide cube of FIG. 10.

An exemplary use of depth stop assembly (1110) can be seen by comparing FIGS. 6 and 9. In particular, FIG. 6 shows depth stop assembly (1110) in an initial position. In the initial position, depth stop device (1195) is in an unlocked position such that the cannula and obturator may be received within depth stop assembly (1110). In particular, depth stop device (1195) is disposed within depth stop holder (1112) by lock arms (1126) via engagement between the proximal face of depth stop device and teeth (1129). Depth stop device (1195) is further positioned in a downward position such that detent feature (1115) selectively prevents upward movement of depth stop device (1195). To maintain alignment between opening (1116) of depth stop holder (1112) and opening (1196) of depth stop device (1195), lower stop members (1124) engage with the bottom geometry of depth stop device (1195).

To transition depth stop device (1195) to a locked position (e.g., once the cannula and/or obturator is inserted into openings (1116, 1196)), an operator may pull depth stop device (1195) laterally upwardly relative to depth stop holder (1112) and relative to cannula to the position shown in FIG. 9. As depth stop device (1195) moves upwardly, cannula engagement members (1197) correspondingly move upwardly relative to opening (1116) of depth stop holder (1112). This upward movement permits cannula engagement members (1197) to engage with the cannula when inserted in openings (1116, 1196) therein. Although not shown, it should be understood that detent feature (1115) may engage with the upper portion of opening (1196) of depth stop device (1195) to selectively maintain depth stop device (1195) in the locked position. However, additional upward movement of depth stop device (1195) beyond the locked position is restricted by upper stop members (1122). Accordingly, lateral movement of depth stop device (1195) is restricted between the predetermined ranges of motion described above. Although the predetermined range of motion of the present example corresponds approximately to the locked and unlocked positions of depth stop device (1195), no such limitation is intended. For instance, in other examples the predetermined range of motion defined by stop members (1122, 1124) may include any suitable range of motion as will be apparent to those of ordinary skill in the art in view of the teachings herein.

It should be understood from the foregoing that when depth stop assembly (1110) is secured to cannula in the locked configuration such that the longitudinal position of depth stop assembly (1110) is locked in place along the length of cannula, depth stop assembly (1110) will restrict the depth to which cannula and obturator may be inserted into guide cube. In particular, depth stop assembly (1110) will engage the proximal face of guide cube and thereby arrest further insertion of cannula and obturator into guide cube.

As a variation of the localization fixture discussed above, another embodiment of the localization fixture may be arranged to prevent backing-out of guide cube relative to grid plate. Additionally, it may be desirable to lock a depth stop device similar to depth stop devices (1095, 1195) described above, to guide cube. Various examples of how guide cube may be reconfigured to prevent backing-out of guide cube relative to grid plate and/or to permit attachment between guide cube and the depth stop device will be described in greater detail in the following text. Other examples will be apparent to those of ordinary skill in the art according to the teachings herein. It should be understood that the guide cube examples described below may function substantially similar to guide cube described above. In particular, the guide cube examples described below may be inserted into grid plate and used to guide a cannula and obturator into a patient's breast; to support an inserted cannula and obturator; and to support a biopsy device (200 and 300). It should be understood that the guide device examples discussed below may be used with any of the biopsy devices (200 and 300) discussed herein.

FIGS. 10-15 show an exemplary alternative guide cube (2010) that may be used in conjunction with targeting set described above, in place of guide cube. Guide cube (2010) is similar to guide cubes described above and in the cited references. However, unlike guide cubes described above and in the cited references, guide cube (2010) includes four corner holes (2012), a grid engagement member (2014), and a depth stop coupling assembly (2020). Holes (2012) are disposed in each corner of guide cube (2010) and extend through guide cube (2010) from the distal face of guide cube (2010) to the proximal face. Similarly to holes described in references, holes (2012) of the present example are configured to receive cannula and obturator to guide cannula and obturator relative to grid plate when guide cube (2010) is inserted into grid plate.

Grid engagement member (2014) is disposed on at least one side of guide cube (2010). Grid engagement member (2014) is generally positioned and configured to engage with grid plate when guide cube (2010) is inserted into grid plate. In particular, grid engagement member (2014) of the present example comprises a relatively resilient yet elastic material. When guide cube (2010) is inserted into grid plate grid engagement member (2014) will bear against the wall of a given square recess (130) of grid plate, thereby creating a compression fit between guide cube (2010) and grid plate. Grid engagement member (2014) of the present example comprises any suitable material, qualified for medical device use, such as rubber, silicone, polyether block amide (PEBA), and/or any other suitable material as will be apparent to those of ordinary skill in the art in view of the teachings herein.

Depth stop coupling assembly (2020) is generally configured to receive a depth stop assembly similar to depth stop assemblies (1010, 1110) described above. By way of example only, the present example is described herein as being usable in conjunction with depth stop assembly (1010) described above, although any other suitable depth stop assembly may be used. Once depth stop assembly (1010) is received within depth stop coupling assembly (2020), depth stop coupling assembly (2020) is further configured to selectively lock depth stop coupling assembly (2020) to guide cube (2010).

Depth stop coupling assembly (2020) comprises a plurality of indexing features (2022) and a rotatable lock feature (2030). Indexing features (2022) extend proximally from guide cube (2010) and comprise a plurality of outer index members (2024) and a single inner index member (2026). Indexing features (2022) are generally configured to cooperatively direct a portion of depth stop assembly (1010) into position relative to guide cube (2010). In particular, each indexing feature (2022) has a particular geometry corresponding to the cylindrical shape of cube coupling member (1018) of depth stop assembly (1010). As will be described in greater detail below, the geometry of each indexing feature (2022) is also configured to provide support to cube coupling member (1018) as it is lockingly engaged by depth stop coupling assembly (2020).

Lock feature (2030) of depth stop coupling assembly (2020) is generally configured to rotate relative to guide cube (2010) to selectively lock depth stop assembly (1010) to guide cube (2010). In particular, lock feature (2030) includes a rotatable hub (2032). The exterior of rotatable hub (2032) comprises a plurality of grip features (2033) that are configured to enhance the gripability of rotatable hub (2032).

Rotatable hub (2032) defines an opening (2034), which encompasses all holes (2012) of guide cube (2010). The interior of hub (2032) includes a lock protrusion (2036) extending inwardly into opening (2034). As can best be seen in FIG. 11, lock protrusion (2036) has a generally rounded or chamfered cross-sectional shape. As will be understood, this cross-sectional shape generally corresponds to the cross-sectional shape of connector channel (1019) of depth stop assembly (1010) such that locking protrusion (2036) and connector channel (1019) are complementary in shape. Lock protrusion (2036) further includes a ramp portion (2038). As will be described in greater detail below, ramp portion (2038) is generally configured to enhance the ability of locking protrusion (2036) to couple with connector channel (1019).

Rotatable hub (2032) of the present example comprises four discrete locking protrusions (2036). As can best be seen in FIG. 12, each protrusion is positioned an equal distance around the circumference of rotatable hub (2032). It should be understood that each protrusion (2036) is positioned to correspond to a given hole (2012) of guide cube (2010). As will be described in greater detail below, rotatable hub (2032) is configured to rotate to align a given lock protrusion (2036) with a corresponding hole (2012) to selectively lock depth stop assembly (1010) with guide cube (2010).

Figure 12:
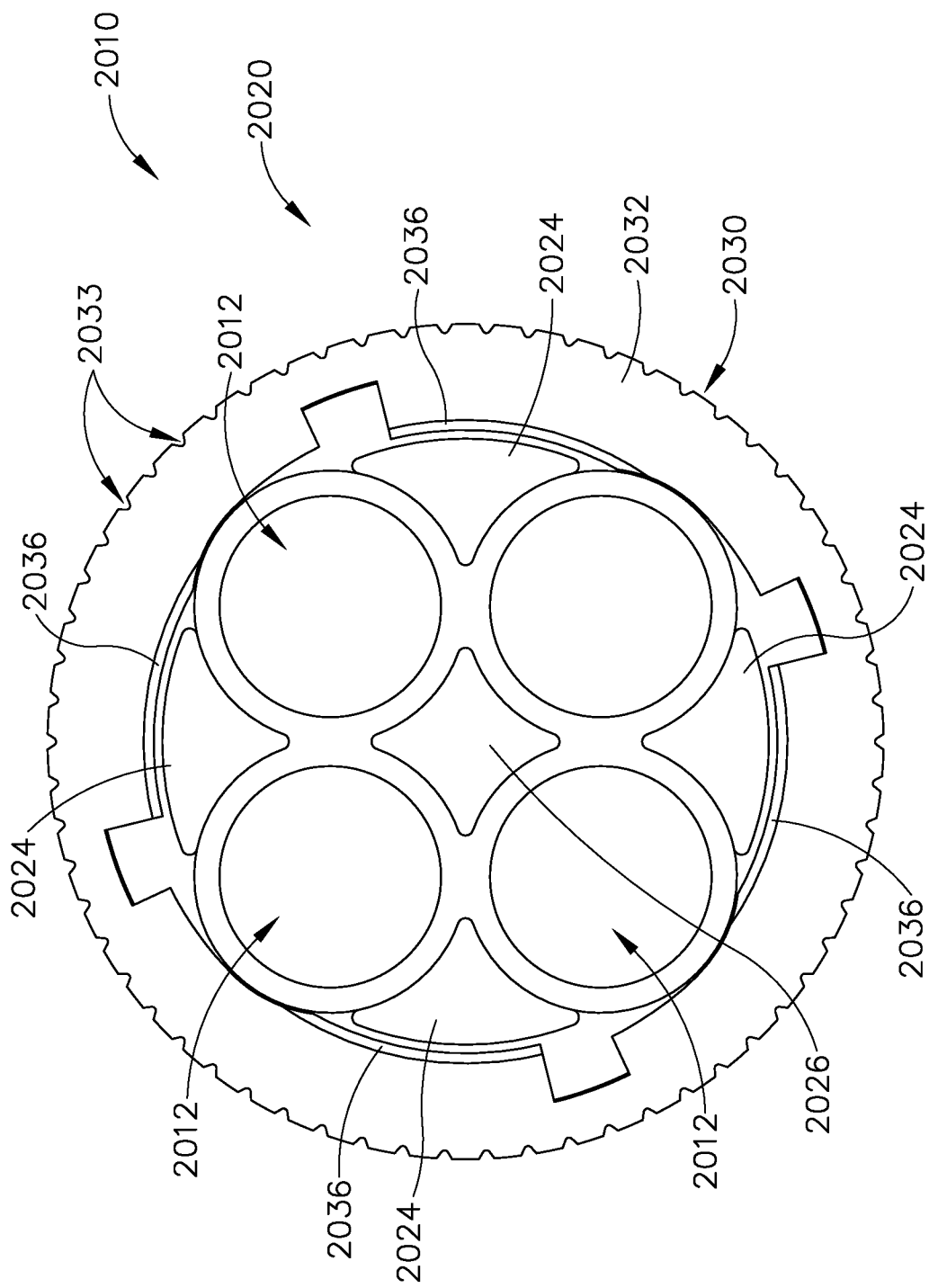
FIG. 12 depicts a front elevational view of the guide cube of FIG. 10, with the guide cube in an unlocked position.
Figure 13:
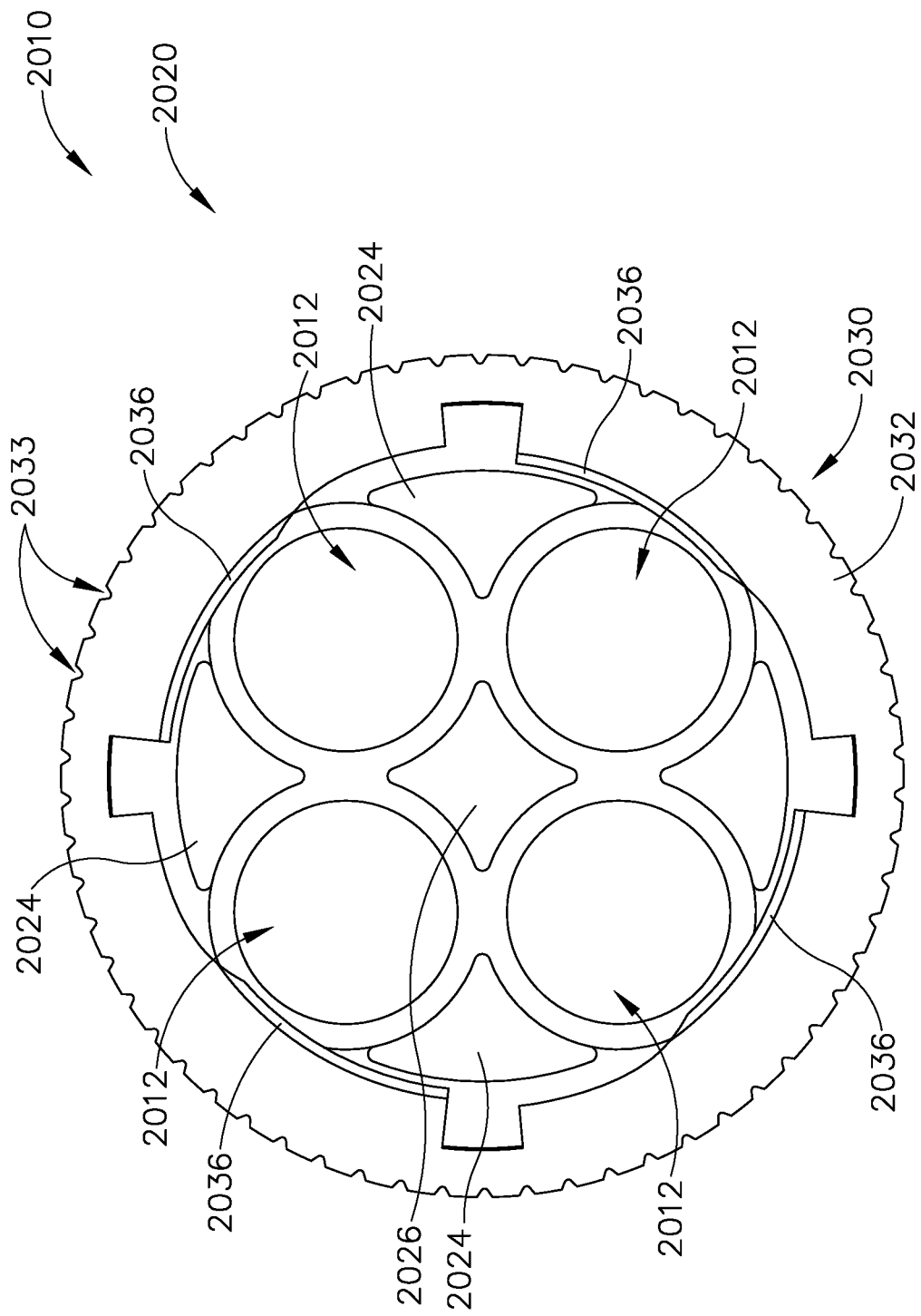
FIG. 13 depicts another front elevational view of the guide cube of FIG. 10, with the guide cube in a locked position.
Figure 14:
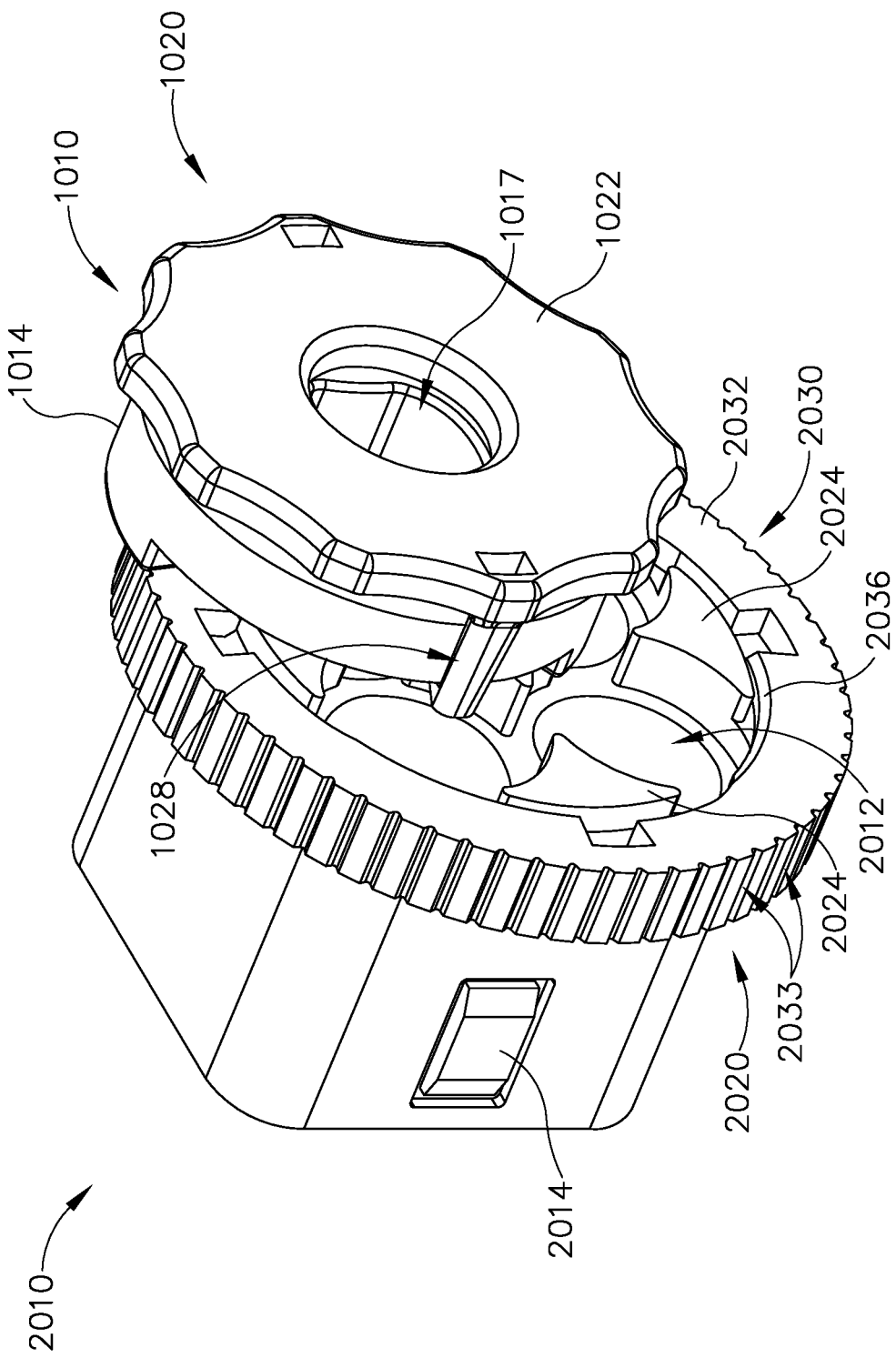
FIG. 14 depicts a perspective view of the guide cube of FIG. 10, with the depth stop assembly of FIG. 3 inserted into the guide cube and the guide cube in the unlocked position.

FIGS. 12-15 show an exemplary use of lock feature (2030) to selectively lock depth stop assembly (1010) to guide cube (2010). Although the use of lock feature (2030) is described herein as being in conjunction with depth stop assembly (1010), it should be understood that depth stop assembly (1110) or any other suitable depth stop assembly described herein may be similarly used with lock feature (2030). As best seen in FIG. 12, lock feature (2030) may initially be positioned in an unlocked position. In the unlocked position, each lock protrusion (2036) of rotatable hub (2032) is positioned away from each respective hole (2012) of guide cube (2010). Accordingly, in the unlocked position, guide cube (2010) is configured to receive depth stop assembly (1010) as shown in FIG. 14. Although not shown, it should be understood that depth stop assembly (1010) may also be inserted into guide cube (2010) along with cannula and/or obturator. Alternatively, depth stop assembly (1010) may first be inserted into guide cube (2010) with cannula and/or obturator being inserted at a later stage.

Figure 15:
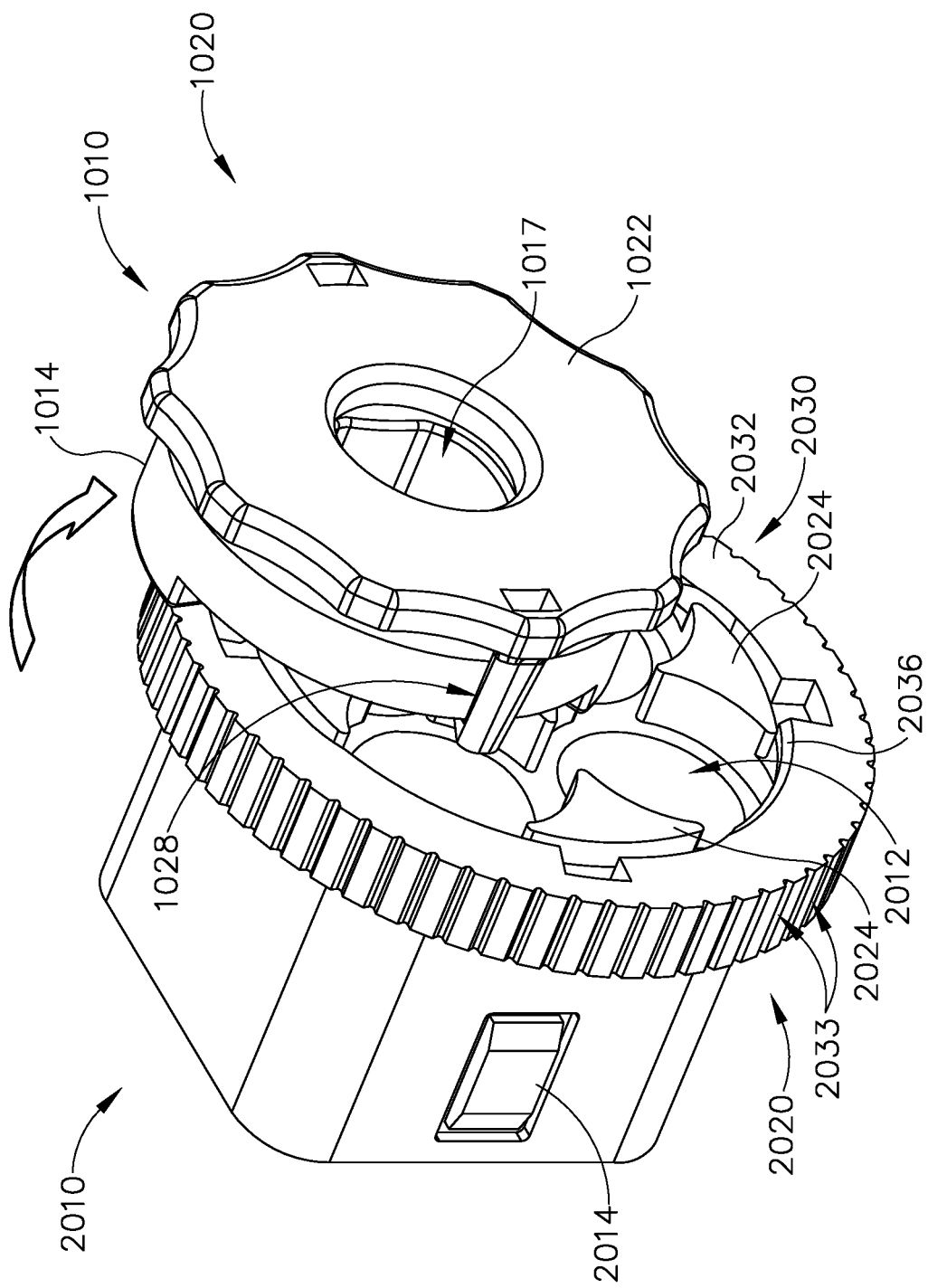
FIG. 15 depicts another perspective view of the guide cube of FIG. 10, with the depth stop assembly of FIG. 3 inserted into the guide cube and the guide cube in the locked position.
Figure 16:
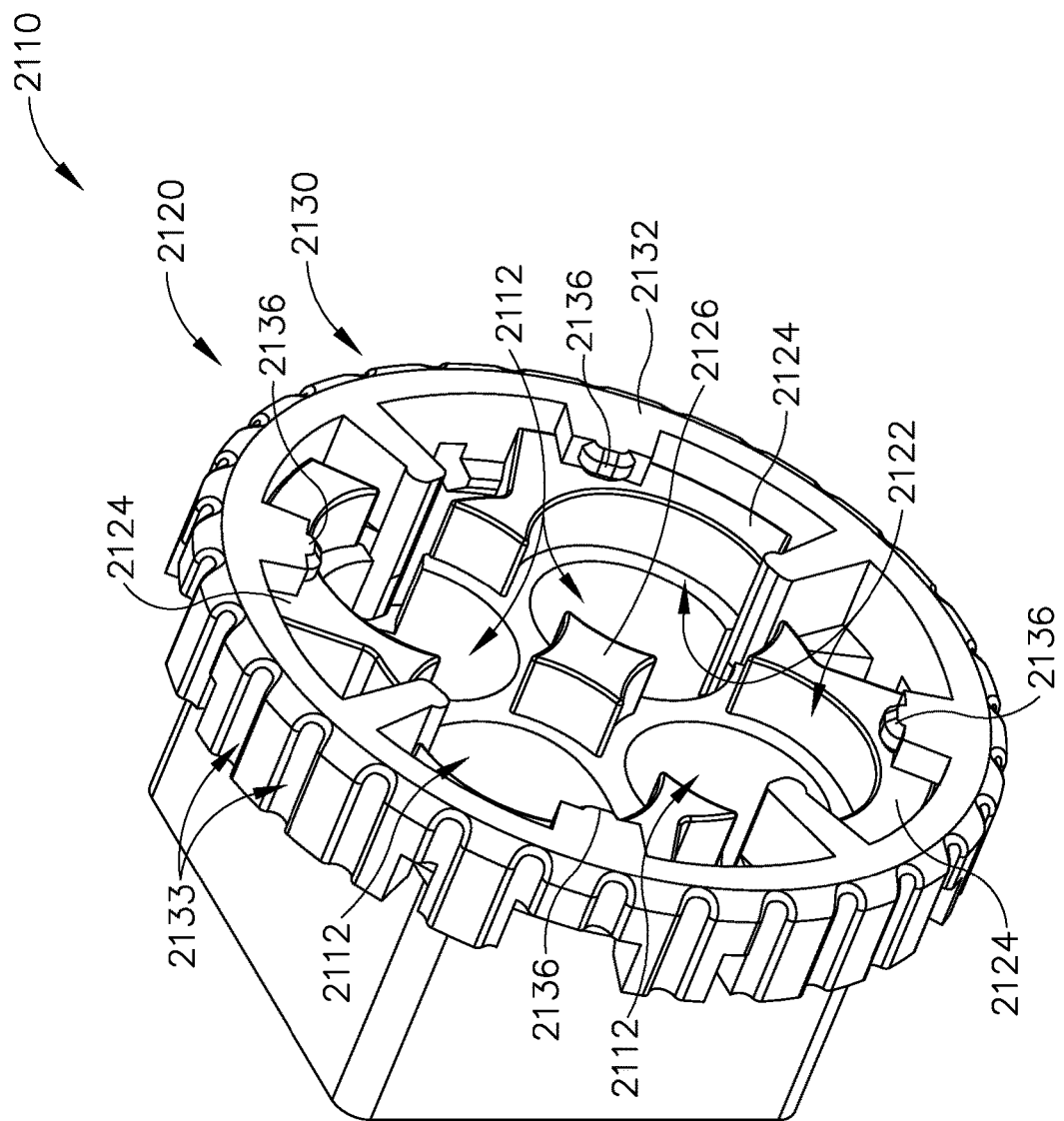
FIG. 16 depicts a perspective view of another exemplary alternative guide cube for use with the biopsy system of FIG. 1.
Figure 17:
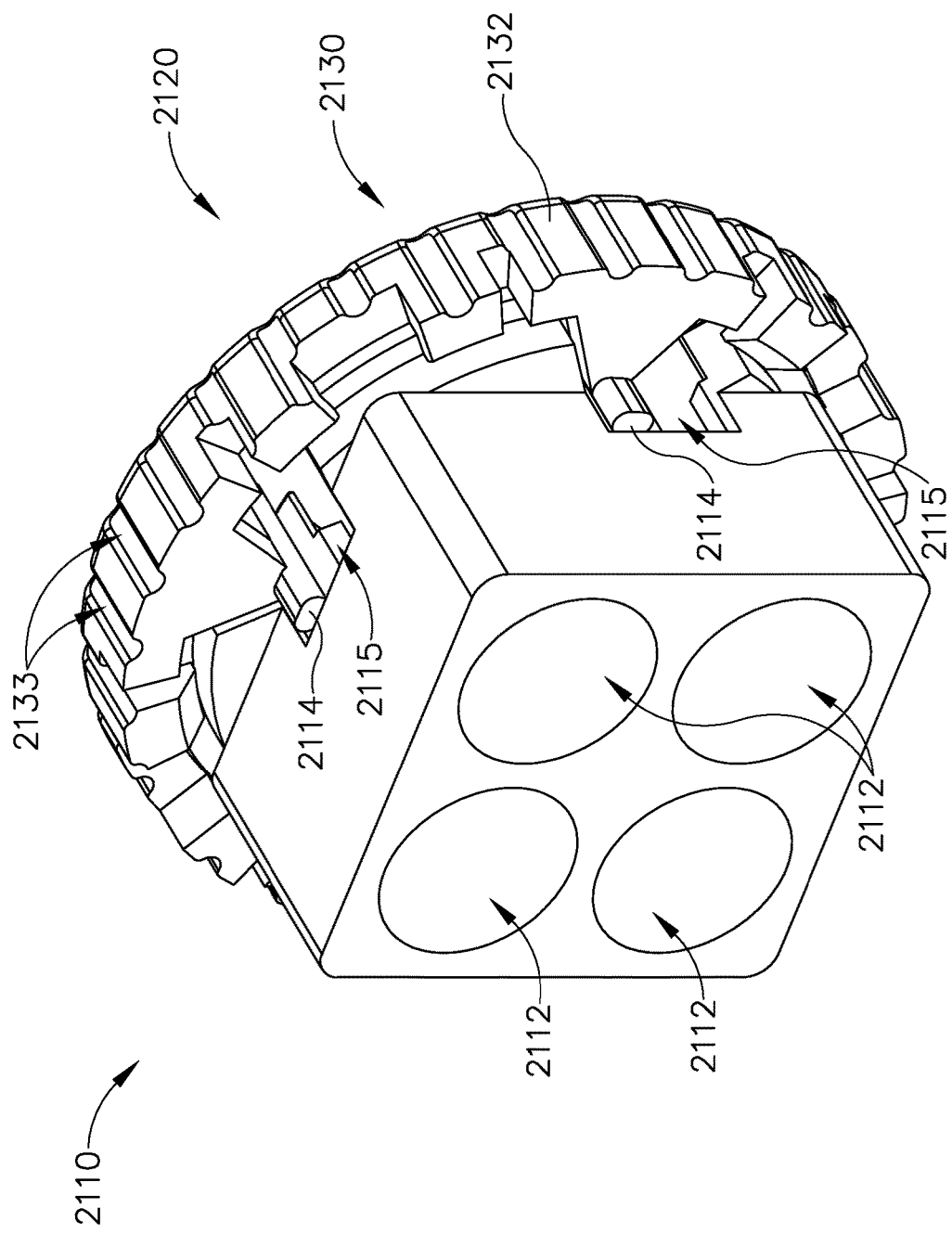
FIG. 17 depicts another perspective view of the guide cube of FIG. 16.

Once depth stop assembly (1010) is inserted into guide cube (2010), depth stop assembly (1010) may be locked into position via rotatable hub (2032). It should be understood that although depth stop assembly (1010) is shown as being positioned adjacent to a given hole (2012), depth stop assembly (1010) may alternatively positioned adjacent to any hole (2012) of guide cube (2010). To lock depth stop assembly (1010) into position, an operator may rotate rotatable hub (2032) in the clockwise direction as shown in FIG. 15. As rotatable hub (2032) is rotated to the position shown in FIG. 15, a corresponding lock protrusion (2036) will move toward the position shown in FIG. 13. Although not shown, it should be understood that once lock protrusion (2036) is oriented in the position shown in FIG. 13, lock protrusion (2036) will be engaged with connector channel (1019) of depth stop assembly (1010). Such engagement will generally secure depth stop assembly (1010) relative to guide cube (2010), thereby generally preventing any longitudinal or lateral movement relative to guide cube (2010). Once locked in position, depth stop assembly (1010) may then be used to position and secure cannula and obturator as described above.

FIGS. 16-23 show another exemplary alternative guide cube (2110) that may be used in conjunction with targeting set described above, in place of guide cube. Guide cube (2110) is similar to guide cube (2010) described above. For instance, like guide cube (2010), guide cube (2110) of the present example includes four corner holes (2112), and a depth stop coupling assembly (2120). However, unlike guide cube (2010), guide cube (2110) incorporates a plurality of grid engagement members (2114) into depth stop coupling assembly (2120) as will be described in greater detail below. Holes (2112) are disposed in each corner of guide cube (2110) and extend through guide cube (2110) from the distal face of guide cube (2110) to the proximal face. Similarly to the holes described above, holes (2112) of the present example are configured to receive cannula and obturator to guide cannula and obturator relative to grid plate when guide cube (2010) is inserted into grid plate.

Depth stop coupling assembly (2120) is generally configured to receive a depth stop assembly similar to depth stop assemblies (1010, 1110) described above. By way of example only, the present example is described herein as being usable in conjunction with depth stop assembly (1010) described above, although any other suitable depth stop assembly may be used. Once depth stop assembly (1010) is received within depth stop coupling assembly (2120), depth stop coupling assembly (2120) is further configured to selectively lock depth stop coupling assembly (2120) to guide cube (2110).

Depth stop coupling assembly (2120) comprises a plurality of indexing feature (2122), grid engagement members (2114), and a rotatable lock feature (2130). Indexing features (2122) extend proximally from guide cube (2110) and comprise a plurality of outer index members (2124) and a single inner index member (2126). Indexing features (2122) are generally configured to cooperatively direct a portion of depth stop assembly (1010) into position relative to guide cube (2110). In particular, each indexing feature (2122) has a particular geometry corresponding to the cylindrical shape of cube coupling member (1018) of depth stop assembly (1010). As will be described in greater detail below, the geometry of each indexing feature (2122) is also configured to provide support to cube coupling member (1018) as it is lockingly engaged by depth stop coupling assembly (2120).

Lock feature (2130) of depth stop coupling assembly (2120) is generally configured to rotate relative to guide cube (2110) to selectively lock depth stop assembly (1010) to guide cube (2110) and lock guide cube (2110) to grid plate. In particular, lock feature (2130) includes a rotatable hub (2132). The exterior of rotatable hub (2132) comprises a plurality of grip features (2133) that are configured to enhance the gripability of rotatable hub (2132).

Rotatable hub (2132) defines an opening (2134), which encompasses all holes (2112) of guide cube (2110). The interior of hub (2132) includes grid engagement members (2114) and a plurality of lock protrusions (2036) extending inwardly into opening (2134). As can best be seen in FIG. 17, each grid engagement member (2114) extends distally from rotatable hub (2132) into a respective opening (2115) in guide cube (2110). Unlike grid engagement member (2114) described above, grid engagement members (2114) are relatively rigid, although some examples exhibit resilient and/or elastic properties. As will be described in greater detail below, grid engagement members (2114) are generally configured to rotate with rotatable hub (2132) from initially being disposed entirely within openings (2115) of guide cube (2110) to being disposed at least partially out of openings (2115). It should be understood that once grid engagement members (2114) are disposed at least partially out of openings (2115), grid engagement members (2114) will engage grid plate, thereby retaining guide cube (2110) within grid plate.

Figure 18:
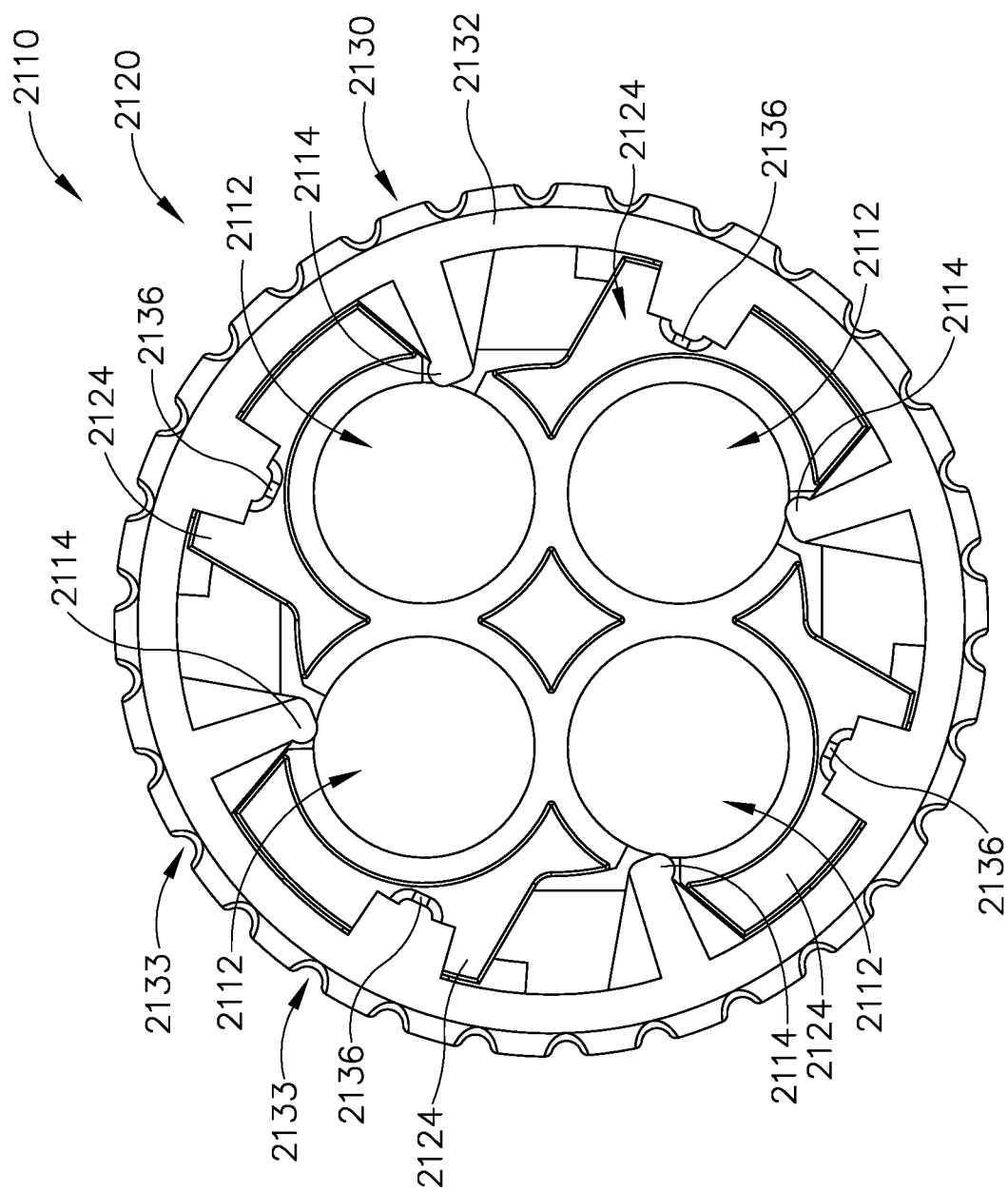
FIG. 18 depicts a front elevational view of the guide cube of FIG. 16, with the guide cube in an unlocked position.
Figure 19:
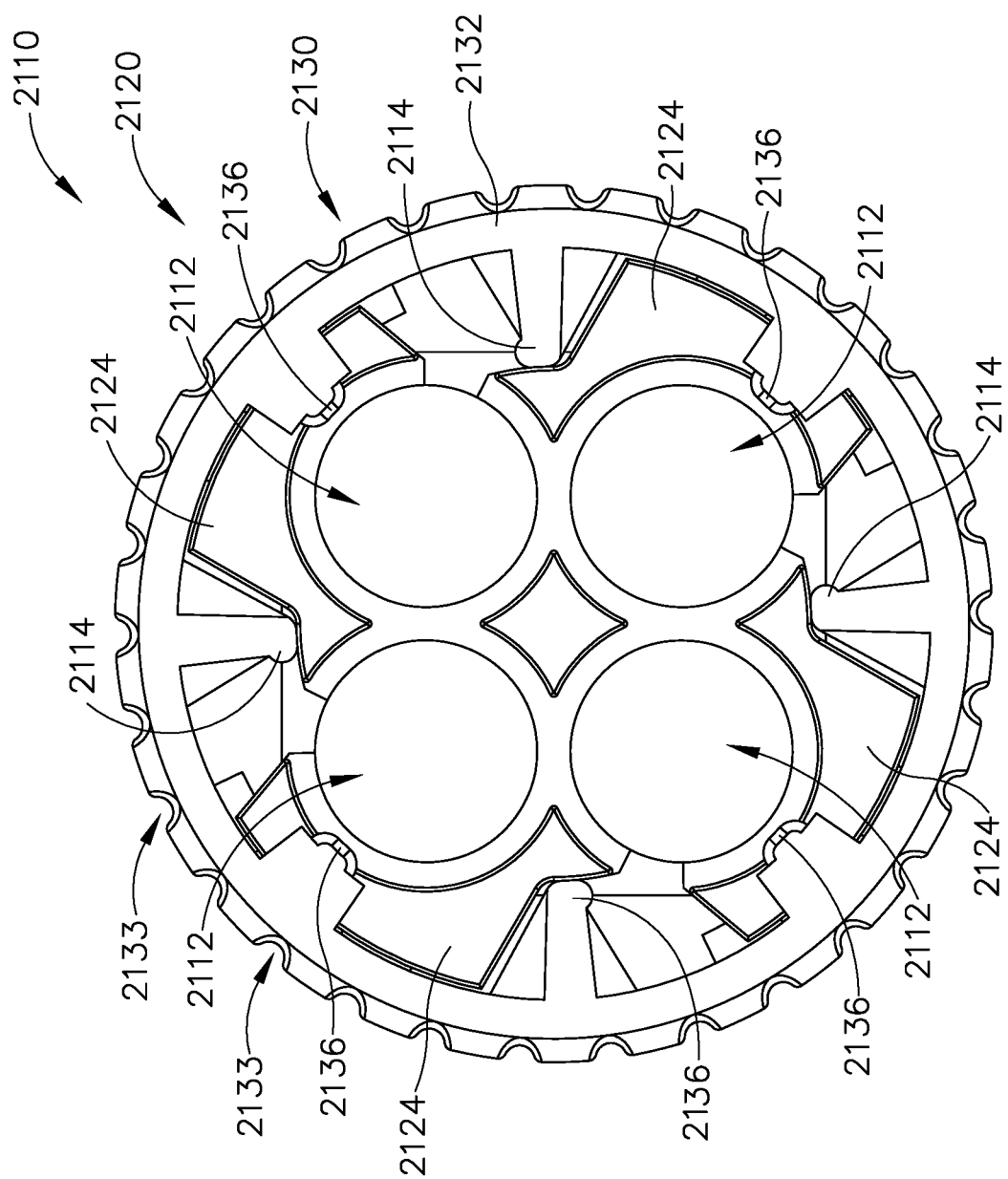
FIG. 19 depicts another front elevational view of the guide cube of FIG. 16, with the guide cube in a locked position.
Figure 20:
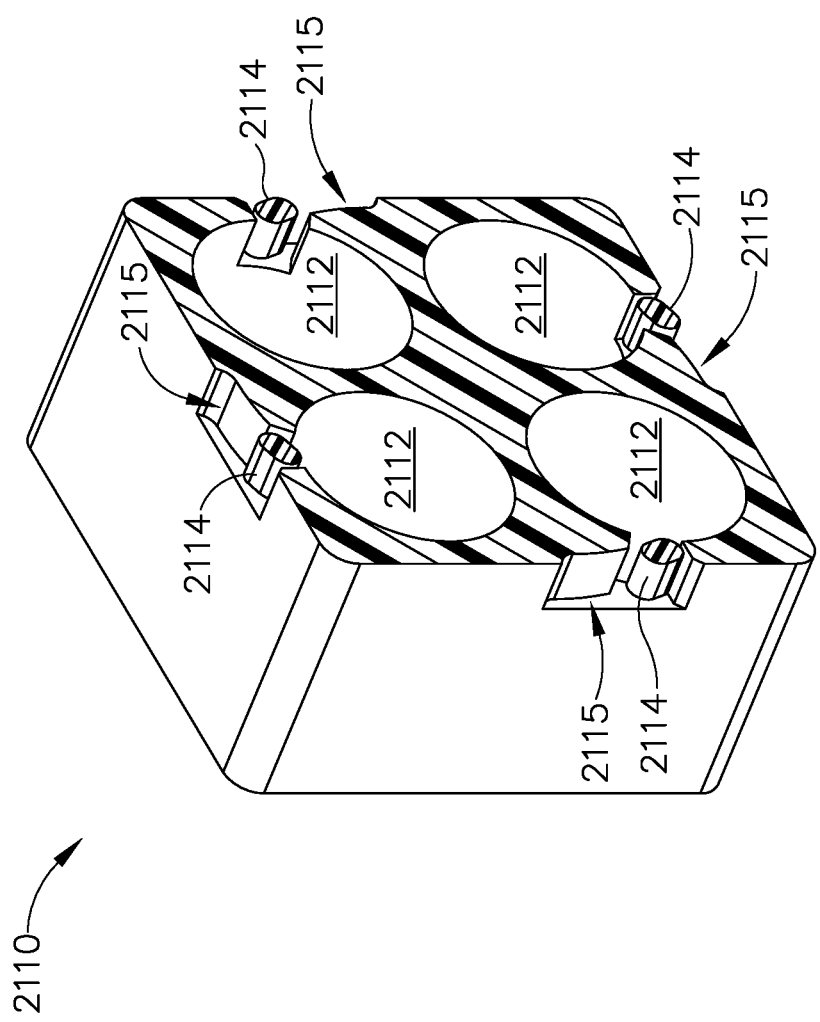
FIG. 20 depicts a perspective cross-sectional view of the guide cube of FIG. 16, with the guide cube in the unlocked position.

As can best be seen in FIG. 18, each lock protrusion (2136) has a generally rounded or chamfered cross-sectional shape, but is less elongate relative to lock protrusion (2036) described above. As will be understood, this cross-sectional shape generally corresponds to the cross-sectional shape of connector channel (1019) of depth stop assembly (1010) such that locking protrusion (2136) and connector channel (1019) are complementary in shape.

Rotatable hub (2132) of the present example comprises four discrete locking protrusions (2136). As can best be seen in FIG. 18, each protrusion is positioned an equal distance around the circumference of rotatable hub (2132). It should be understood that each protrusion (2136) is positioned to correspond to a given hole (2112) of guide cube (2110). As will be described in greater detail below, rotatable hub (2132) is configured to rotate to align a given lock protrusion (2136) with a corresponding hole (2112) to selectively lock depth stop assembly (1010) with guide cube (2110).

Figure 22:
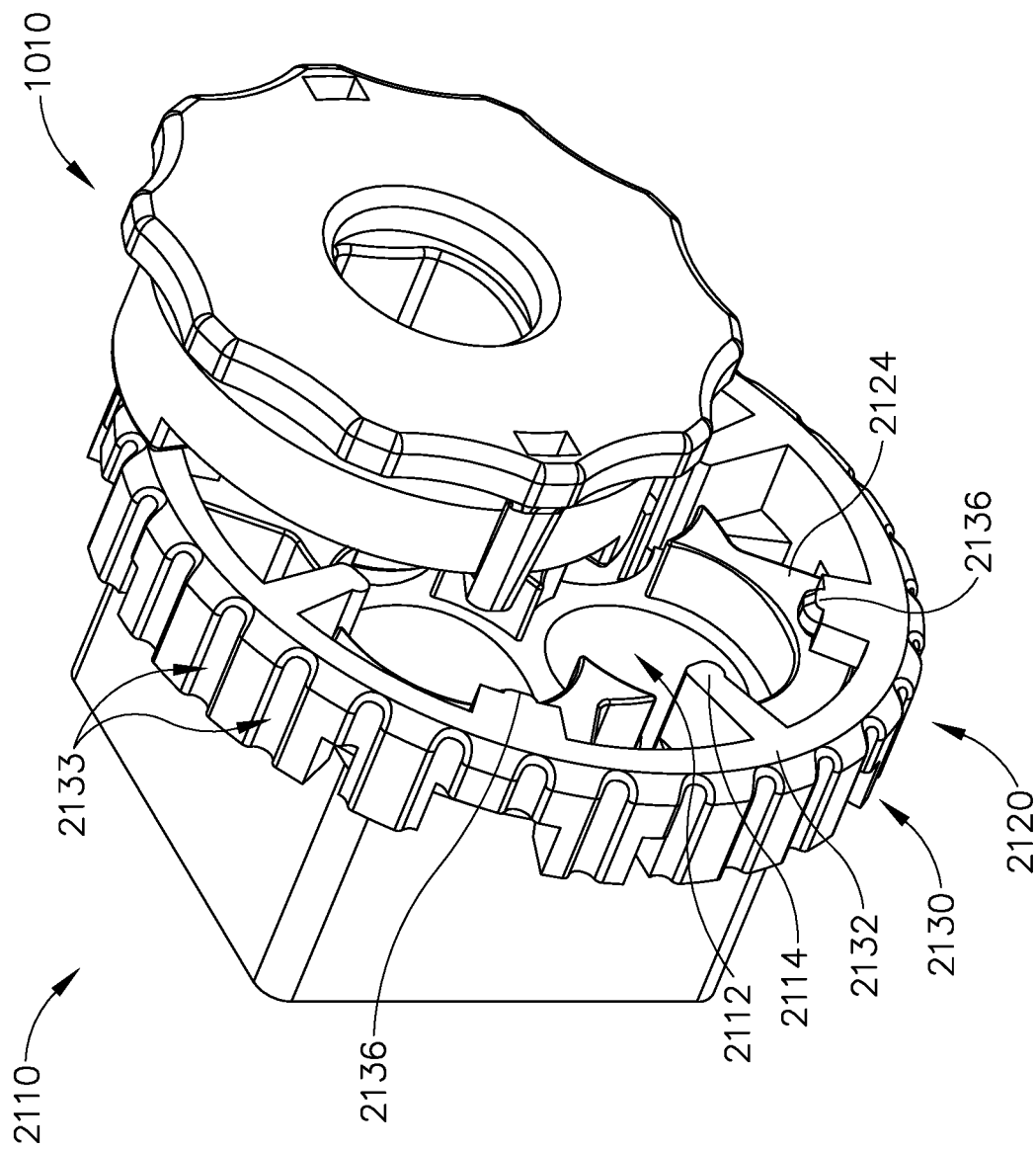
FIG. 22 depicts a perspective view of the guide cube of FIG. 16, with the depth stop assembly of FIG. 3 inserted into the guide cube and the guide cube in the unlocked position.

FIGS. 18-23 show an exemplary use of lock feature (2130) to selectively lock depth stop assembly (1010) to guide cube (2110). Although the use of lock feature (2130)

is described herein as being in conjunction with depth stop assembly (1010), it should be understood that depth stop assembly (1110) or any other suitable depth stop assembly described herein may be similarly used with lock feature (2130). As best seen in FIG. 18, lock feature (2130) may initially be positioned in an unlocked position. In the unlocked position, each lock protrusion (2136) of rotatable hub (2132) is positioned away from each respective hole (2112) of guide cube (2110). Accordingly, in the unlocked position, guide cube (2110) is configured to receive depth stop assembly (1010) as shown in FIG. 22.

Additionally, when lock feature (2130) is positioned in the unlocked position, grid engagement members (2114) are positioned completely within openings (2115) of guide cube (2110) such that grid engagement members (2114) are at least flush with the exterior of guide cube (2110) or below the exterior surface of guide cube (2110). Accordingly, it should be understood that when lock feature (2130) is in the unlocked position, guide cube (2110) is correspondingly configured to be unlocked or otherwise movable relative to grid plate. Although not shown, it should be understood that depth stop assembly (1010) may also be inserted into guide cube (2110) along with cannula and/or obturator. Alternatively, depth stop assembly (1010) may first be inserted into guide cube (2110) with cannula and/or obturator being inserted at a later stage.

Figure 23:
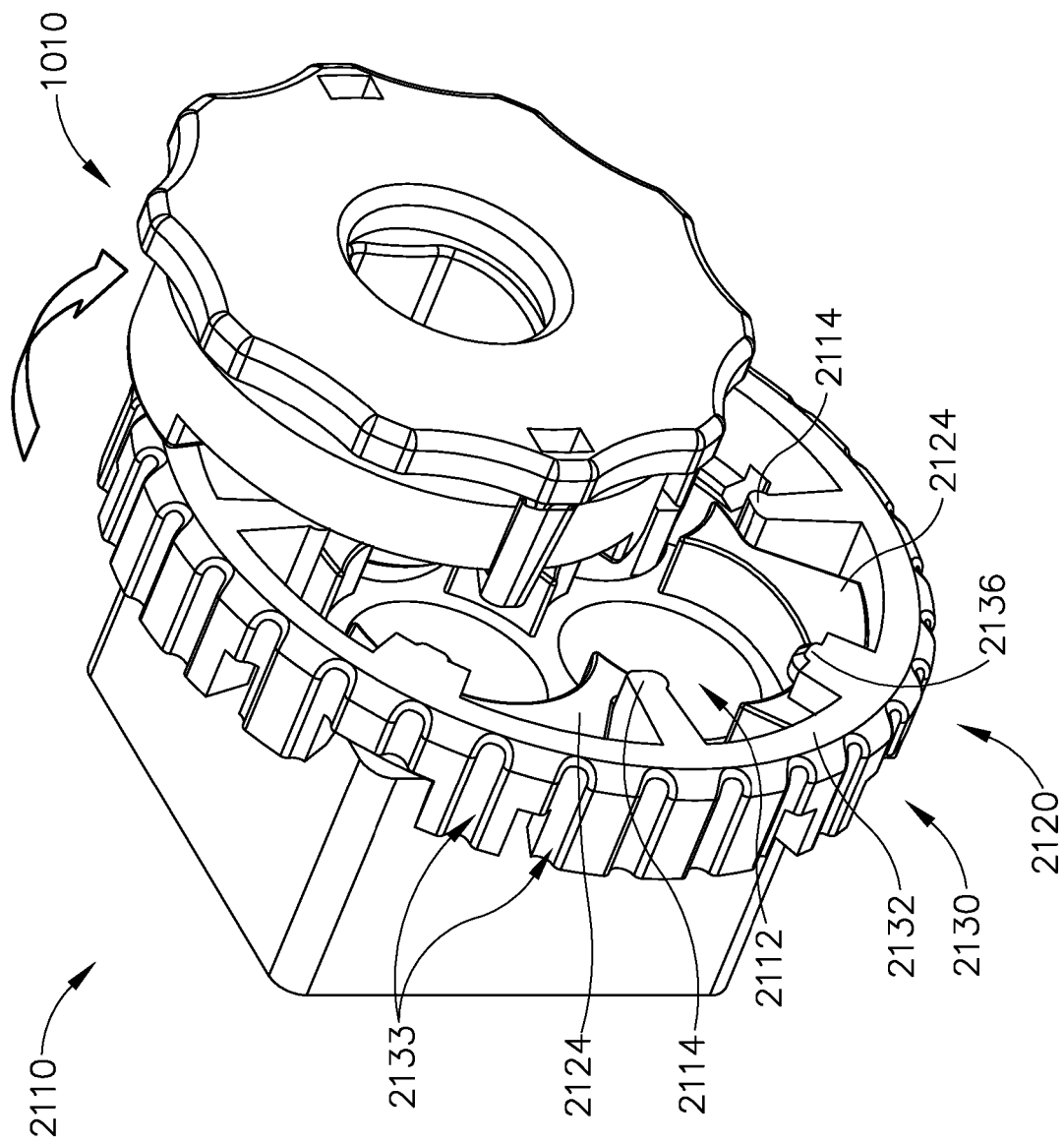
FIG. 23 depicts another perspective view of the guide cube of FIG. 16, with the depth stop assembly of FIG. 3 inserted into the guide cube and the guide cube in the locked position.

Once depth stop assembly (1010) is inserted into guide cube (2110), depth stop assembly (1010) may be locked into position via rotatable hub (2132). It should be understood that although depth stop assembly (1010) is shown as being positioned adjacent to a given hole (2112), depth stop assembly (1010) may alternatively be positioned adjacent to any hole (2112) of guide cube (2110). To lock depth stop assembly (1010) into position, an operator may rotate rotatable hub (2132) in the clockwise direction as shown in FIG. 23. As rotatable hub (2132) is rotated to the position shown in FIG. 23, a corresponding lock protrusion (2136) will move toward the position shown in FIG. 19. Although not shown, it should be understood that once lock protrusion (2136) is oriented in the position shown in FIG. 19, lock protrusion (2136) will be engaged with connector channel (1019) of depth stop assembly (1010). Such engagement will generally secure depth stop assembly (1010) relative to guide cube (2110), thereby generally preventing any longitudinal or lateral movement relative to guide cube (2110).

Figure 21:
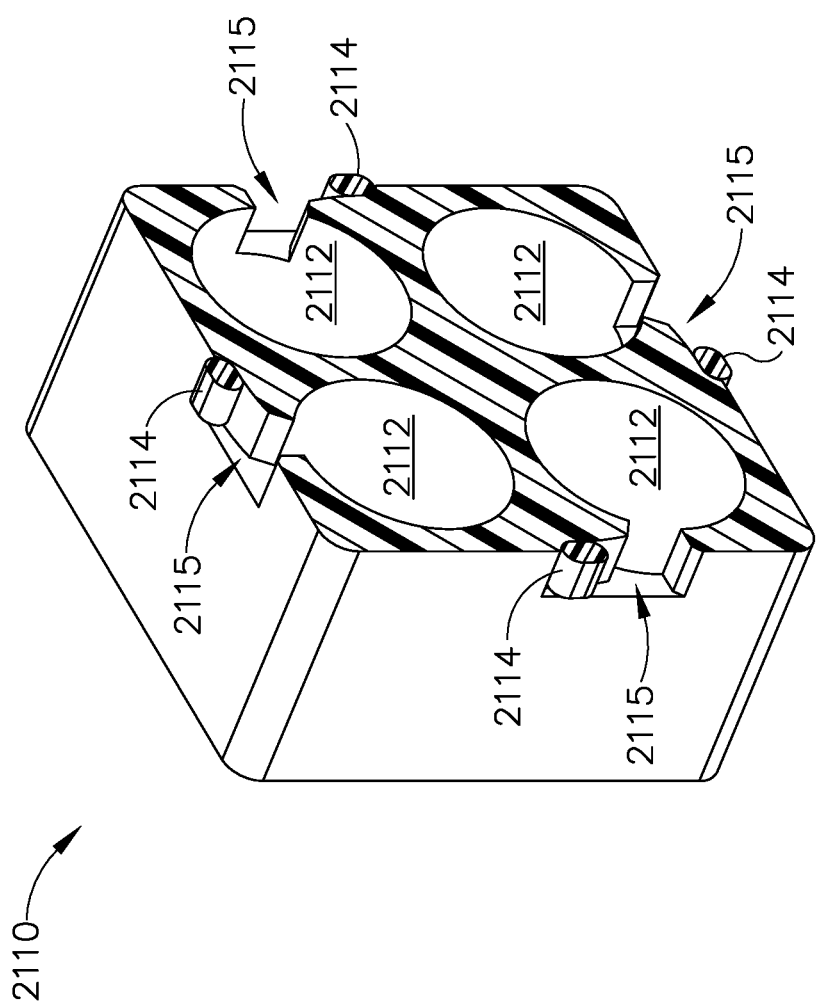
FIG. 21 depicts another perspective cross-sectional view of the guide cube of FIG. 16, with the guide cube in the locked position.

Additionally, clockwise movement of rotatable hub (2132) as shown in FIG. 23 will also cause grid engagement members (2114) to correspondingly rotate to the position shown in FIG. 21. In the position shown in FIG. 21, grid engagement members (2114) are disposed at least partially outside of openings (2115) in guide cube (2110). Once disposed at least partially outside of openings (2115), grid engagement members (2114) will bear against grid plate to secure guide cube (2110) to grid plate. Thus, actuation of rotatable hub (2132) to the locked position simultaneously locks depth stop assembly (1010) to guide cube (2110) and guide cube (2110) to grid plate. Once locked in position, depth stop assembly (1010) may then be used to position and secure cannula and obturator as described above.

Figure 24:
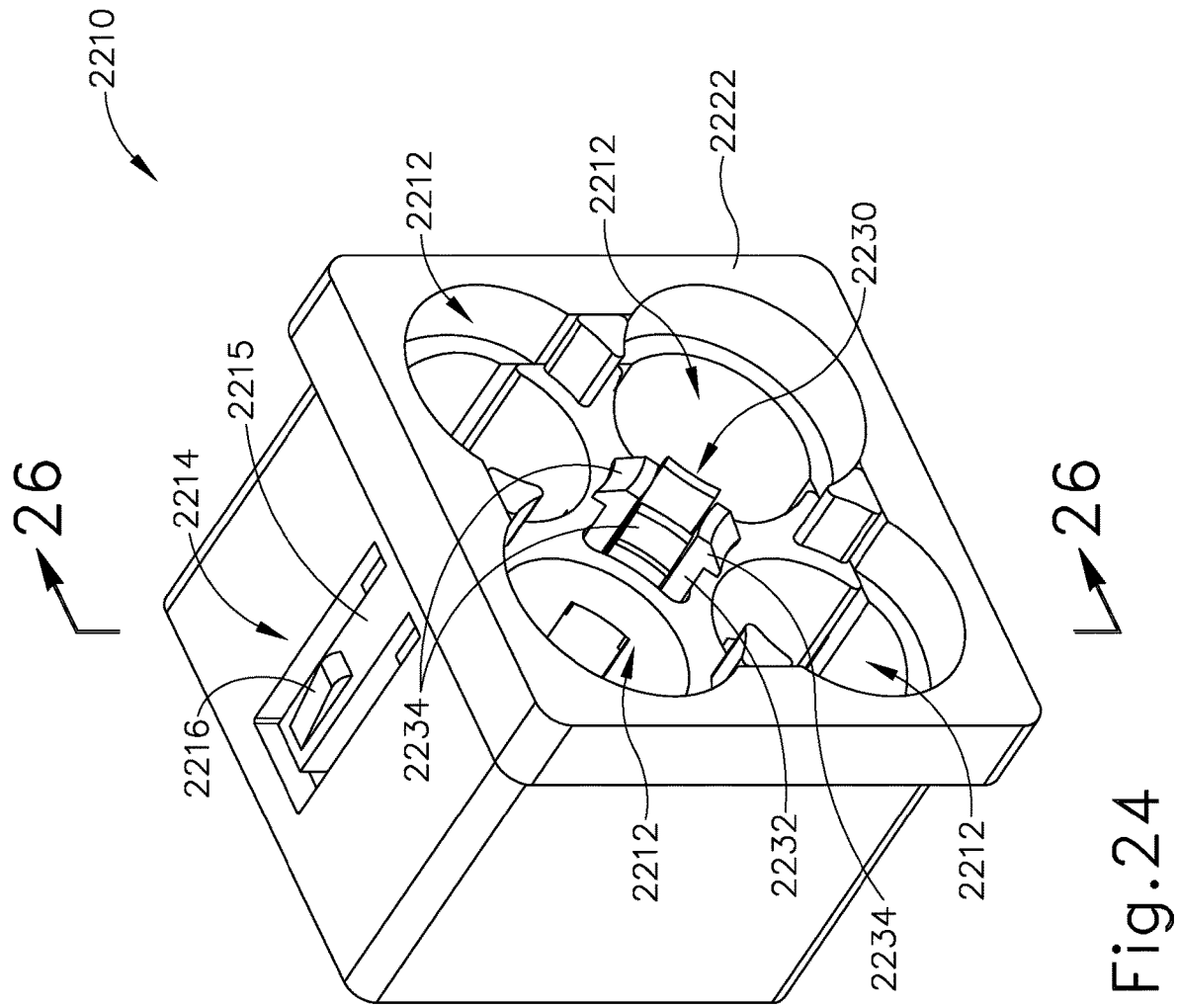
FIG. 24 depicts a perspective view still another exemplary alternative guide cube for use with the biopsy system of FIG. 1.
Figure 25:
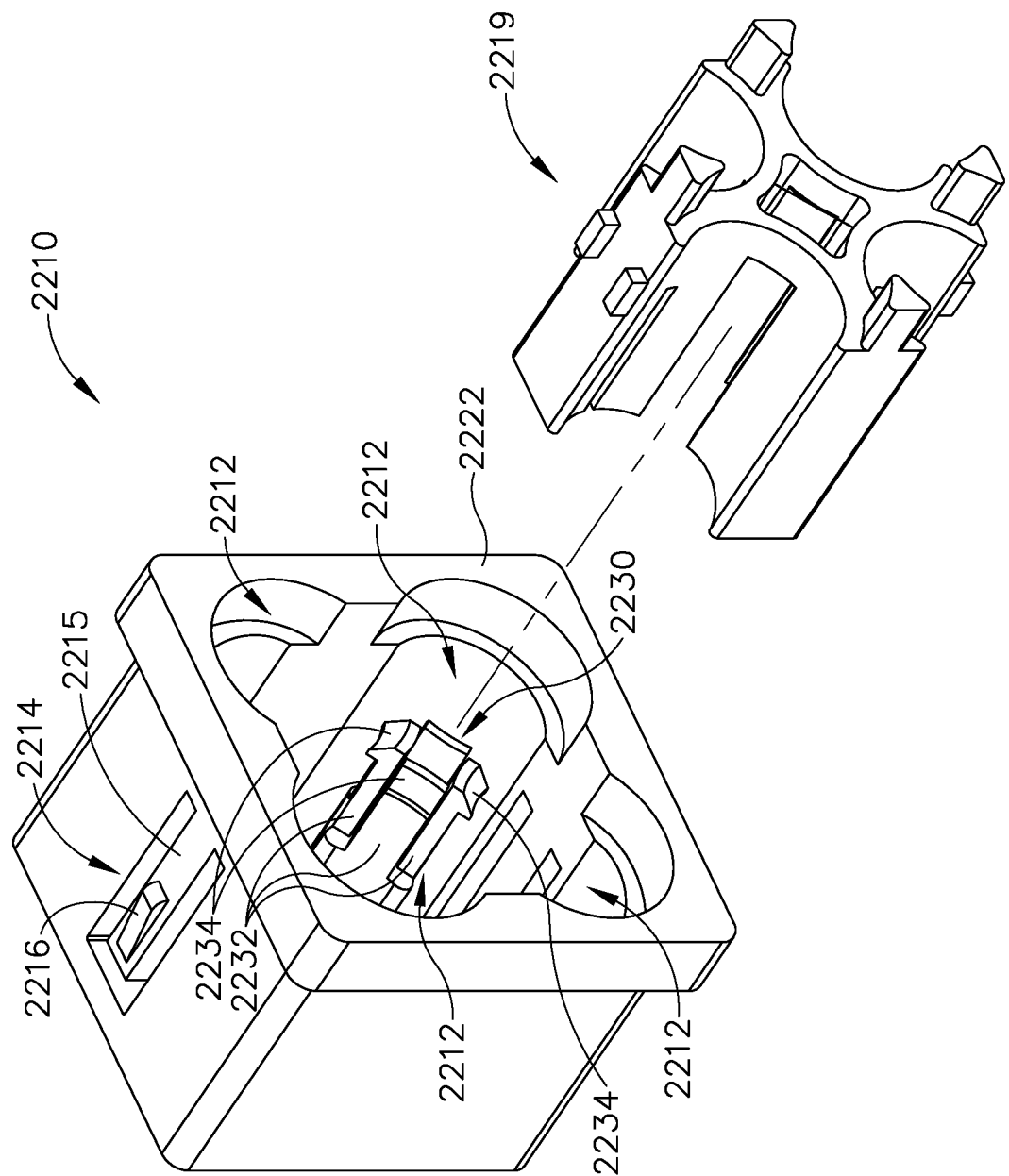
FIG. 25 depicts a perspective exploded view of the guide cube of FIG. 24.
Figure 26:
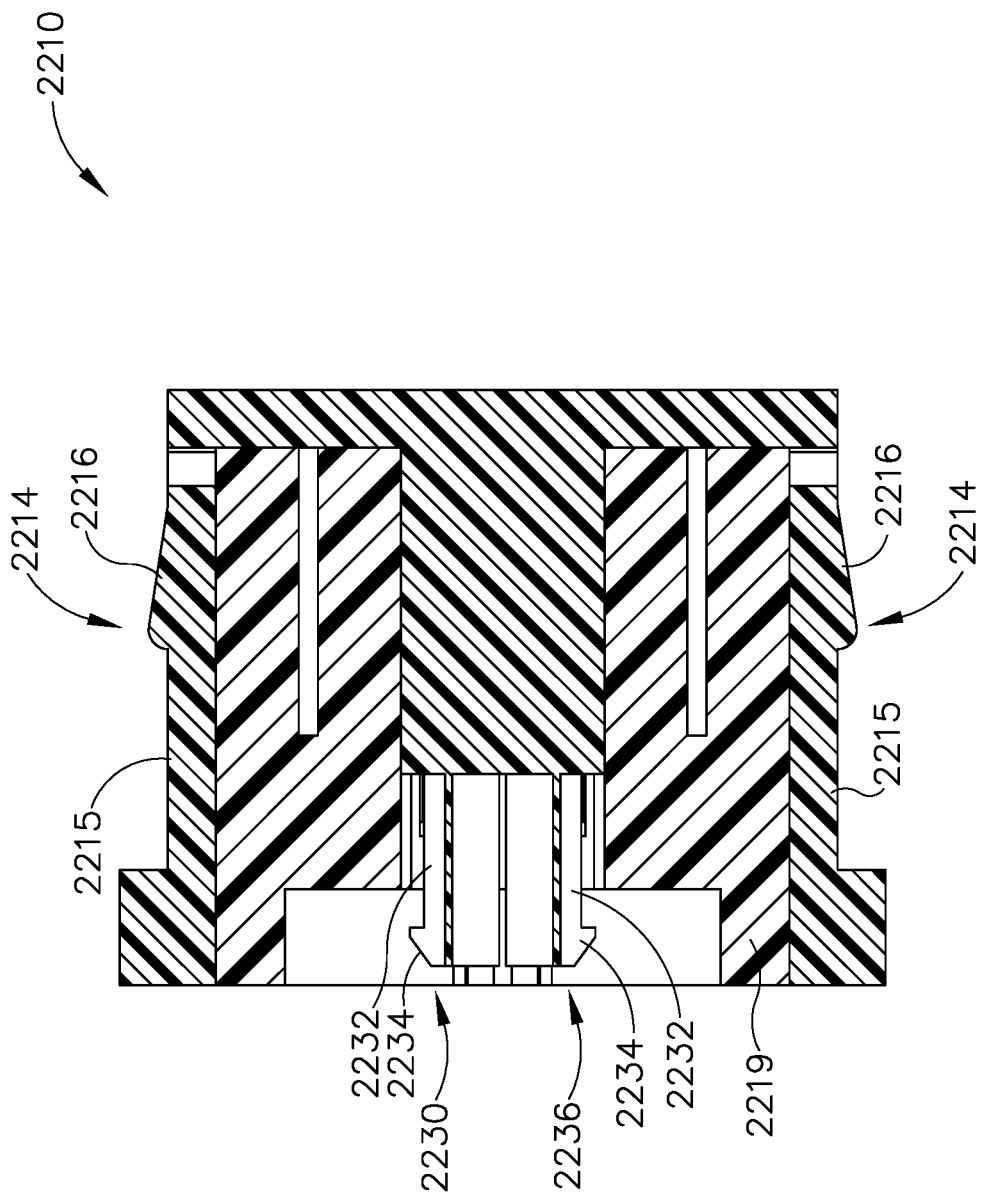
FIG. 26 depicts a side cross-sectional view of the guide cube of FIG. 24, with the cross-section taken along line 26-26 of FIG. 24.
Figure 27:
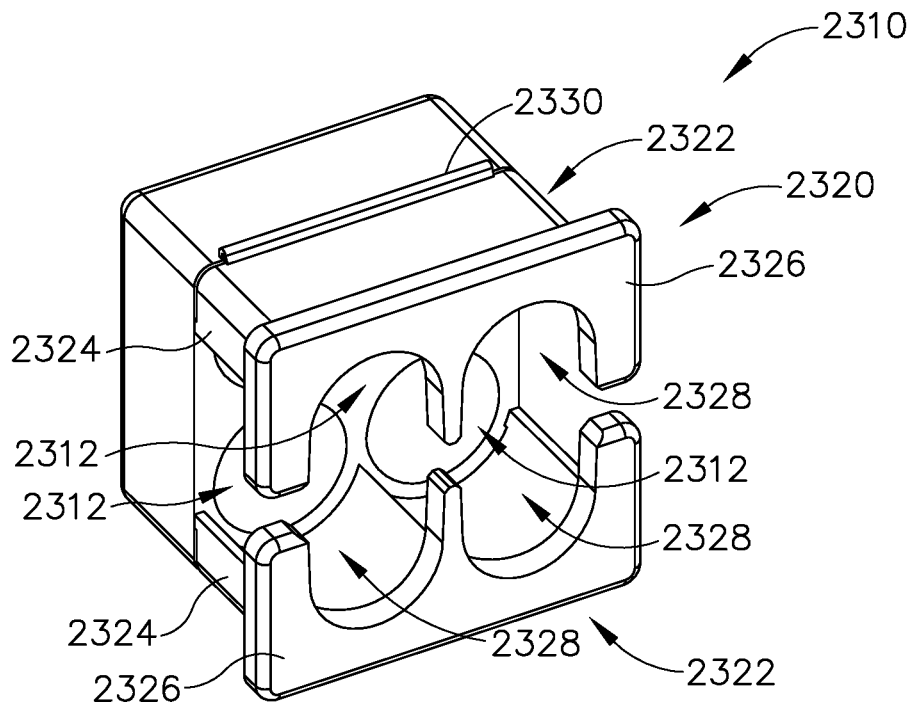
FIG. 27 depicts a perspective view of yet another exemplary alternative guide cube for use with the biopsy system of FIG. 1.
Figure 28:
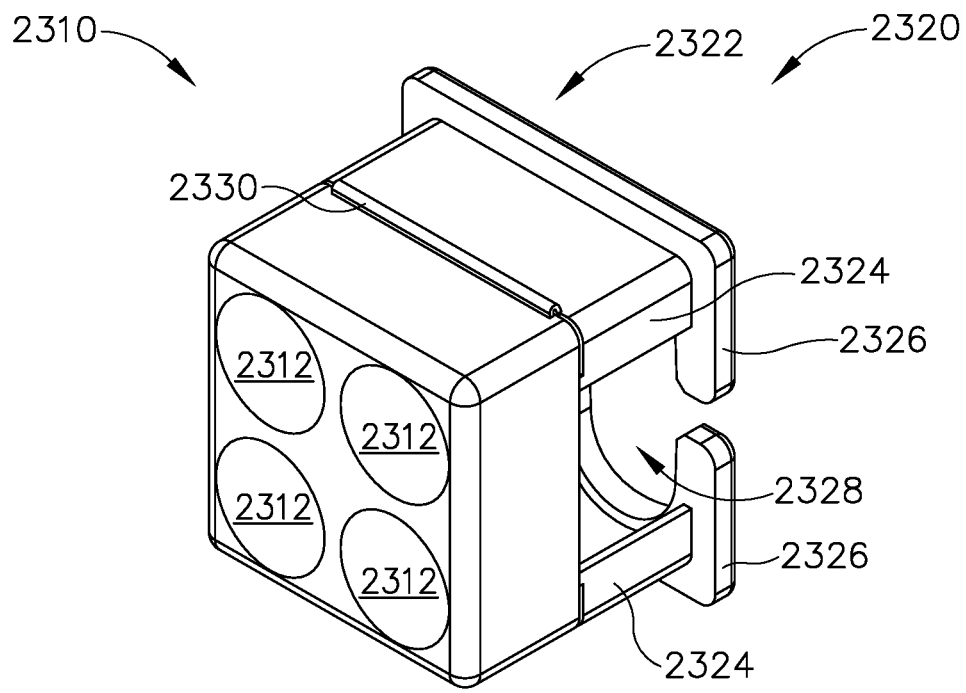
FIG. 28 depicts another perspective view of the guide cube of FIG. 27.
Figure 29:
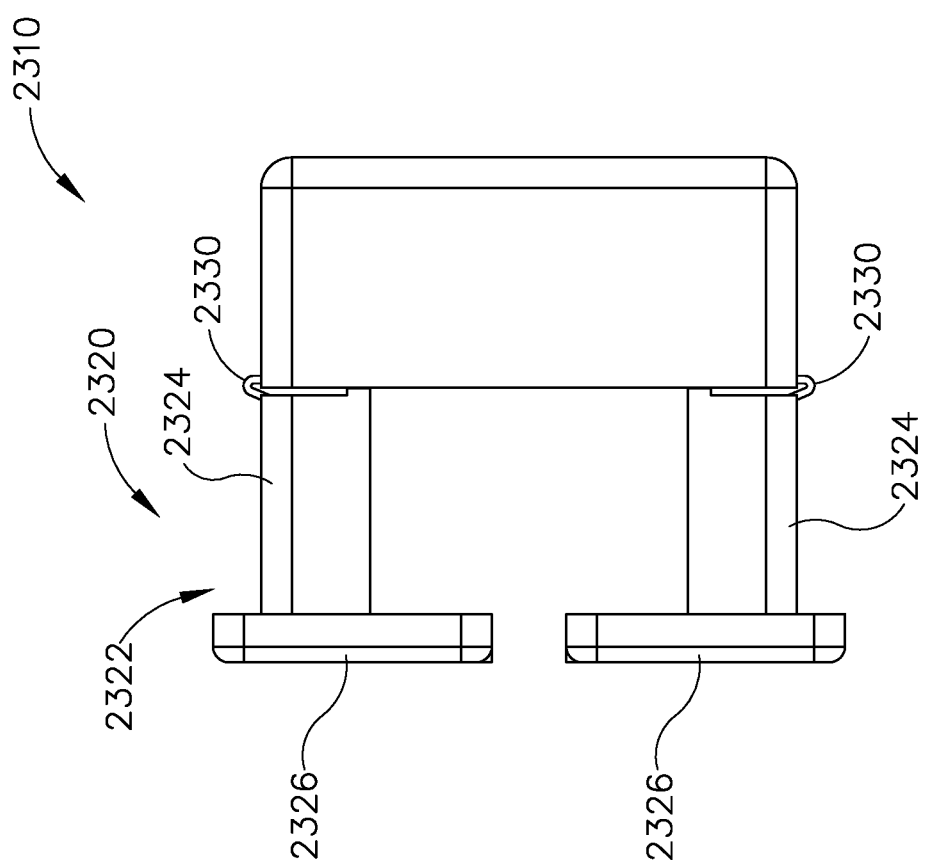
FIG. 29 depicts a side elevational view of the guide cube of FIG. 27.

FIGS. 24-26 show still another exemplary alternative guide cube (2210), which may be used in place of guide cube. Guide cube (2210) is similar to guide cubes (2010, 2110) described above. For instance, like guide cubes (2010, 2110), guide cube (2210) of the present example includes four corner holes (2212), and a depth stop coupling assembly (2220). However, unlike guide cubes (2010, 2110), guide cube (2210) includes a pair of grid engagement members (2214) that are actuated by a translatable actuation member (2219) as will be described in greater detail below. Holes (2212) are disposed in each corner of guide cube (2210) and extend through guide cube (2210) from the distal face of guide cube (2210) to the proximal face of guide cube (2210). Similarly to holes described above, holes (2212) of the present example are configured to receive cannula and obturator to guide cannula and obturator relative to grid plate when guide cube (2210) is inserted into grid plate.

Each grid engagement member (2214) comprises a resilient portion (2215) and an engagement portion (2216). Resilient portion (2215) is configured to resiliently bias engagement portion (2216) outwardly from guide cube (2210). However, resilient portion (2215) is also configured to permit engagement portion (2216) to deflect inwardly as guide cube (2210) is inserted into grid plate. Engagement portion (2216) protrudes from resilient portion (2215) away from the respective face of guide cube (2210). As will be described in greater detail below, engagement portion (2216) is configured to bear against grid plate to selectively lock guide cube (2210) into grid plate. Although engagement portion (2216) is shown as being integral with the rest of guide cube (2210), it should be understood that in other examples engagement portion (2216) may be of separate construction. In such examples, engagement portion (2216) comprises elastic or flexible characteristics to permit at least some distortion of engagement portion (2216) when bearing against gird plate.

As can best be seen in FIG. 25, guide cube (2210) includes an actuation member (2219) that is selectively insertable into guide cube (2210). It should be understood that when actuation member (2219) is inserted into guide cube (2210), actuation member (2219) is configured to define at least a portion of holes (2212).

Additionally, actuation member (2219) is configured to bear against engagement member (2214) to prevent deflection of resilient portion (2215) of engagement member (2214). In particular, as can best be seen in FIG. 25, when actuation member (2219) is fully inserted in guide cube (2210), actuation member (2219) abuts engagement member (2214), thereby preventing deflection of resilient portion (2215) inwardly.

In an exemplary use, actuation member (2219) is used to selectively lock guide cube (2210) into grid plate. In particular, guide cube (2210) may first be inserted into grid plate with actuation member (2219) either removed completely or partially from guide cube (2210). Once guide cube (2210) is positioned as desired in grid plate, actuation member (2219) then may be inserted into guide cube (2210). Once fully inserted, actuation member (2219) bears against engagement member (2214), forcing engagement portion (2216) into contact with grid plate. Because engagement portion (2216) protrudes from the outer surface of guide cube (2210), a compression fit between guide cube (2210) and grid plate will be created, thereby locking guide cube (2210) into grid plate.

Returning to FIG. 24, Depth stop coupling assembly (2220) comprises a plurality of indexing features (2222) and a plurality of lock arms (2230). Unlike indexing features (2022, 2122) described above, indexing features (2222) of the present example are only disposed on the outer portion of the proximal face of guide cube (2210). Indexing features (2222) are generally configured to cooperatively direct a portion of depth stop assembly (1010) into position relative to guide cube (2210). In particular, each indexing feature (2222) has a particular geometry corresponding to the cylindrical shape of cube coupling member (1018) of depth stop assembly (1010). As will be described in greater detail below, the geometry of each indexing feature (2222) is also configured to provide support to cube coupling member (1018) as it is lockingly engaged by depth stop coupling assembly (2220).

Each lock arm (2230) comprises a resilient portion (2232) and a tooth (2234). Resilient portion (2232) is configured to urge tooth (2234) into the position shown in FIG. 24. It should be understood that this position generally corresponds to the position of connector channel (1019) of depth stop assembly (1010). Accordingly, each tooth (2234) is resiliently biased to engage with connector channel (1019) of depth stop assembly (1010) when depth stop assembly (1010) is inserted into a given face defined by indexing features (2222). Thus, in an exemplary use, an operator merely has to inert depth stop assembly (1010) into a position adjacent to a given hole (2212) of guide cube (2210) and a respective lock arm (2230) will resiliently engage connector channel (1019).

FIGS. 27-32 show yet another exemplary alternative guide cube (2310) that may be used in place of guide cube. Guide cube (2310) is similar to guide cubes (2010, 2110, 2210) described above. For instance, like guide cubes (2010, 2110, 2210), guide cube (2310) of the present example includes four corner holes (2312). However, unlike guide cubes (2010, 2110, 2210), guide cube (2310) includes an integral depth stop assembly (2320) that is similar in function to depth stop assemblies (1010, 1110) described above. Thus, it should be understood that unlike guide cubes (2010, 2110, 2210) described above, guide cube (2310) is not generally usable with depth stop assemblies (1010, 1110). Instead, guide cube (2310) is configured for use with a depth stop device similar to depth stop device described above. Holes (2312) are disposed in each corner of guide cube (2310) and extend through guide cube (2310) from the distal face of guide cube (2310) to the proximal face. Similarly to holes (106, 108, 110) described above, holes (2312) of the present example are configured to receive cannula and obturator to guide cannula and obturator relative to grid plate when guide cube (2310) is inserted into grid plate.

Depth stop assembly (2320) of the present example comprises a pair of pivotable arms (2322). Arms (2322) are generally configured to pivot relative to guide cube (2310) to selectively capture depth stop device to thereby prevent proximal movement of depth stop device relative to guide cube (2310). Each arm (2322) extends proximally from guide cube (2310) and comprises a longitudinal member (2324) and a proximal blocking member (2326). Longitudinal member (2324) extends for a predetermined length from guide cube (2310). In some examples, the predetermined length of longitudinal member (2324) corresponds to the thickness of depth stop member, although any suitable length may be used. As will be described in greater detail below, where longitudinal member (2324) generally corresponds to the thickness of depth stop member, any movement of depth stop member will be relatively restricted because depth stop member may be adjacent to both proximal blocking member (2326) and guide cube (2310).

Each proximal blocking member (2326) defines a pair of openings (2328) that corresponds generally to at least a portion of each respective opening (2312) on guide cube (2310). Thus, it should be understood that each opening (2328) is configured to permit cannula and obturator to pass through proximal blocking member (2326). However, each opening (2328) is configured to block at least a portion of depth stop device to prevent movement of depth stop device relative to guide cube (2310).

Figure 30:
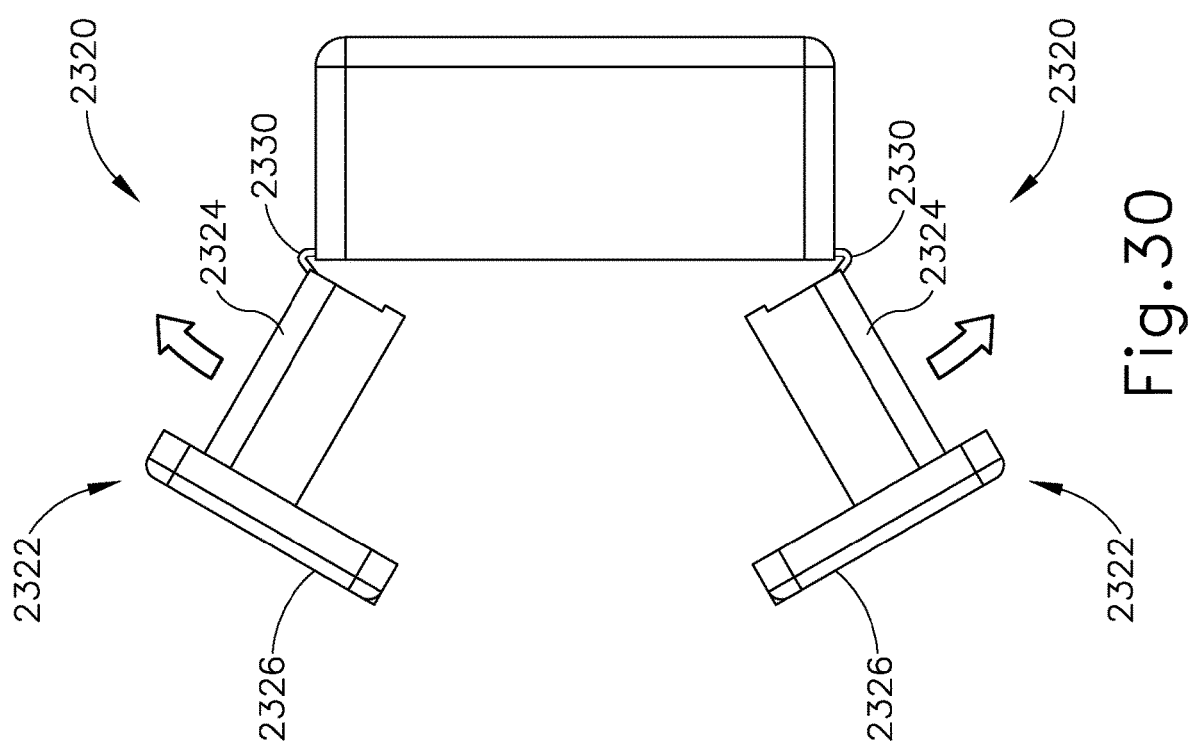
FIG. 30 depicts another side elevational view of the guide cube of FIG. 27, with a pair of arms pivoted away from the guide cube.

As can best be seen in FIG. 30, each arm (2322) is attached to guide cube (2310) with a living hinge (2330) or other suitable mechanism to permit pivoting of each arm (2322). As can be seen, each living hinge (2330) permits each arm (2322) to pivot relative to guide cube (2310) to leave an unrestricted path to each hole (2312) of guide cube (2312). Thus, each arm (2322) is generally configured to pivot out of the path of cannula, obturator, and depth stop device for insertion into a given hole (2312) and then pivotably return to lock depth stop device into position.

FIGS. 27-32 show an exemplary use of guide cube (2310). As can be seen, arms (2322) may initially be in a closed position. In this position, cannula and obturator may be inserted into guide cube (2310), however, depth stop device will be blocked by arms (2322). During this stage, an operator may first set a desired penetration depth on cannula by longitudinally positioning depth stop device relative to cannula and then locking the longitudinal position of depth stop device on cannula.

Figure 31:
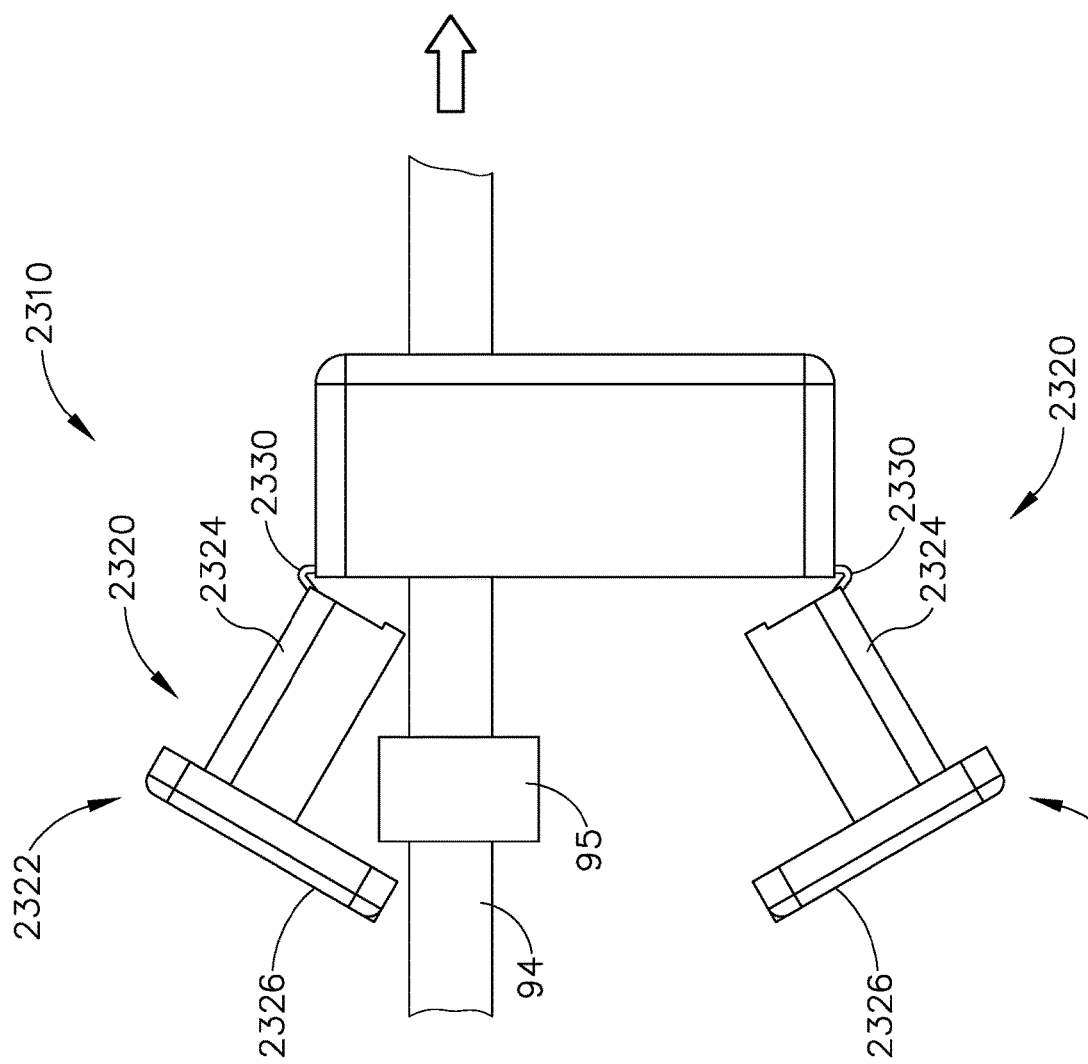
FIG. 31 depicts still another side elevational view of the guide cube of FIG. 27, with a cannula and depth stop device being inserted into the guide cube.
Figure 32:
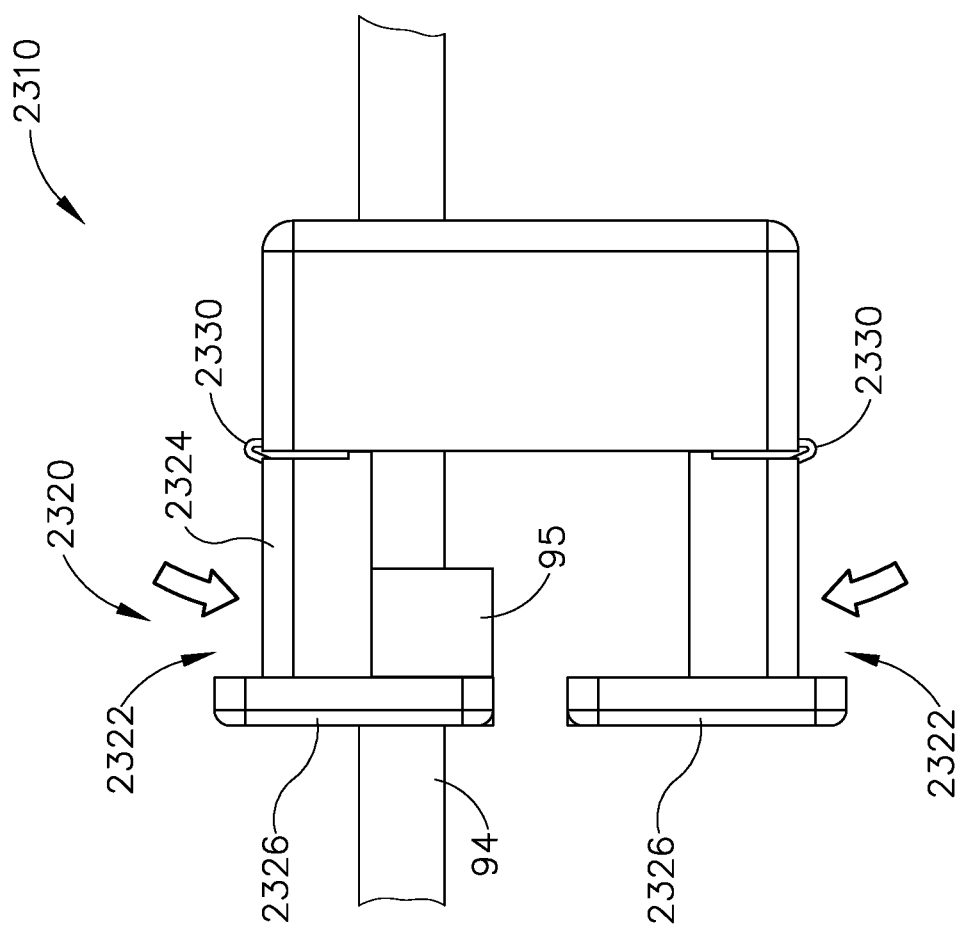
FIG. 32 depicts yet another side elevational view of the guide cube of FIG. 27, with the arms of FIG. 30 pivoted to lock the cannula relative to the guide cube.

Once the operator has positioned depth stop device to correspond to a desired penetration depth, the operator may prepare guide cube (2310) for insertion of cannula, obturator, and depth stop device. To prepare guide cube (2310) for insertion, the operator may pivot arms (2322) to the position shown in FIG. 30. Once positioned, arms (2322) expose a clear path to holes (2312) in guide cube (2310). Thus, the operator may next insert cannula, obturator, and depth stop device into guide cube (2310), as shown in FIG. 31.

Once cannula and obturator are inserted into guide cube (2310), depth stop device may be locked in position using arms (2322). As can best be seen in FIG. 32, arms (2322) may be returned to the initial position by the operator. Once arms (2322) are returned to the initial position, cannula and obturator will fit through openings (2328) in proximal blocking member (2326). However, proximal translation of depth stop device will be prevented by blocking member (2326) and/or guide cube (2310). To maintain arms (2322) in the locked position, an operator may then insert guide cube (2310) into grid plate.

In the present example, longitudinal member (2324) of arms (2322) is longer than the thickness of depth stop member. Accordingly, some movement of depth stop device will be permitted within a predetermined range of motion. As described above, in other examples the length of longitudinal member (2324) may correspond to the thickness of depth stop device such that generally all longitudinal motion of depth stop device will be prevented.

FIGS. 33-37 show an exemplary combination guide cube depth stop device (2410). Device (2410) is generally usable with targeting set as described above, unless otherwise described herein. Device (2410) comprises a depth stop carriage (2440) and a guide cube portion (2411). Depth stop carriage (2440) comprises a track (2442) and a carriage assembly (2450). Track (2442) extends proximally from a grid lock (2560) and is configured to attach to grid plate. As will be described in greater detail below, track (2442) is generally rotatable to actuate grid lock (2560) within grid plate. Track (2442) includes an indented portion (2444) that includes a plurality of stop features (2446). As will be described in greater detail below, stop features (2446) are configured to be engaged by a portion of carriage assembly (2450) to secure the longitudinal position of carriage assembly (2450) relative to track (2442).

Figure 33:
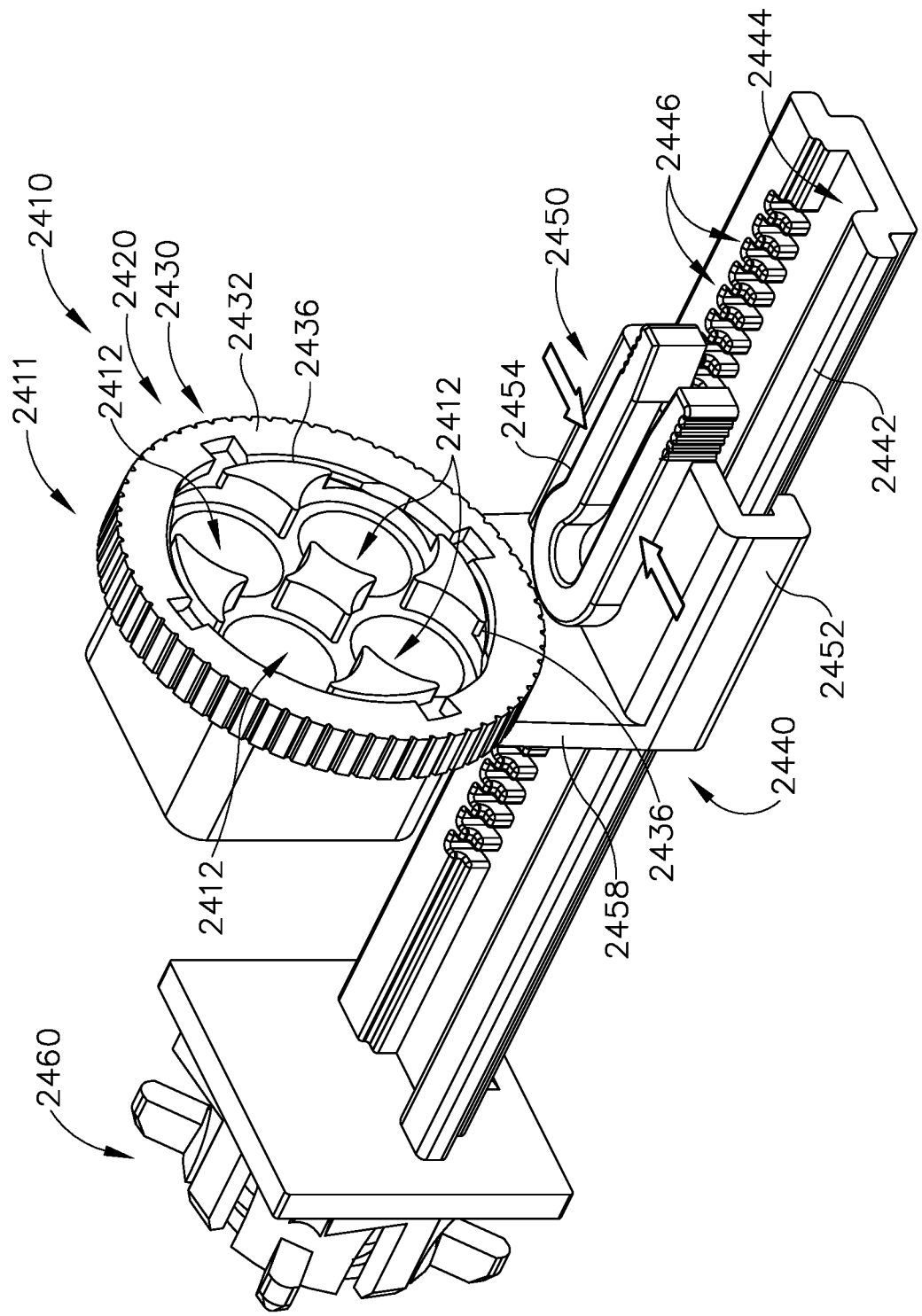
FIG. 33 depicts a perspective view of an exemplary alternative combination guide cube and depth stop device.
Figure 34:
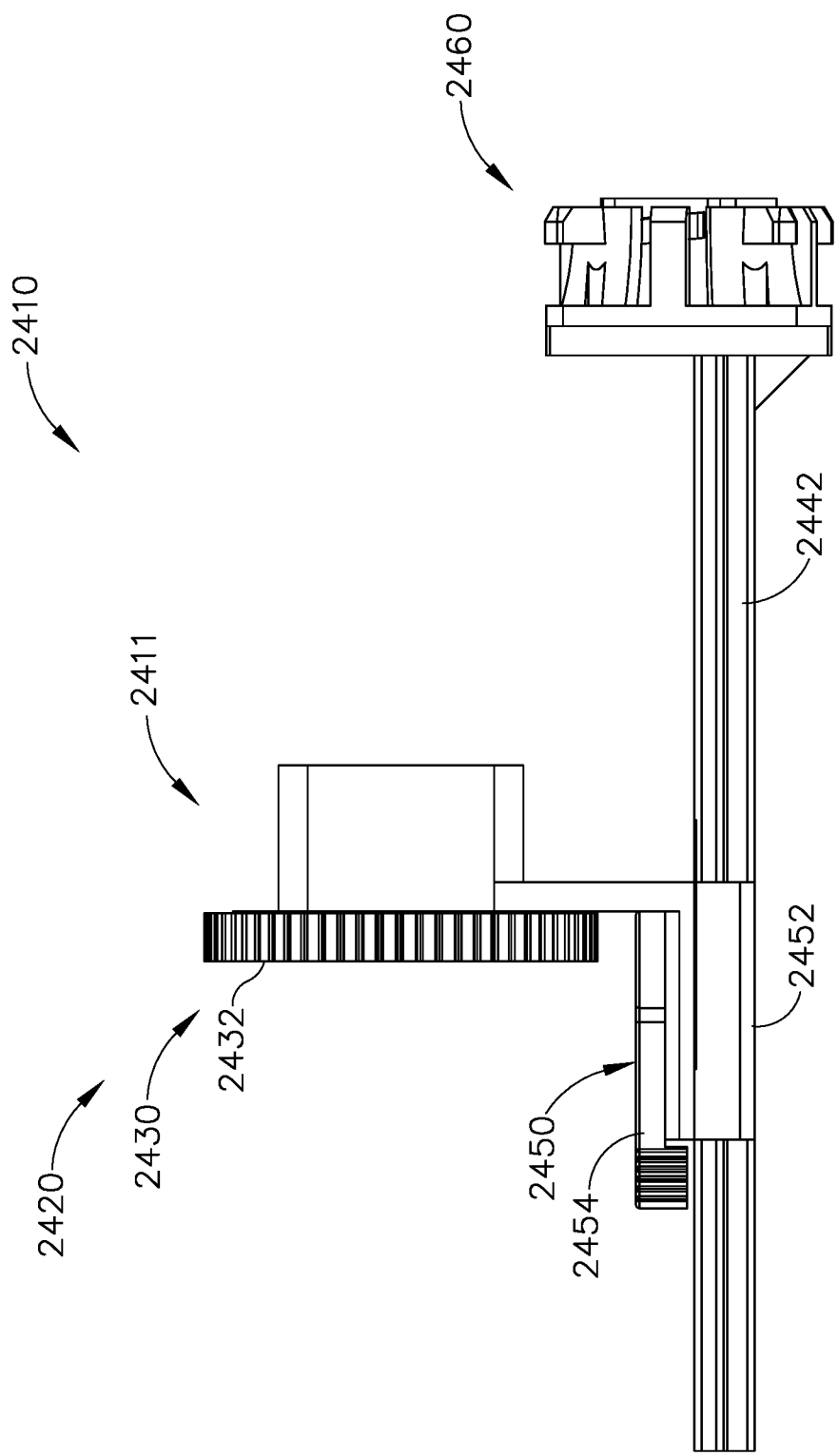
FIG. 34 depicts a side elevational view of the device of FIG. 33.
Figure 35:
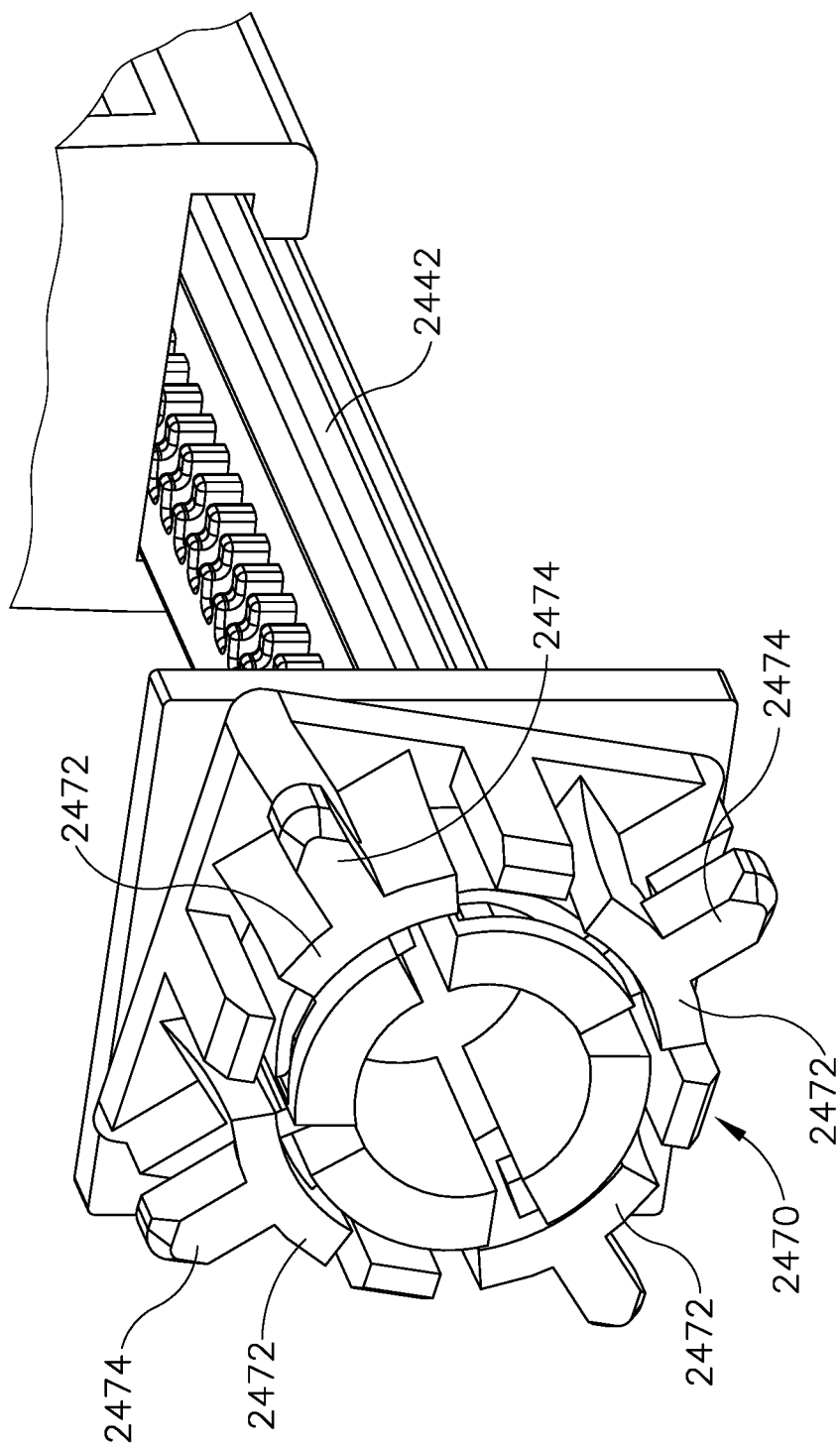
FIG. 35 depicts a detailed perspective view of a grid lock of the device of FIG. 33.

Carriage assembly (2450) comprises a track engagement portion (2452) and an upright portion (2458). Track engagement portion (2452) wraps around track (2442) and is configured to slide longitudinally along track (2442). Track engagement portion (2452) includes a resilient lock feature (2454). Lock feature (2454) is resiliently biased to engage with stop features (2446) of tack (2442). Thus, lock feature (2454) is naturally biased to lock the position of carriage assembly (2450) relative to track (2442). To adjust the longitudinal position of carriage assembly (2450) relative to track (2442), an operator may actuate lock feature (2454) as indicated in FIG. 33 by pinching inwardly on lock feature (2454) to disengage lock feature (2454) from stop features (2446), thereby permitting longitudinal movement of carriage assembly (2450) relative to track (2442).

Upright portion (2458) is integral with track engagement portion (2452) and guide cube portion (2411). Thus, guide cube portion (2411) is attached to carriage assembly (2450) such that the insertion depth of a cannula and obturator similar to cannula and obturator described above is determined by the longitudinal position of carriage assembly (2450) relative to track (2442).

Figure 36:
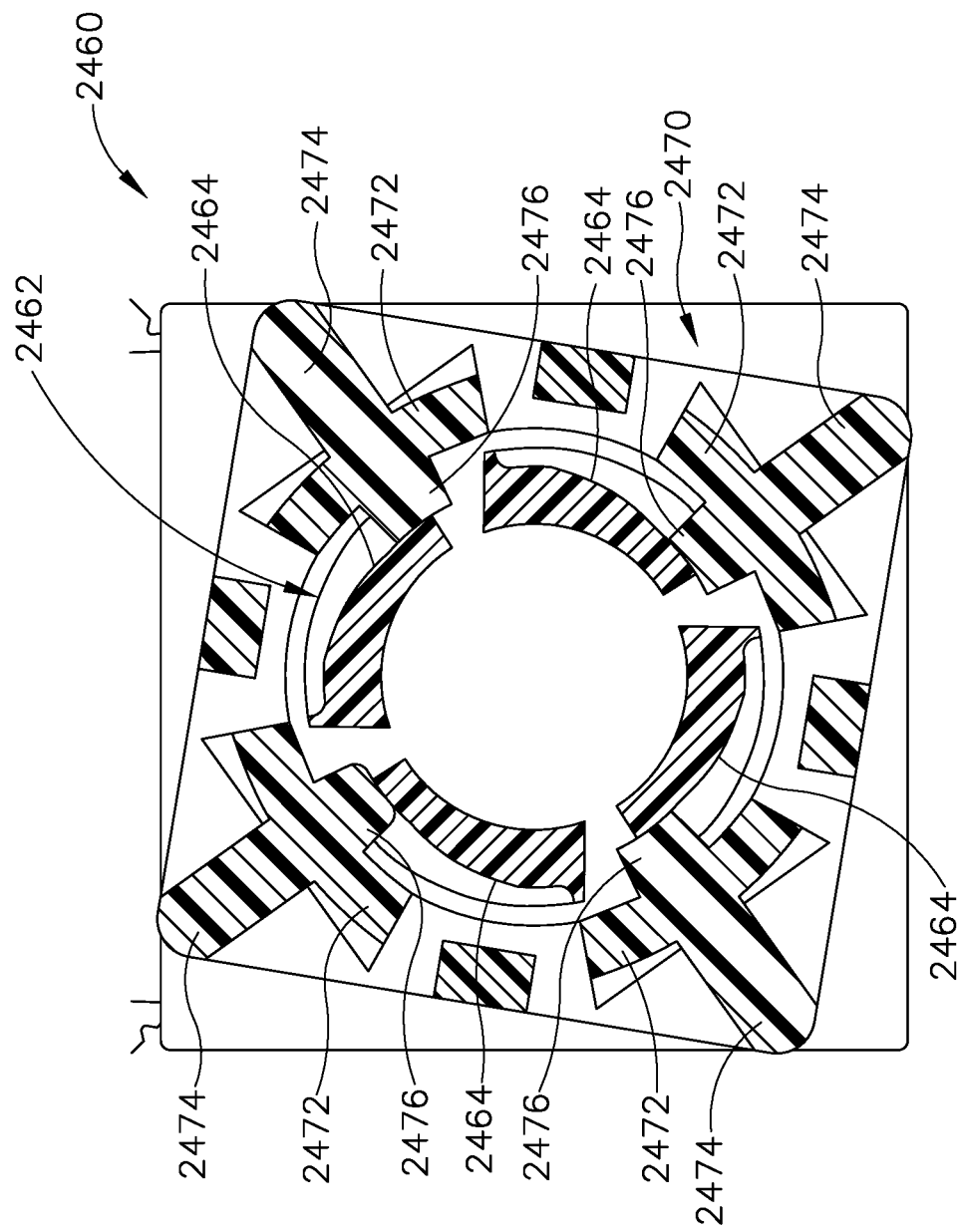
FIG. 36 depicts a front cross-sectional view of the grid lock of FIG. 35, with the grid lock in an unlocked position.

Grid lock (2460) is best shown in FIGS. 33-34 and 36-37. As described above, grid lock (2460) is generally configured to lock to grid plate by rotation of track (2442) relative to grid plate. Grid lock (2460) generally comprises an inner portion (2462) and an outer portion (2470). Inner portion (2462) is best shown in FIG. 36. As can be seen, inner portion (2462) is integral with track (2442) such that rotation of track (2442) also results in rotation of inner portion (2462). As will be described in greater detail below, inner portion (2462) is generally configured such that rotation of track (2442) will result in actuation of outer portion (2470). Inner portion (2462) defines a plurality of ramped surfaces (2464). Ramped surfaces (2464) are configured to engage at least a portion of outer portion (2470) to generally actuate outer portion (2470). Each ramped surface (2464) is oriented about a central axis such that ramped surfaces (2464) are oriented in a circular pattern. The circular pattern of ramped surfaces (2464) corresponds to an inner diameter defined by at least a portion of outer portion (2470), as will be described in greater detail below.

Returning to FIG. 35, outer portion (2470) is generally circular in shape and defines four resilient portions (2472). Outer portion (2470) further includes four lock arms (2474) extending outwardly from resilient portions (2472). Resilient portions (2472) are generally flexible such that each resilient portion (2472) is configured to be displaced outwardly by inner portion (2462), as will be described in greater detail below. Each lock arm (2474) is configured to engage with a corresponding corner of grid plate. Thus, it should be understood that when each resilient portion (2472) is displaced outwardly by inner portion (2462), each lock arm (2474) is correspondingly displaced outwardly to lockingly engage with a respective corner of grid plate.

As can be seen in FIG. 36, outer portion (2470) further includes four actuation members (2476) adjacent to each lock arm (2474) protruding inwardly from resilient portions (2472) of outer portion (2470). Actuation members (2476) collectively define an inner diameter that is generally equivalent to the smallest diameter defined by ramped surfaces (2464) of inner portion (2462). As will be described in greater detail below, each actuation member (2476) is configured to engage a respective ramped surface (2464) of inner portion (2462) to actuate grid lock (2460).

Figure 37:
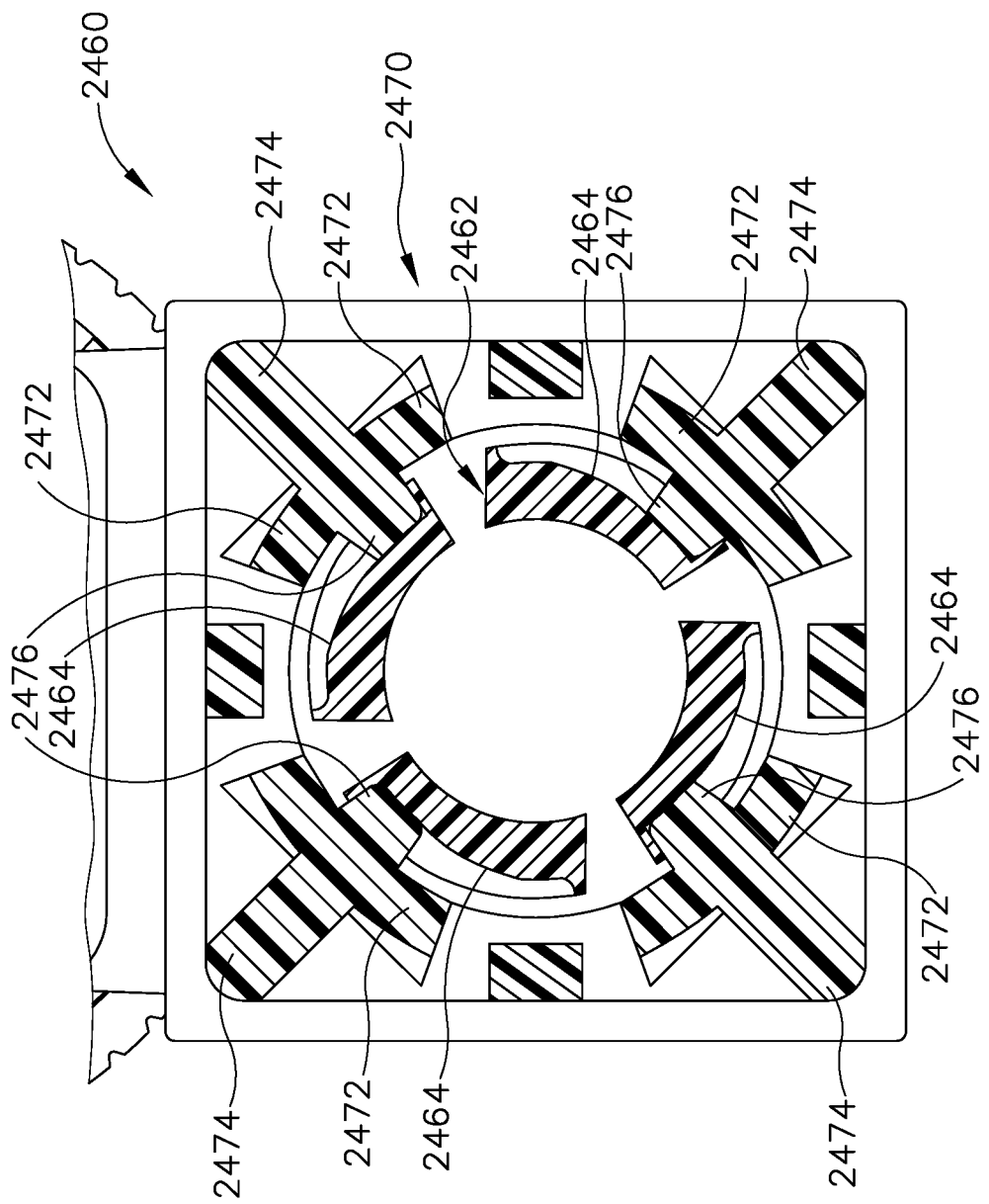
FIG. 37 depicts another front cross-sectional view of the grid lock of FIG. 35, with the grid lock in a locked position.

FIGS. 36 and 37 show an exemplary use of grid lock (2460). As can be seen, initially, actuation members (2476) of outer portion (2470) are initially engaged with the lowest portion of each ramped surface (2464). In this initial position, lock arms (2474) are in a retracted position, such that grid lock (2460) can be inserted into grid plate without substantial interference from lock arms (2474).

To actuate grid lock (2460), an operator may insert grid lock (2460) into grid plate. An operator may then rotate track (2442) about a longitudinal axis to initiate locking of grid lock (2460) relative to grid plate. Lock arms (2474) will then engage with grid plate causing outer portion (2470) to begin to rotate relative to inner portion (2462). As outer portion (2470) rotates, actuation members (2476) travel up each ramped surface (2464), pushing each lock arm (2474) outwardly. The operator may continue rotation of track (2442) to the position shown in FIG. 34. At such a position further rotation is restricted by engagement between lock arms (2474) and grid plate.

Returning to FIGS. 33, 34 and 39, guide cube portion (2411) is substantially the same as guide cube (2010) described above. For instance, guide cube portion (2411) includes four corner holes (2412), and a depth stop coupling assembly (2420). Holes (2412) are disposed in each corner of guide cube portion (2411) and extend through guide cube portion (2411) from the distal face of guide cube portion (2411) to the proximal face. Similarly to holes described in references, holes (2412) of the present example are configured to receive cannula and obturator to guide cannula and obturator relative to grid plate when guide cube portion (2411) is inserted into grid plate.

Depth stop coupling assembly (2420) is substantially the same as depth stop coupling assembly (2020) described above. Although the depth stop coupling assembly (2420) may be useable with a depth stop assembly such as depth stop assembly (1010) described above, the present example is described herein as being usable in conjunction with a cannula (2494) that includes similar components as will be described in greater detail below.

Like with depth stop coupling assembly (2020) described above, depth stop coupling assembly (2420) comprises a rotatable lock feature (2430) that is generally configured to rotate relative to guide cube portion (2411) to selectively lock cannula (2494) to guide cube portion (2410). In particular, lock feature (2430) includes a rotatable hub (2432). Rotatable hub (2432) includes a plurality of lock protrusions (2436) that are substantially similar to lock protrusions (2036) described above. Thus, it should be understood that depth stop coupling assembly (2420) functions substantially similarly to depth stop coupling assembly (2020) described above such that an operator may rotate rotatable hub (2432) to selectively move lock protrusions (2436) into engagement with a portion of cannula (2494) to lock cannula (2494) to guide cube portion (2411).

Figure 38:
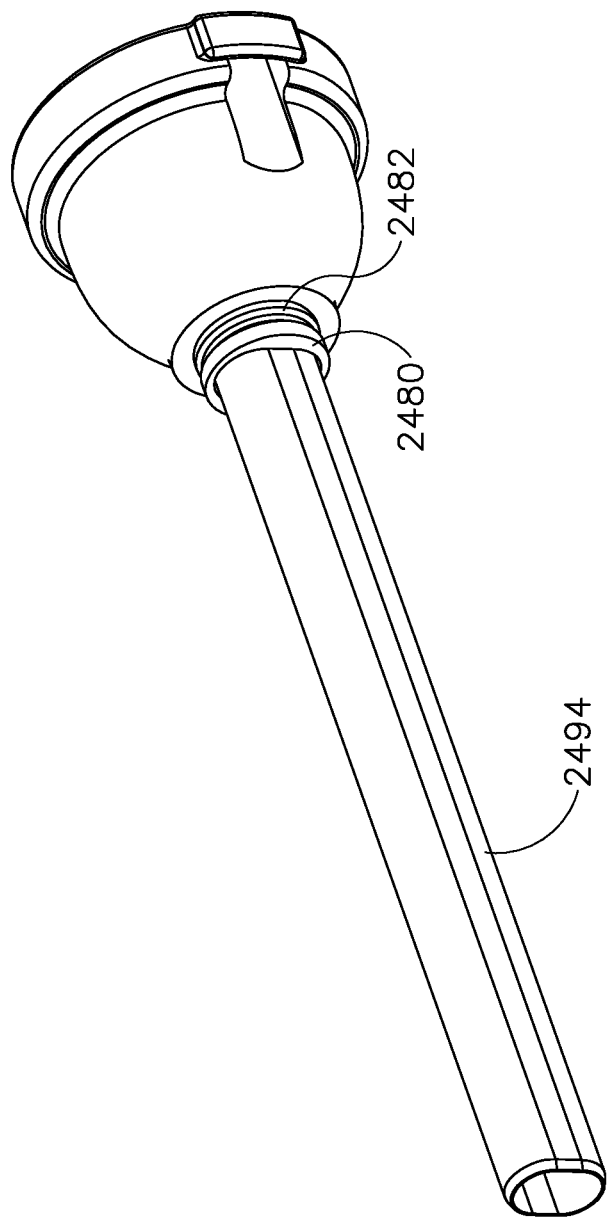
FIG. 38 depicts a perspective view of an exemplary alternative cannula for use with the device of FIG. 33.

FIG. 38 shows an exemplary alternative cannula (2494) that is generally usable with device (2410) in lieu of cannula. Unlike cannula described above, cannula (2494) includes a cube coupling member (2480). Cube coupling member (2480) includes an annular connector channel (2480). Cube coupling member (2480) generally permits coupling of cannula (2494) to guide cube portion (2411) as similarly described with respect to cube coupling member (1018) of depth stop assembly (1010) described above.

Figure 39:
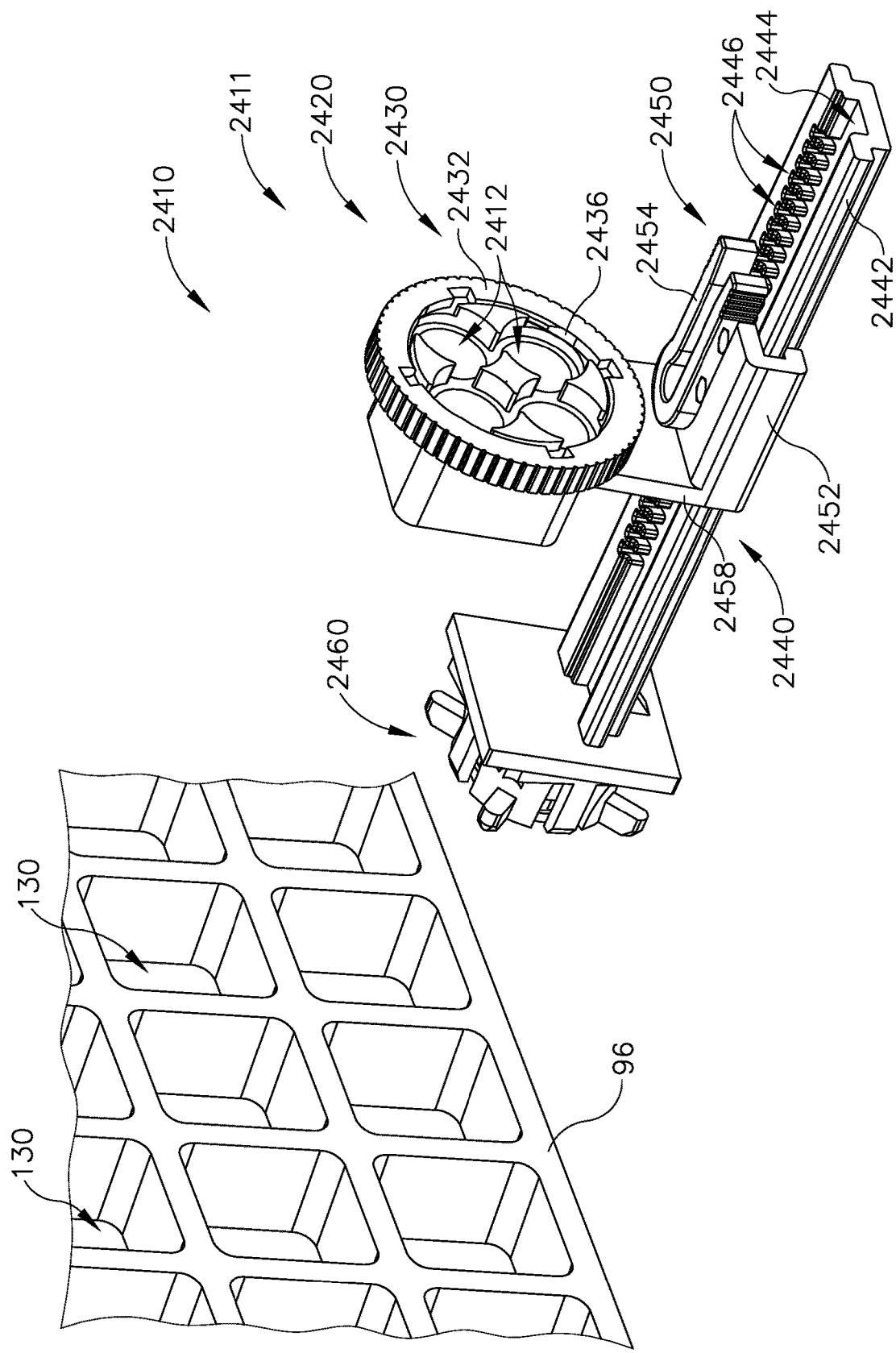
FIG. 39 depicts a perspective view of the device of FIG. 33 prior to insertion into a grid plate of the biopsy system of FIG. 1.
Figure 40:
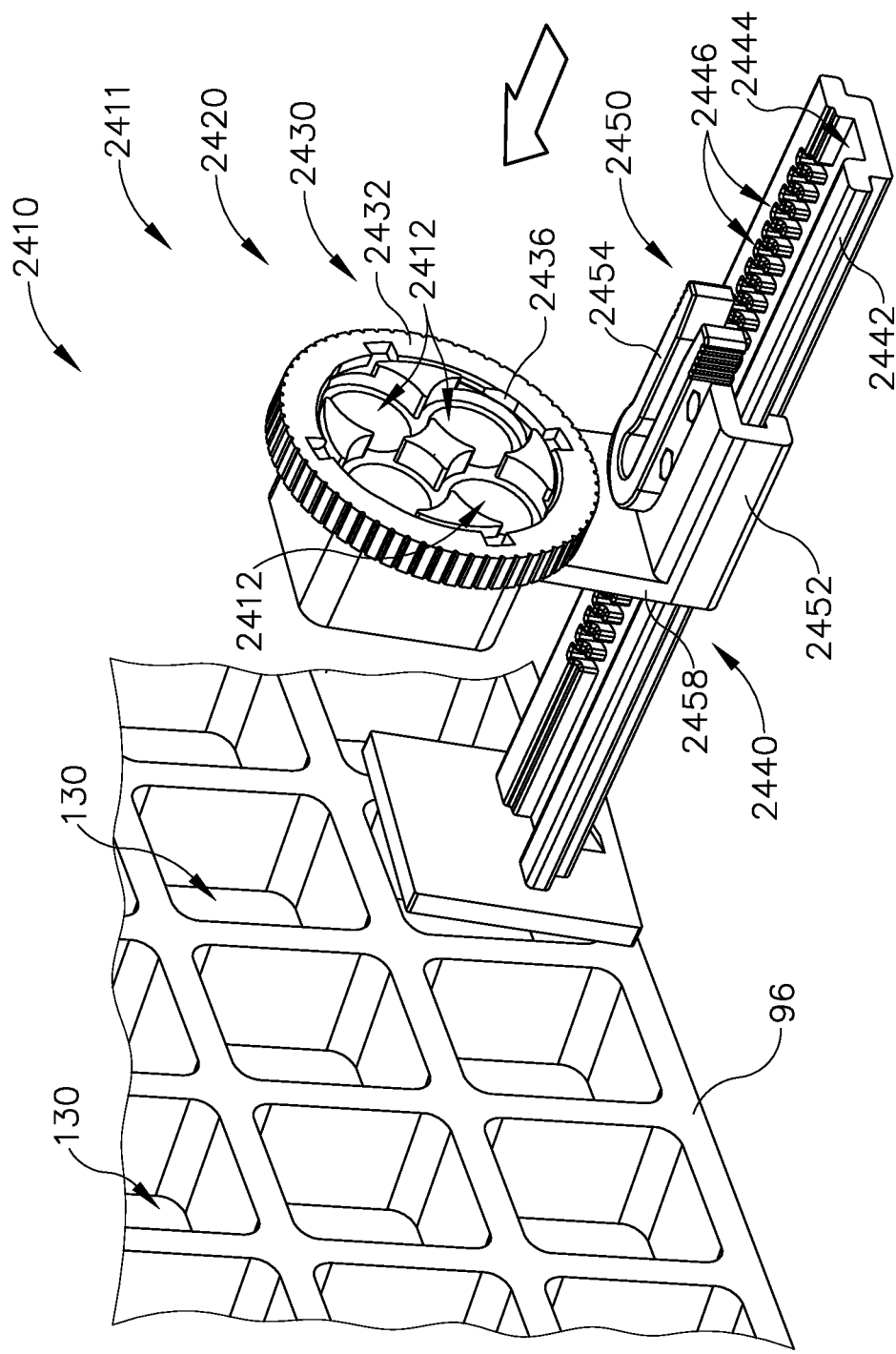
FIG. 40 depicts another perspective view of the device of FIG. 33, with the grid lock of FIG. 35 inserted into the grid plate.
Figure 41:
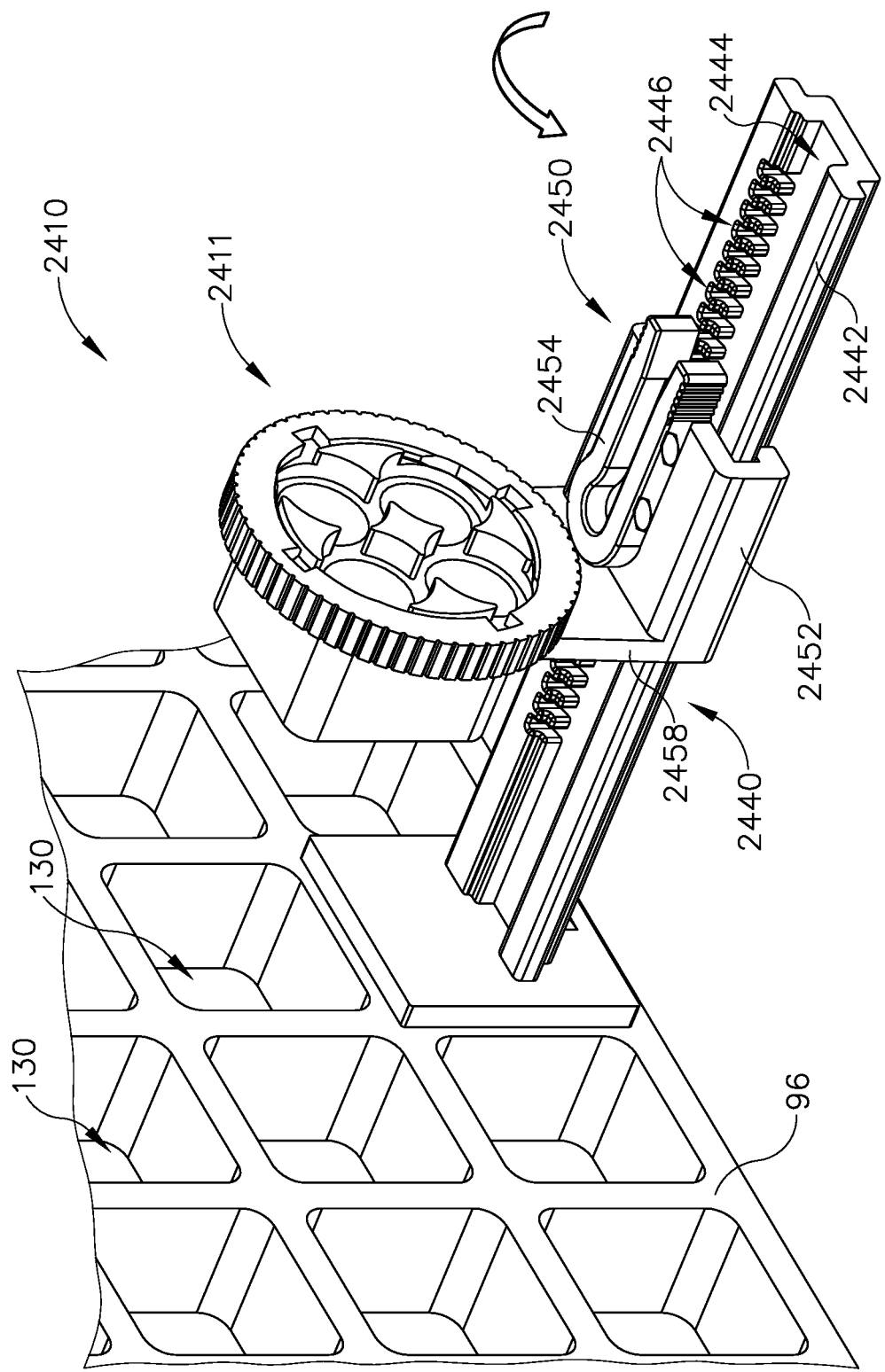
FIG. 41 depicts still another perspective view of the device of FIG. 33, with the device rotated to actuate the grid lock to the locked position.

An exemplary use of device (2410) is shown in FIGS. 39-44. In particular, as can be seen in FIG. 39, device (2410) may initially be rotated about a longitudinal axis in preparation for insertion into grid plate. Once rotated, device (2410) may be inserted into grid plate as shown in FIG. 40. The operator may then rotate device (2410) about a longitudinal axis that is parallel to the longitudinal axis of track (2442) to lock device (2410) to grid plate as described above and as shown in FIG. 41.

Once device (2410) is locked onto grid plate, an operator may optionally adjust carriage assembly (2450) relative to track (2442) to achieve a desired penetration depth. Alternatively, an operator may perform this step later when cannula (2494) is at least partially inserted into guide cube portion (2411).

Figure 42:
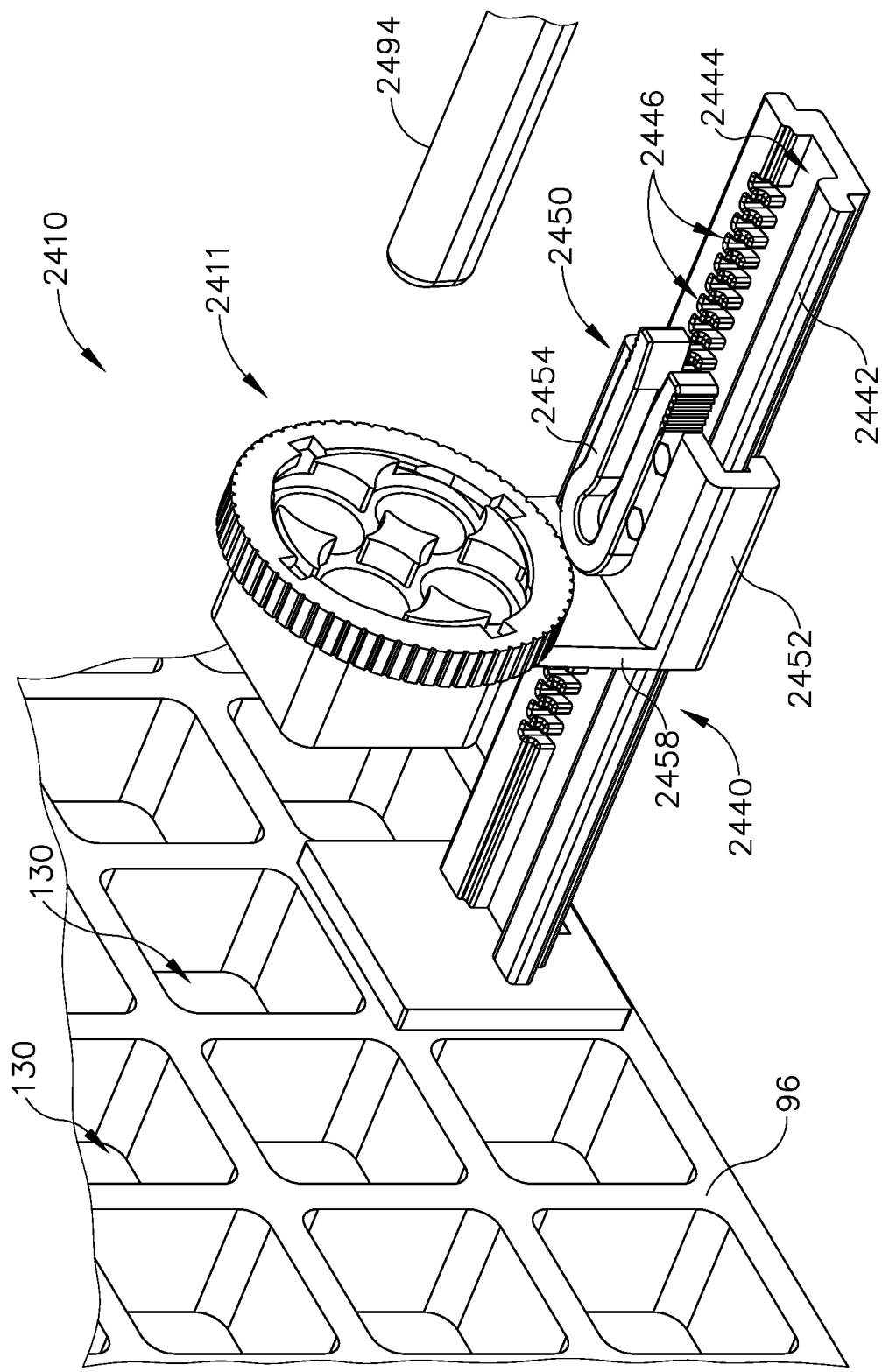
FIG. 42 depicts yet another perspective view of the device of FIG. 33, with the cannula of FIG. 38 prepared for insertion into the device.
Figure 43:
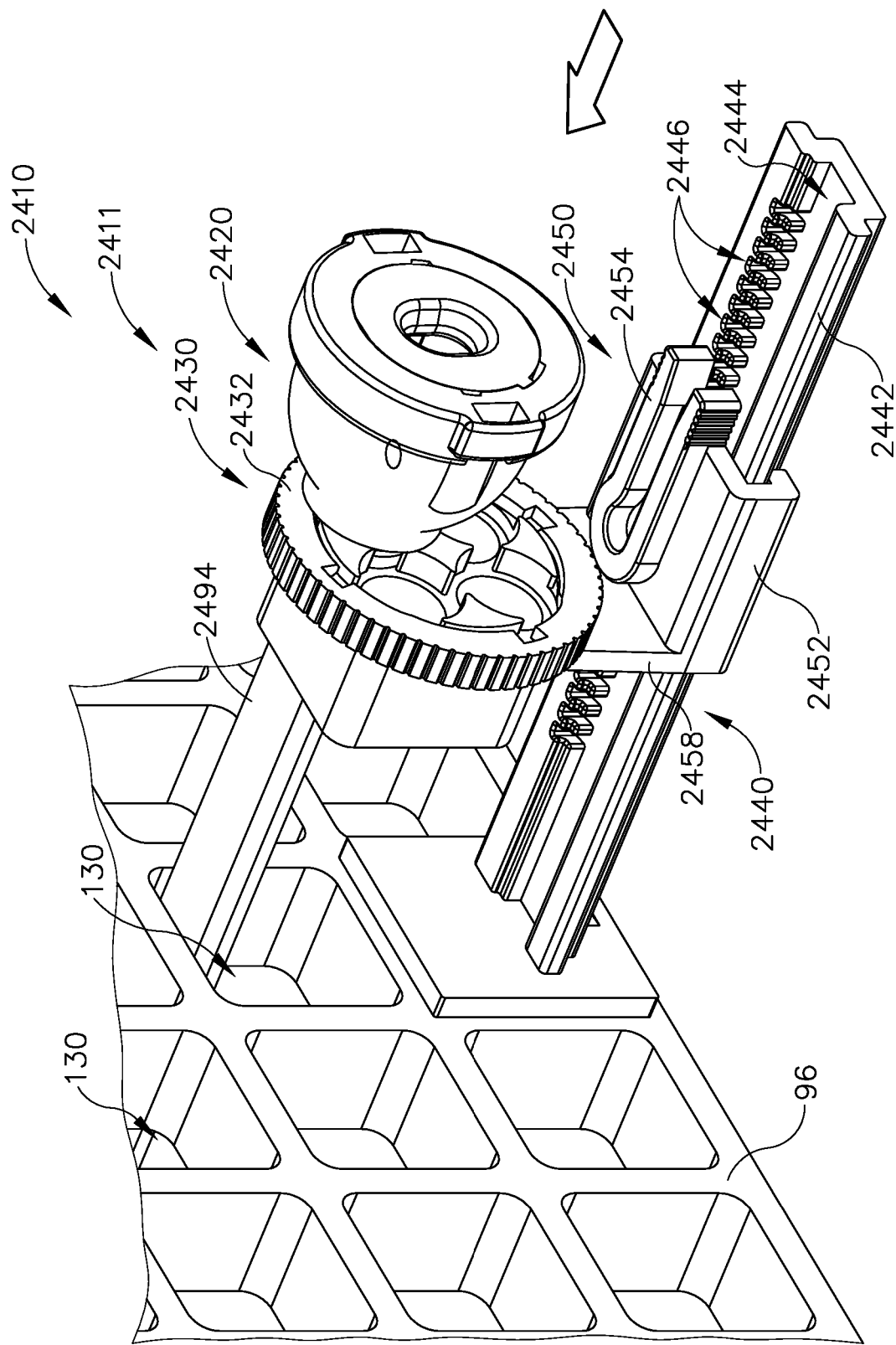
FIG. 43 depicts yet another perspective view of the device of FIG. 33, with the cannula of FIG. 38 inserted into the device.
Figure 44:
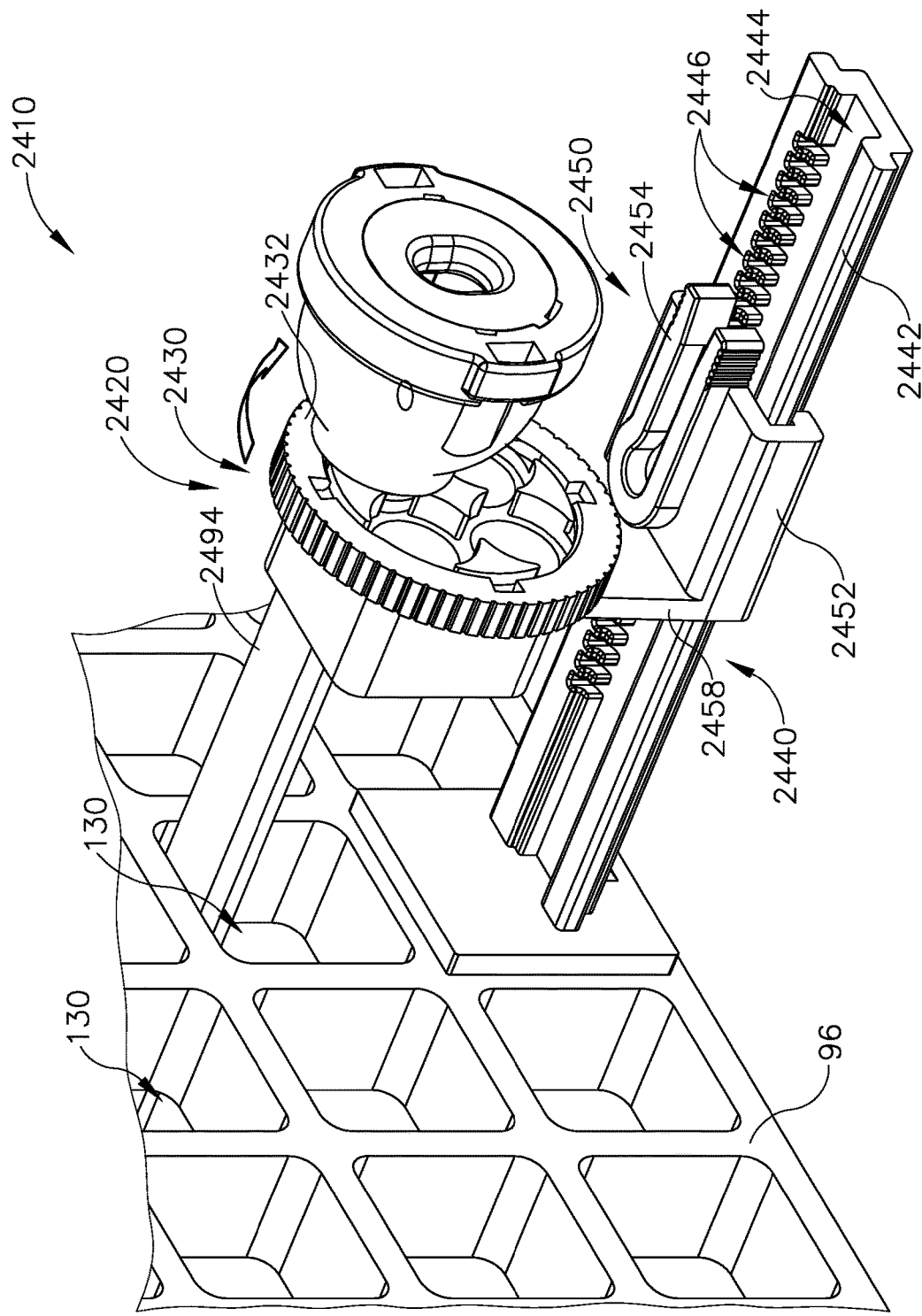
FIG. 44 depicts yet another perspective view of the device of FIG. 33, with the cannula of FIG. 38 locked to the device

Next, an operator may insert cannula (2494) into guide cube portion (2411) as shown in FIGS. 42 and 43. Although not shown, it should be understood that cannula (2494) may be inserted with an obturator similar to obturator described above. Once cannula (2494) is inserted into guide cube portion (2411), an operator may lock cannula (2494) into position by actuating guide cube portion (2411) as described above and shown in FIG. 33.

Figure 45:
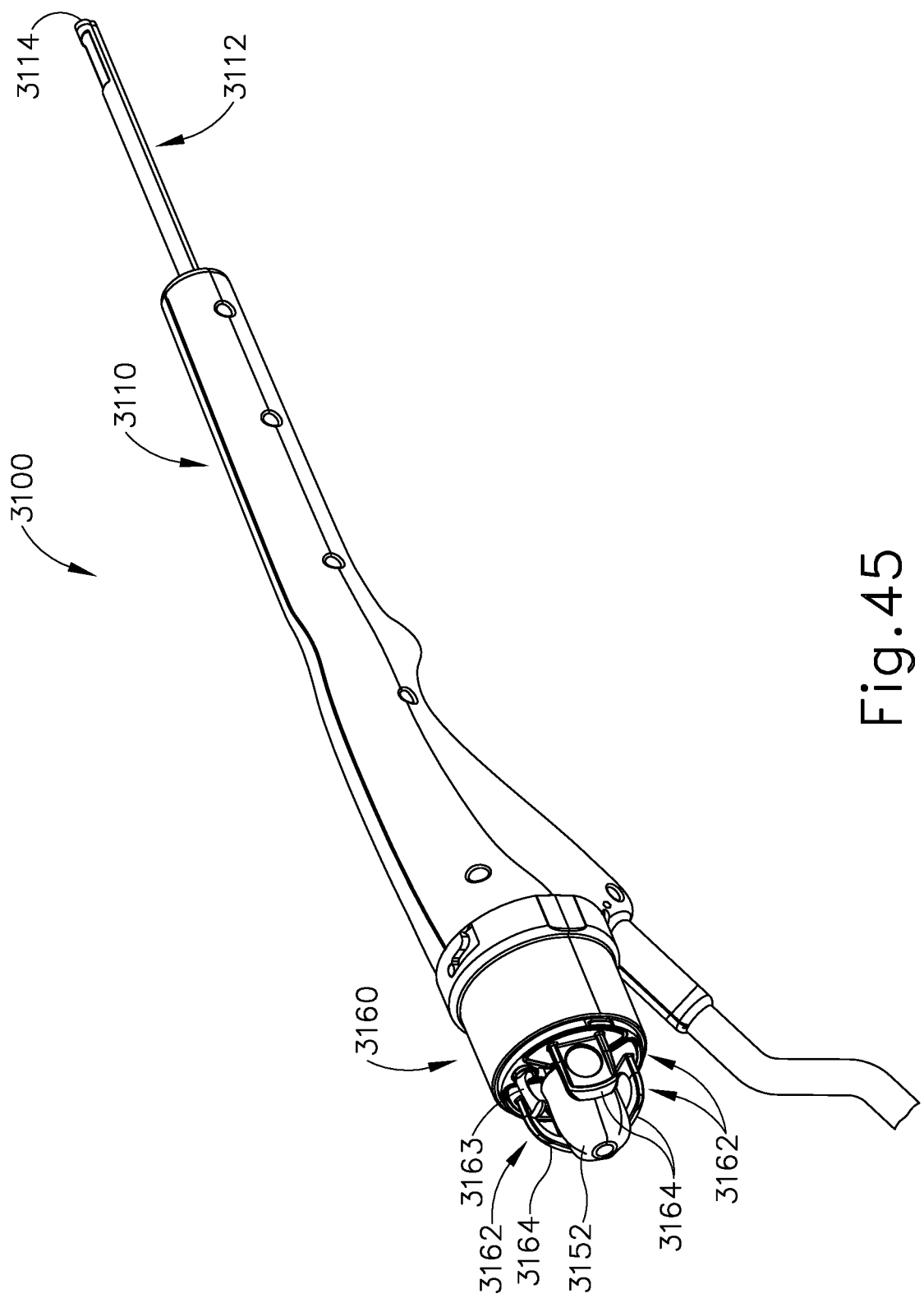
FIG. 45 depicts a perspective view of an exemplary alternative biopsy device that is usable with the biopsy system of FIG. 1.

FIG. 45 shows an exemplary biopsy device (3100) that may be readily used in conjunction with targeting set and numerous other devices described above and in the cited references. Biopsy device (3100) of this example is substantially similar to biopsy device, except as otherwise noted herein. However, unlike biopsy device described in cited references, biopsy device (3100) of the present example comprises a combination probe/holster instead of separate probe and holster portions as described above and in the cited references with respect to the biopsy device. Biopsy device (3100) comprises a body (3110) with an elongate needle (3512) extending from body (3110). Needle (3112) is substantially similar to needle (90) described above. However, unlike needle (90), needle (3112) of the present example comprises a blunt tip (3114).

Biopsy device (3100) further includes a tissue sample holder (3160). Tissue sample holder (3100) is configured to receive three separate tissue collection trays (3162) and a single plug (3163). Trays (3162) are selectively removable from tissue sample holder (3160). To assist with the removability of trays (3162), each tray (3162) comprises a handle (3164) to allow an operator to grip each tray (3162) and pull each tray proximally from tissue sample holder (3160).

Each tray (3162) is configured to collect one or more tissue samples as tissue samples are collected via needle (3112). In some examples, biopsy device (3100) is configured to selectively index each tissue sample tray (3162) into communication with needle (3112) for collection of tissue samples. Indexing may be accomplished in a variety of suitable patterns. For instance, in one example tissue sample holder (3160) may index after the collection of each tissue sample. In another example, tissue sample holder (3160) may maintain a consistent angular position during the collection of a certain predetermined number of tissue samples before indexing to the next tray (3162). In still another example, indexing of trays (3162) may be entirely operator controlled. Of course, numerous other methods of indexing tissue sample holder (3160) into communication with needle (3112) will be apparent to those of ordinary skill in the art in view of the teachings herein.

Biopsy device (3100) of the present example further includes a rotation knob (3152) extending proximally from a tissue sample holder (3160). Rotation knob (3152) is in communication with internal components in body (3110) of biopsy device (3100). Through various mechanisms such as gears, shafts, and the like, rotation knob (3152) is in communication with needle (3112). In particular, in the present example rotation knob (3152) is configured to rotate needle (3112) about the longitudinal axis of needle (3112). With rotation knob (3152) extending proximally from tissue holder (3160), an operator may rotate needle (3112) without substantially changing the position of the operator's hand. It should be understood that while rotation knob (3152) is integrated into tissue holder (3160), rotation knob (3152) remains independently rotatable relative to tissue sample holder assembly (3160). In some examples, rotation knob (3152) may have a one-to-one relationship with rotation of needle (3112) such that one discrete rotation of rotation knob (3152) through a particular range of angular motion results in one discrete rotation of needle (3112) through the same particular range of angular motion. In other examples, the internal components of body (3110) may provide some mechanical advantage such that rotation of rotation knob (3152) through a particular range of angular motion results in rotation of needle (3112) through a larger or smaller range of angular motion.

Figure 46:
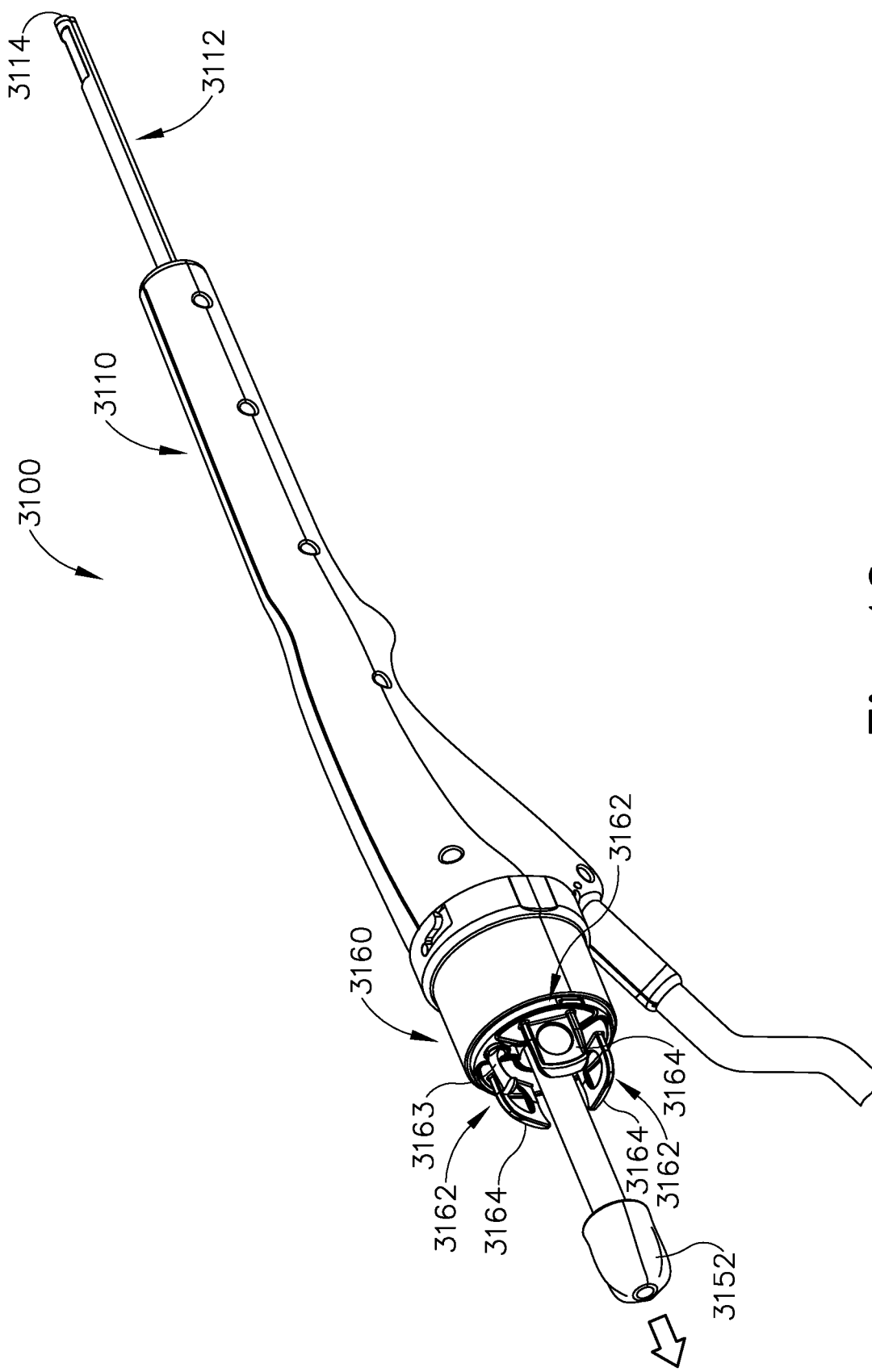
FIG. 46 depicts another perspective view of the biopsy device of FIG. 45, with a rotation knob extended proximally from the biopsy device.

Rotation knob (3152) is further configured to translate relative to tissue sample holder (3160). In particular, as can be seen in FIG. 46, rotation knob (3152) is configured to be pulled by a user proximally relative to tissue sample holder (3160) along the longitudinal axis of biopsy device (3100). Such a feature may be desirable to clear the proximal end of rotation knob (3152) from tissue sample trays (3162), thereby permitting greater accessibility to tissue sample trays (3162). In the present example, translation of rotation knob (3152) has no impact on the ability of rotation knob (3152) to rotate needle (3112). In other examples, translation of rotation knob (3152) may alternatively either activate or disable rotation of needle (3112) via rotation knob (3152). In still other versions, translation of rotation knob (3152) may shift the function of rotation knob (3152) from rotating needle (3112) to rotating tissue sample holder (3160). For instance, when knob (3152) is in the distal position, knob (3152) may be operable to rotate needle (311). When knob (3152) is in the proximal position, knob (3152) may be operable to rotate tissue sample holder (3160). Various suitable components and features that may be used to provide such shifting functionality of knob (3152) will be apparent to those of ordinary skill in the art in view of the teachings herein.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A depth stop assembly for use with a biopsy device targeting cannula, the depth stop assembly comprising:
   a depth stop configured to receive the targeting cannula and having a lock to selectively restrict axial movement of the targeting cannula relative to the depth stop;
   a depth stop holder having a body configured to receive the depth stop; and
   a thumbwheel motion-coupled to the body such that the depth stop is secured within the body between the thumbwheel and an exterior of the body, the thumbwheel having a pair of actuation members configured to receive the depth stop and further configured to rotate the depth stop relative to the body to engage the lock of the depth stop with the targeting cannula, the thumbwheel including a circumferential finger gripping area.

2. The depth stop assembly of claim 1, the thumbwheel further including a rotation member having the circumferential finger gripping area and configured to secure the depth stop within the body of the depth stop holder.

3. The depth stop assembly of claim 2, the rotation member being further configured to restrict rotation of the depth stop to a predetermined range of motion relative to the depth stop holder.

4. The depth stop assembly of claim 2, the rotation member including one or more actuation members configured to manipulate the depth stop through a predetermined range of motion via rotation of the thumbwheel.

5. The depth stop assembly of claim 4, the depth stop holder being configured to receive the targeting cannula and be rotationally locked relative to the targeting cannula when the targeting cannula is received by the depth stop holder.

6. The depth stop assembly of claim 4, the depth stop holder defining one or more partially circumferential openings configured to engage the one or more actuation members of the rotation member to restrict rotation of the depth stop to the predetermined range of motion.

7. The depth stop assembly of claim 2, at least a portion of the depth stop holder defining a bore having an oval shape corresponding to the shape of the targeting cannula to thereby rotationally lock the depth stop holder relative to the targeting cannula.

8. The depth stop assembly of claim 7, the depth stop holder including a cross member with a portion of the cross member defining the bore.

9. The depth stop assembly of claim 8, the cross member defining one or more gaps corresponding to one or more actuation members of the rotation member, the cross member being configured to engage the one or more actuation members of the rotation member to restrict rotation of the depth stop to a predetermined range of motion.

10. The depth stop assembly of claim 2, the depth stop holder including a coupling member projecting distally from the body, the coupling member being configured to selectively secure the depth stop holder to a guide device associated with the targeting cannula.

11. The depth stop assembly of claim 10, the coupling member defining a connector channel configured to receive a protrusion of the guide device to provide selective coupling between the coupling member and a portion of the guide device.

12. The depth stop assembly of claim 2, the rotation member being configured to rotate the depth stop between a locked position and an unlocked position, the depth stop being configured to lock into a selected axial position along the length of the targeting cannula when the depth stop is in the locked position.

13. The depth stop assembly of claim 12, the depth stop including one or more blades with each blade of the one or more blades being configured to dig into the targeting cannula when the depth stop is in the locked position.

14. The depth stop assembly of claim 2, the rotation member including one or more lock arms with each lock arm of the one or more lock arms being configured to secure the rotation member to the depth stop holder while permitting rotation of the rotation member relative to the depth stop holder.

15. The depth stop assembly of claim 1, the circumferential gripping area including the entire circumference of the thumbwheel.

16. A guide system usable with a cannula, the guide system comprises:
(a) a depth stop assembly including:
(i) a depth stop configured to receive the cannula to thereby selectively restrict axial movement of the cannula, and
(iii) a thumbwheel assembly including a thumbwheel portion and a body, the thumbwheel portion being configured to selectively fasten to the body to secure the depth stop between the thumbwheel portion and the body, the thumbwheel portion being configured to rotate the depth stop through a predetermined range of motion relative to the body, the body including a restriction member configured to restrict rotation of the thumbwheel portion relative to the body to the predetermined range of motion; and
(b) a guide assembly including a body defining a plurality of guide holes extending from a distal end to a proximal end of the body of the guide assembly with each guide hole of the plurality of guide holes being configured to receive the cannula therein, at least a portion of the guide assembly being configured to couple to the thumbwheel assembly.

17. The guide system of claim 16, the guide assembly further including a lock feature selectively movable relative to the body of the guide assembly to selectively couple at least a portion of the thumbwheel assembly to at least a portion of the guide assembly.

18. The guide system of claim 17, further including a depth stop holder associated with the thumbwheel assembly, the lock feature of the guide assembly further including a hub, the hub being rotatable relative to the body of the guide assembly to selectively couple the lock feature of the guide assembly to the depth stop holder associated with the thumbwheel assembly.

19. The guide system of claim 18, the hub including at least one lock protrusion configured to engage at least a portion of the depth stop holder when the hub is rotated relative to the body of the guide assembly.

20. A depth stop assembly for use with a biopsy device targeting cannula, the depth stop assembly comprising:
(a) a depth stop configured to receive the targeting cannula and further configured to selectively restrict axial movement of the targeting cannula relative to the depth stop; and
(b) a depth stop holder including a body and a thumbwheel portion, the body defines a hollow interior and is configured to receive the depth stop, the thumbwheel portion being configured to couple to the body to hold the depth stop within the hollow interior of the body such that the depth stop is interposed between the thumbwheel portion and the body, the thumbwheel portion is further having one or more actuation members configured to rotate the depth stop through a predetermined range of motion relative to the body when the thumbwheel portion is coupled to the body, the body having a rotation restriction member configured to engage the one or more actuation members and prevent rotation of the depth stop outside of the predetermined range of motion.

* * * * *